US012612429B2

(12) United States Patent
Mendelsohn et al.

(10) Patent No.: US 12,612,429 B2
(45) **Date of Patent: *Apr. 28, 2026**

(54) DERIVATIVES OF DOLAPROINE-DOLAISOLEUINE PEPTIDES

(71) Applicant: AGENSYS, INC., Northbrook, IL (US)

(72) Inventors: Brian Alan Mendelsohn, San Diego, CA (US); Julien Dugal-Tessier, Belmont, MA (US); Stuart Daniel Barnscher, Surrey (CA)

(73) Assignee: AGENSYS, INC., Northbrook, IL (US)

( * ) Notice: Subject to any disclaimer, the term of this patent is extended or adjusted under 35 U.S.C. 154(b) by 587 days.

This patent is subject to a terminal disclaimer.

(21) Appl. No.: 17/698,353

(22) Filed: Mar. 18, 2022

(65) Prior Publication Data

US 2022/0204557 A1 Jun. 30, 2022

Related U.S. Application Data

(63) Continuation of application No. 16/684,208, filed on Nov. 14, 2019, now Pat. No. 11,312,748, which is a continuation of application No. 15/313,906, filed as application No. PCT/US2015/032704 on May 27, 2015, now abandoned.

(60) Provisional application No. 62/004,084, filed on May 28, 2014.

(51) Int. Cl.
*C07K 5/02* (2006.01)
*A61K 38/00* (2006.01)
*A61K 38/07* (2006.01)

(52) U.S. Cl.
CPC ............ *C07K 5/0205* (2013.01); *A61K 38/07* (2013.01); *A61K 38/00* (2013.01)

(58) Field of Classification Search
CPC ........ C07K 5/0205; C07K 7/02; A61K 38/07; A61K 38/00; A61K 38/03; A61K 38/08; A61P 35/00
See application file for complete search history.

(56) References Cited

U.S. PATENT DOCUMENTS

| | | | |
|---|---|---|---|
| 5,635,483 A | 6/1997 | Pettit et al. | |
| 5,654,399 A | 8/1997 | Sakakibara et al. | |
| 5,663,149 A | 9/1997 | Pettit et al. | |
| 5,767,237 A | 6/1998 | Sakakibara et al. | |
| 5,780,588 A | 7/1998 | Pettit et al. | |
| 6,004,934 A | 12/1999 | Sakakibara et al. | |
| 6,124,431 A | 9/2000 | Sakakibara et al. | |
| 6,323,315 B1 | 11/2001 | Pettit et al. | |
| 6,569,834 B1 | 5/2003 | Pettit et al. | |
| 6,884,869 B2 | 4/2005 | Senter et al. | |
| 8,288,352 B2 | 10/2012 | Doronina et al. | |
| 11,312,748 B2 * | 4/2022 | Mendelsohn | A61P 35/00 |
| 2003/0083263 A1 * | 5/2003 | Doronina | C07K 5/0205 514/19.3 |
| 2004/0254343 A1 * | 12/2004 | Miyazaki | A61P 35/00 530/330 |
| 2008/0038267 A1 | 2/2008 | Burnie et al. | |
| 2008/0300192 A1 * | 12/2008 | Doronina | A61K 49/0008 530/331 |
| 2013/0066055 A1 | 3/2013 | Lerchen et al. | |
| 2013/0190248 A1 | 7/2013 | Mendelsohn et al. | |
| 2014/0050746 A1 | 2/2014 | Senter et al. | |
| 2017/0190735 A1 | 7/2017 | Mendelsohn et al. | |

FOREIGN PATENT DOCUMENTS

| | | |
|---|---|---|
| CN | 101242816 A | 8/2008 |
| EP | 0598129 A1 | 5/1994 |
| EP | 0695757 A2 | 2/1996 |
| EP | 0695758 A2 | 2/1996 |
| JP | H 06234790 | 8/1994 |
| JP | 2004531544 A | 10/2004 |
| JP | 2014512375 A | 5/2014 |
| JP | 2020128405 A | 8/2020 |
| RU | 2556129 C2 | 7/2015 |
| WO | WO 1993003054 A1 | 2/1993 |
| WO | WO 1995009864 A1 | 4/1995 |
| WO | WO 2001018032 A2 | 3/2001 |
| WO | WO 2002088172 A2 | 11/2002 |
| WO | WO 2005039492 A2 | 5/2005 |
| WO | WO 2006132670 A2 | 12/2006 |
| WO | WO 2007005838 A2 | 1/2007 |
| WO | WO 2007005838 A3 | 1/2007 |
| WO | WO 2007008603 A1 | 1/2007 |
| WO | WO 2009126934 A2 | 10/2009 |
| WO | WO 2009126934 A3 | 10/2009 |
| WO | WO 2009095447 A1 | 11/2009 |
| WO | WO 2013072813 A2 | 5/2013 |
| WO | WO 2013173391 A1 | 11/2013 |
| WO | WO 2013173393 A1 | 11/2013 |
| WO | WO 2014072888 A1 | 5/2014 |

(Continued)

OTHER PUBLICATIONS

BioSynthesis, 2008, "Why acetylate and amidate a peptide," retrieved from internet: https://www.biosyn.com/faq/why-acetylate-and-amidate-a-peptide.aspx on May 13, 2019.
Delaney et al., 2005, "The role of radiotherapy in cancer treatment: estimating optimal utilization from a review of evidence-based clinical guidelines," Cancer, 104(6):1129-1137.
Doronina et al., 2006, "Enhanced activity of monomethylauristatin F through monoclonal antibody delivery: effects of linker technology on efficacy and toxicity," Bioconjug Chem., 17(1):114-124.
Fennell et al., 2003, Effects of the antimitotic natural product dolastatin 10, and related peptides, on the human malarial parasite Plasmodium falciparum, J Antimicrob Chemother., 51(4):833-841.
International Preliminary Report on Patentability issued Nov. 29, 2016 of International Patent Application No. PCT/US2015/032704 (published as WO 2015183978) (5 pages).

(Continued)

*Primary Examiner* — Lianko G Garyu
(74) *Attorney, Agent, or Firm* — JONES DAY

(57) ABSTRACT

Provided are peptide analogs, pharmaceutical compositions comprising such compounds, and methods of treating cancer with such compounds.

16 Claims, 30 Drawing Sheets

(56) References Cited

FOREIGN PATENT DOCUMENTS

| | | | |
|---|---|---|---|
| WO | WO 2014072897 | A1 | 5/2014 |
| WO | WO 2015183978 | A1 | 12/2015 |

OTHER PUBLICATIONS

International Search Report mailed on Aug. 12, 2015 of International Patent Application No. PCT/US2015/032704 (published as WO 2015183978) (2 pages).
Jagasia et al., 2009, "Peptide cyclization and cyclodimerization by Cu(I)-mediated azide-alkyne cycloaddition," J Org Chem., 74(8):2964-2974.
Miyazaki et al., 1995, "Synthesis and Antitumor Activity of Novel Dolastatin 10 Analogs," Chem Pharm Bull (Tokyo), 43(10):1706-1718.
Otani et al., 2000, "TZT-1027, an Antimicrotubule Agent, Attachs Tumor Vasculature and Induces Tumor Cell Death," Jpn J Cancer Res., 91(8):837-844.
Pettit et al., 1995, "Antineoplastic agents 337. Synthesis of dolastatin 10 structural modifications," Anti-Cancer Drug Design, 10(7):529-544.
Pettit et al., 1998, "Antineoplastic agents 365. Dolastatin 10 SAR probes," Anticancer Drug Des., 13(4):243-277.
Pettit et al., 1998, "Antineoplastic agents 365. Dolastatin 10 SAR probes," Antimicrobial Agents and Chemotherarpy, 42(11):2961-2965.
Pettit et al., 2011, "Antineoplastic Agents. 592. Highly Effective Cancer Cell Growth Inhibitory Structural Modifications of Dolastatin 10," J. Nat. Prod., 74(5):962-968.
Reithofer et al., 2014, "Ligation of anti-cancer drugs to self-assembling ultrashort peptides by click chemistry for localized therapy," Chem. Sci., 5:625 (10 pages), published online Oct. 18, 2013.
Shnyder et al., 2007, "Auristain PYE, a novel synthetic derivative of dolastatin 10, is highly effective in human colon tumor models," Int J Oncol., 31(2):353-360.
Supplementary European Search Report mailed on May 4, 2018 of European Patent Application No. 15799069.8 (20 pages).
Thermo Electron Corporation, 2004, Technical Information, "N-Terminal Acetylation and C-Terminal Amidation of Peptides," Thermo Electron GmbH (2 pages).
Woyke et al., 2001, "In Vitro Activities and Postantifungal Effects of the Potent Dolastatin 10 Derivative Auristatin PHE," Antimicrobial Agents and Chemotherapy, 45(12):3580-3584.
Kobayashi et al., 1997, "Antitumor activity of TZT-1027, a novel dolastatin 10 derivative," Jpn. J. Cancer Res., 88(3):316-327.

* cited by examiner

DERIVATIVES OF DOLAPROINE-DOLAISOLEUINE PEPTIDES

CROSS-REFERENCE TO RELATED APPLICATIONS

This application is a continuation of U.S. patent application Ser. No. 16/684,208, filed Nov. 14, 2019, now U.S. Pat. No. 11,312,748, issued Apr. 26, 2022, which is a continuation of U.S. patent application Ser. No. 15/313,906, filed Nov. 23, 2016, now abandoned, which is a U.S. National Stage Application under 35 U.S.C. § 371 of International Patent Application No. PCT/US2015/032704, filed May 27, 2015, which claims the benefit of U.S. Provisional Patent Application No. 62/004,084, filed May 28, 2014, the disclosure of each of which is incorporated by reference herein in its entirety.

FIELD OF INVENTION

Provided herein are dolaproine-dolaisoleuine peptide analogs, pharmaceutical compositions comprising such compounds, and methods of treating cancer with such compounds.

BACKGROUND

Cancer is the second leading cause of human death exceeded only by coronary disease. In the U.S., cancer accounts for nearly 1 in 4 deaths. Worldwide, millions of people die from cancer every year. In the United States alone, as reported by the American Cancer Society, cancer causes the death of well over a half-million people annually, with over 1.5 million new cases diagnosed per year. While deaths from heart disease have been declining significantly, those resulting from cancer generally are on the rise. In the early part of the next century, cancer is predicted to become the leading cause of death unless new medicines are found.

Worldwide, several cancers stand out as the leading killers. In particular, carcinomas of the lung, prostate, breast, colon, pancreas, ovary, and bladder represent the primary causes of cancer death. With very few exceptions, metastatic cancer is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients experience physical debilitations following treatment. Furthermore, many cancer patients experience a recurrence.

Promising new cancer therapeutics include the dolastatins and synthetic dolastatin analogs such as auristatins (U.S. Pat. Nos. 5,635,483, 5,780,588, 6,323,315, and 6,884,869; Shnyder et al. (2007) *Int. J. Oncol.* 31:353-360; Otani, M. et al. *Jpn. J. Cancer Res.* 2000, 91, 837-844; PCT Intl. Publ. Nos. WO 01/18032 A3, WO 2005/039492, WO 2006/132670, and WO 2009/095447; Fennell, B. J. et al., *J. Antimicrob. Chemther.* 2003, 51, 833-841). Dolastatins and auristatins have been shown to interfere with microtubule dynamics, thus disrupting cell division (Woyke et al. (2001) *Antimicrob. Agents Chemother.* 45(12):3580-3584), and have anticancer (U.S. Pat. No. 5,663,149) and antifungal activity (Pettit et al. (1998) *Antimicrob. Agents Chemother.* 42:2961-2965). Unfortunately, despite early enthusiasm, dolastatin 10 showed poor results as a single agent in phase II clinical trials (Shnyder (2007), supra). Certain compounds in the auristatins family have shown greater promise as clinical candidates with improved efficacy and pharmacological characteristics over the dolastatins (Pettit et al. (1995) *Anti-Cancer Drug Des.* 10:529-544; Pettit et al. (1998) *Anti-Cancer Drug Des.* 13:243-277; Shnyder (2007), supra). Various synthetic analogs of this structural type have been described (U.S. Pat. Nos. 6,569,834; 6,124,431; and Pettit et al. (2011) *J. Nat. Prod.* 74:962-968).

The auristatins have several properties which make them attractive for pharmaceutical development. First, these compounds are extremely potent. Second, their preparation is straight-forward because of the peptidic scaffold. Third, they possess good pharmacokinetic and metabolic profiles compared to peptides in general, or to other cancer drug classes in particular.

Despite significant advances, there remains a need for new anticancer therapeutics with desirable pharmaceutical properties.

SUMMARY

Provided herein are novel dolaproine-dolaisoleuine peptide analogs. Thus, provided herein are compounds of Formula (I):

(I)

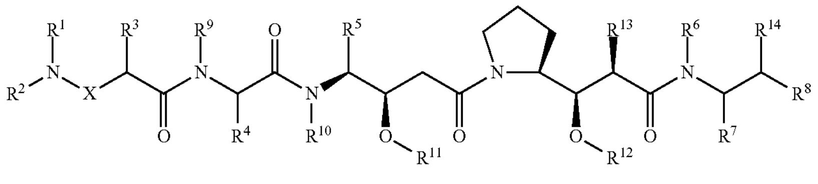

wherein $R^1$ and $R^2$ are each independently —H or alkyl;

X is —O—, —$NR^z$—, —S—, or is absent;

wherein $R^z$ is —H or alkyl;

$R^3$ is a group of the formula:

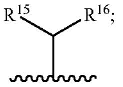

wherein $R^{15}$ and $R^{16}$ are each independently —H, —OH, —$NH_2$, —SH, —$N_3$, alkyl, alkenyl, alkynyl, -alkyl-OH, -alkyl-$NH_2$, -alkyl-SH, or -alkyl-$N_3$;

$R^4$ is a group of the formula:

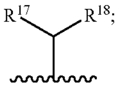

wherein $R^{17}$ and $R^{18}$ are each independently —H, —OH, —$NH_2$, —SH, —$N_3$, —$CO_2H$, alkyl, alkenyl, alkynyl, -alkyl-OH, -alkyl-$NH_2$, -alkyl-SH, -alkyl-$N_3$ or -alkyl-$CO_2H$ $R^5$ is sec-butyl or isobutyl;

$R^6$ is —H or alkyl;

$R^7$ and $R^8$ are each independently —H, alkyl, —$CO_2R^a$, $CONR^bR^c$, substituted or unsubstituted phenyl, or substituted or unsubstituted heterocyclic ring;

wherein $R^a$ is —H or alkyl;

$R^b$ and $R^c$ are each independently H or alkyl;

$R^9$ is —H or alkyl; or $R^9$ is taken together with $R^4$ and the atoms to which they are attached to form a substituted or unsubstituted heterocycloalkyl ring;

$R^{10}$ is —H or alkyl;

$R^{11}$ is —H or alkyl;

$R^{12}$ is —H or alkyl;

$R^{13}$ is —H or alkyl; and $R^{14}$ is —H, —OH or alkyl;

provided that when X is absent and $R^{15}$, $R^{16}$, $R^{17}$ and $R^{18}$ are each methyl, then $R^8$ is not substituted or unsubstituted phenyl, or substituted or unsubstituted heterocyclic ring;

or a pharmaceutically acceptable salt thereof.

Also provided herein is a pharmaceutical composition comprising an effective amount of at least one compound of Formula (I), or a pharmaceutically acceptable salt thereof, and a pharmaceutically acceptable excipient.

Also provided herein is a method of treating a subject suffering from or diagnosed with cancer, comprising administering to a subject in need of such treatment an effective amount of at least one compound of Formula (I), or a pharmaceutically acceptable salt thereof.

Also provided herein is use of at least one compound of Formula (I), or a pharmaceutically acceptable salt thereof, for treatment of cancer in a subject in need of such treatment.

Also provided herein is use of at least one compound of Formula (I), or a pharmaceutically acceptable salt thereof, in the manufacture of a medicament for treatment of cancer in a subject in need of such treatment.

Also provided herein is a kit containing at least one compound of Formula (I), or a pharmaceutically acceptable salt thereof, for use in treating cancer in a subject in need of such treatment, and instructions for use.

Also provided herein is an article of manufacture comprising at least one compound of Formula (I), or a pharmaceutically acceptable salt thereof, for use in treating cancer in a subject in need of such treatment.

DETAILED DESCRIPTION

Figure 1:
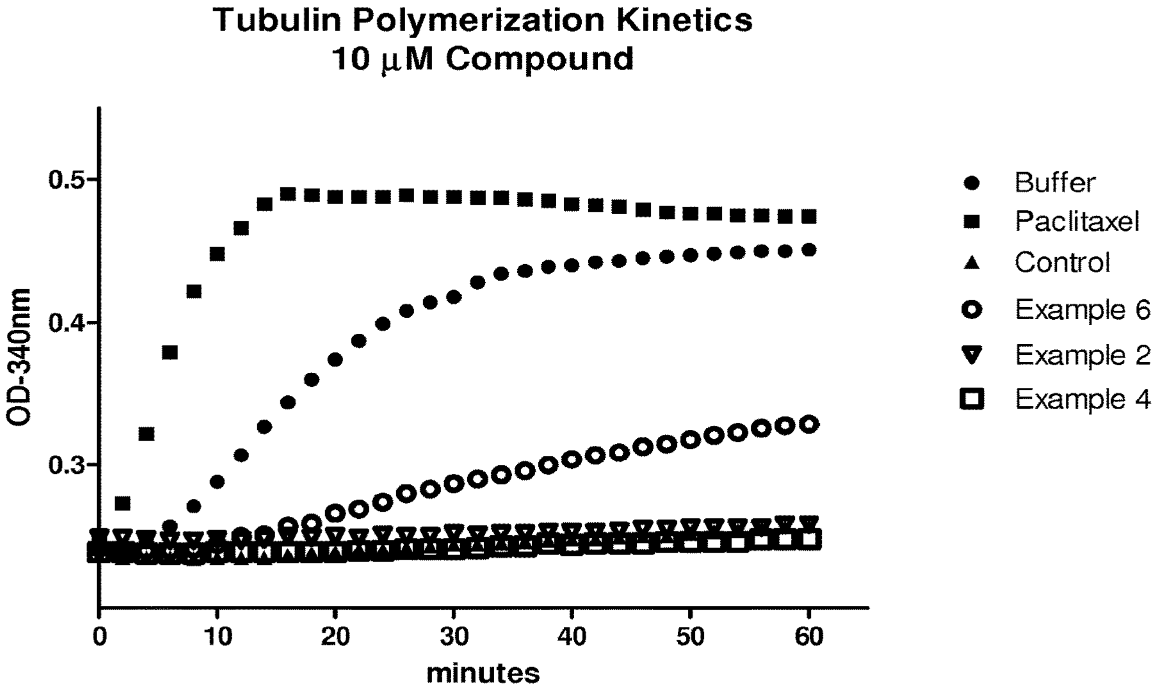
FIG. 1 shows in vitro tubulin polymerization data for tubulin treated with Example 2, Example 4, and Example 6. Untreated (buffer) tubulin shows the basal level of tubulin polymerization. A tubulin stabilizer (Paclitaxel) and a tubulin de-stabilizer (Control) were used as controls. All compounds were used at a final concentration of 10 μM.

For the sake of brevity, the disclosures of the publications cited in this specification, including patents, are herein incorporated by reference.

As used herein, the terms “including,” “containing,” and “comprising” are used in their open, non-limiting sense.

To provide a more concise description, some of the quantitative expressions given herein are not qualified with the term “about”. It is understood that, whether the term “about” is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

The term “alkyl,” by itself or as part of another term, refers to a saturated $C_1$-$C_{12}$ hydrocarbon containing normal, secondary, tertiary or cyclic carbon atoms. Particular alkyl groups are those having 1 to 8 carbon atoms, 1 to 6 carbon atoms, or 1 to 4 carbon atoms.

Examples of alkyl groups include, but are not limited to: methyl (Me), ethyl (Et), n-propyl, isopropyl, butyl, isobutyl, sec-butyl, tert-butyl (tBu), n-pentyl, isopentyl, tert-pentyl, and n-hexyl, isohexyl. In some embodiments, an alkyl group has normal, secondary, or tertiary carbon atoms and does not have cyclic carbon atoms.

The term “alkenyl,” by itself or as part of another term, refers to a $C_2$-$C_{12}$ hydrocarbon containing normal, secondary, tertiary or cyclic carbon atoms with at least one site of unsaturation, i.e., a carbon-carbon, $sp^2$ double bond. Particular alkenyl groups are those having 2 to 8 carbon atoms, 2 to 6 carbon atoms, or 2 to 4 carbon atoms. Examples include, but are not limited to: vinyl ($-CH{=}CH_2$), allyl ($-CH_2CH_2{=}CH_2$), cyclopentenyl ($-C_5H_7$), and 5-hexenyl ($-CH_2CH_2CH_2CH_2CH{=}CH_2$). In some embodiments, an alkenyl group has normal, secondary, or tertiary carbon atoms and does not have cyclic carbon atoms.

The term "alkynyl," by itself or as part of another term, refers to a $C_2$-$C_{12}$ hydrocarbon containing normal, secondary, tertiary or cyclic carbon atoms with at least one site of unsaturation, i.e., a carbon-carbon, sp triple bond. Particular alkynyl groups are those having 2 to 8 carbon atoms, 2 to 6 carbon atoms, or 2 to 4 carbon atoms. Examples include, but are not limited to: ethynyl ($-C{\equiv}CH$) and 2-propynyl ($-CH_2C{\equiv}CH$). In some embodiments, an alkynyl group has normal, secondary, or tertiary carbon atoms and does not have cyclic carbon atoms.

The term "alkoxy" refers to an —O-alkyl group, where the O is the point of attachment to the rest of the molecule, and alkyl is as defined above.

The term "heterocycloalkyl" refers to a monocyclic, or fused, bridged, or spiro polycyclic ring structure that is saturated or partially saturated and has from 3 to 12 ring atoms per ring structure selected from carbon atoms and up to three heteroatoms selected from nitrogen, oxygen, and sulfur. Particular heterocycloalkyl groups are those having from 3 to 8 ring atoms or from 5 to 7 ring atoms per ring structure. The ring structure may optionally contain up to two oxo groups on carbon or sulfur ring members. Illustrative entities, in the form of properly bonded moieties, include:

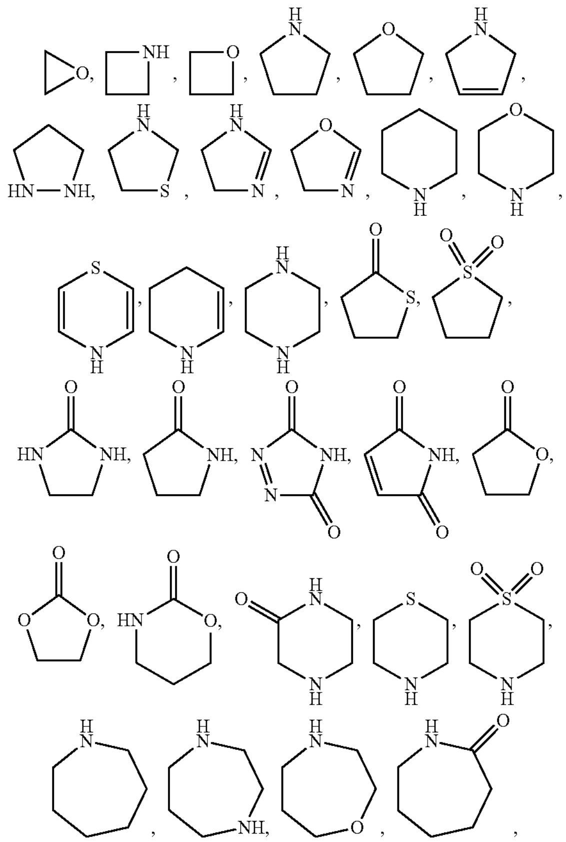

-continued

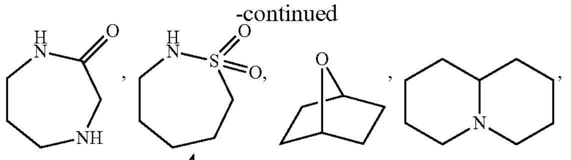

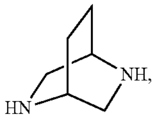

and

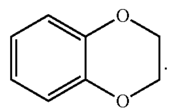

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Particular heteroaryl groups are those having from 3 to 8 ring atoms or from 5 to 7 ring atoms per ring structure. Illustrative examples of heteroaryl groups include the following entities, in the form of properly bonded moieties:

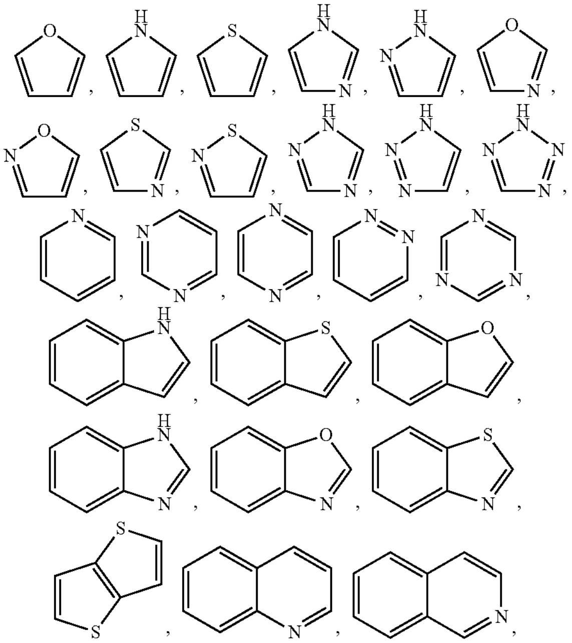

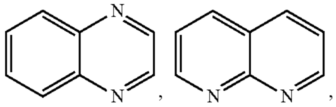

and

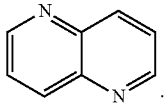

The terms "heterocycle," "heterocyclic," or "heterocyclyl" as used herein encompass both the "heterocycloalkyl" and "heteroaryl" moieties as defined above.

Those skilled in the art will recognize that the species of heterocyclyl, heteroaryl and heterocycloalkyl groups listed or illustrated above are not exhaustive, and that additional species within the scope of these defined terms may also be selected.

The term "halogen" represents chlorine, fluorine, bromine, or iodine. The term "halo" represents chloro, fluoro, bromo, or iodo.

The term "substituted" means that the specified group or moiety bears one or more substituents. The term "unsubstituted" means that the specified group bears no substituents.

The term "optionally substituted" means that the specified group is unsubstituted or substituted by one or more substituents. Where the term "substituted" is used to describe a structural system, the substitution is meant to occur at any valency-allowed position on the system.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers. Additionally, any formula given herein is intended to refer also to any one of hydrates, solvates, and amorphous and polymorphic forms of such compounds, and mixtures thereof, even if such forms are not listed explicitly. In some embodiments, the solvent is water and the solvates are hydrates.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds described herein include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{15}N$, $^{18}O$, $^{17}O$, $^{31}P$, $^{32}P$, F, $^{36}Cl$, and $^{125}I$, respectively. Such isotopically labeled compounds are useful in metabolic studies (preferably with $^{14}C$), reaction kinetic studies (with, for example $^{2}H$ or $^{3}H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^{2}H$) may afford certain therapeutic advantages resulting from greater metabolic stability, for example increased in vivo half-life or reduced dosage requirements. Isotopically labeled compounds described herein and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

The nomenclature "$C_{i-j}$" with j>i, when applied herein to a class of substituents, is meant to refer to embodiments of any of the compositions, uses, or methods described herein for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

The term $C_{n-m}$alkyl refers to an aliphatic chain, whether straight or branched, with a total number N of carbon members in the chain that satisfies $n \leq N \leq m$, with $m>n$.

Chemical names listed herein were generated using AutoNOM™ software. If there is a discrepancy between a chemical structure and the name listed for that structure, the structure prevails.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

In some embodiments, $R^1$ and $R^2$ are each independently —H or alkyl, for example $C_{1-6}$alkyl In some embodiments, $R^1$ and $R^2$ are each independently —H or methyl. In some embodiments, $R^1$ and $R^2$ are each independently alkyl. In some embodiments, $R^1$ and $R^2$ are both methyl. In some embodiments, $R^1$ and $R^2$ are both —H.

In some embodiments, X is absent. In other embodiments, X is —O—. In some embodiments, $R^1$ and $R^2$ are each independently alkyl, and X is absent. In some embodiments, $R^1$ and $R^2$ are both methyl, and X is absent. In other embodiments, $R^1$ and $R^2$ are both —H, and X is —O—. In some embodiments, X is —$NR^z$—, wherein $R^z$ is —H or alkyl. In some embodiments, $R^z$ is —H. In some embodiments, X is $R^z$ is alkyl, for example $C_{1-6}$alkyl or methyl.

In certain embodiments, $R^3$ is

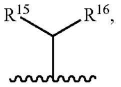

wherein $R^{15}$ and $R^{16}$ are each independently —H, —OH, —$NH_2$, —SH, —$N_3$, alkyl, alkenyl, alkynyl, -alkyl-OH, -alkyl-$NH_2$, -alkyl-SH, or -alkyl-$N_3$. In still other embodiments, $R^{15}$ and $R^{16}$ are each independently —H, alkyl, —$(CH_2)_{0-6}C\equiv CH$, —$(CH_2)_{0-6}CH{=}CH_2$, —$(CH_2)_{0-6}OH$, —$(CH_2)_{0-6}NH_2$, —$(CH_2)_{0-6}SH$, or —$(CH_2)_{0-6}N_3$. In some embodiments, $R^{15}$ and $R^{16}$ are each independently —H, —OH, or alkyl. In some embodiments, $R^{15}$ and $R^{16}$ are each independently —H, —OH, or methyl. In some embodiments, $R^{15}$ is —OH and $R^{16}$ is hydrogen. In some embodiments, $R^{15}$ is —OH and $R^{16}$ is methyl.

In certain embodiments, $R^3$ is in the R stereochemical configuration relative to the remainder of the molecule. In other embodiments, $R^3$ is in the S stereochemical configuration relative to the remainder of the molecule. In certain embodiments, the $R^3$ group itself contains one or more chiral centers, and those stereocenters are each independently in the R or S configuration.

In certain embodiments, $R^4$ is

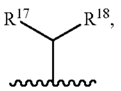

wherein $R^{17}$ and $R^{18}$ are each independently —H, —OH, —$NH_2$, —SH, —$N_3$, —$CO_2H$, alkyl, alkenyl, alkynyl, -alkyl-OH, -alkyl-$NH_2$, -alkyl-SH, -alkyl-$N_3$ or -alkyl-$CO_2H$. In other embodiments, $R^4$ is

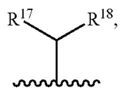

wherein $R^{17}$ is —H, —OH, —$NH_2$, —SH, —$N_3$, —$CO_2H$, alkyl, alkenyl, alkynyl, -alkyl-OH, -alkyl-$NH_2$, -alkyl-SH, -alkyl-$N_3$ or -alkyl-$CO_2H$, and $R^{18}$ is —H, —OH, —$NH_2$, —SH, —$N_3$, —$CO_2H$, alkenyl, alkynyl, -alkyl-OH, -alkyl-$NH_2$, -alkyl-SH, -alkyl-$N_3$ or -alkyl-$CO_2H$. In still other embodiments, $R^{17}$ and $R^{18}$ are each independently —H, alkyl, —$(CH_2)_{0-6}C{\equiv}CH$, —$(CH_2)_{0-6}CH{=}CH_2$, —$(CH_2)_{0-6}OH$, —$(CH_2)_{0-6}NH_2$, —$(CH_2)_{0-6}SH$, or —$(CH_2)_{0-6}N_3$. In some embodiments, $R^{17}$ and $R^{18}$ are each independently —H, —OH, —$NH_2$, —SH, —$N_3$, —$CO_2H$, alkyl, -alkyl-$NH_2$, or -alkyl-$N_3$. In some embodiments, $R^{17}$ and $R^{18}$ are each independently —H, —OH, —$NH_2$, —SH, —$N_3$, —$CO_2H$, methyl, —$CH_2NH_2$, or —$CH_2N_3$.

In certain embodiments, $R^4$ is taken together with $R^9$ and the atoms to which they are attached to form a substituted or unsubstituted heterocycloalkyl ring. In certain embodiments, $R^4$ is taken together with $R^9$ and the atoms to which they are attached to form a 5- to 7-member heterocycloalkyl ring, which may be unsubstituted or substituted with one or more groups selected from —OH, —$NH_2$, —SH, and —$N_3$. In certain embodiments, the heterocycloalkyl ring is a pyrrolidine ring, which may be unsubstituted or substituted with one or more groups selected from —OH, —$NH_2$, —SH, and —$N_3$.

In certain embodiments, $R^4$ is in the R stereochemical configuration relative to the remainder of the molecule. In other embodiments, $R^4$ is in the S stereochemical configuration relative to the remainder of the molecule. In certain embodiments, the $R^4$ group itself contains one or more chiral centers, and those stereocenters are each independently in the R or S configuration.

In certain embodiments, $R^5$ is sec-butyl. In other embodiments, $R^5$ is isobutyl. In certain embodiments, $R^5$ is in the R stereochemical configuration relative to the remainder of the molecule. In other embodiments, $R^5$ is in the S stereochemical configuration relative to the remainder of the molecule. In some embodiments, the chiral center within the $R^5$ group is in the R configuration, and in other embodiments, that center is in the S configuration.

In certain embodiments, $R^6$ is —H. In other embodiments, $R^6$ is alkyl, for example $C_{1-8}$alkyl, $C_{1-4}$alkyl, methyl, or ethyl.

In some embodiments, $R^7$ and $R^8$ are each independently is —H, alkyl, —$CO_2R^a$ or —$CONR^bR^c$; wherein $R^a$ is —H or alkyl, for example $C_{1-6}$alkyl or methyl; and $R^b$ and $R^c$ are each independently —H or alkyl, for example $C_{1-6}$alkyl or methyl.

In certain embodiments, $R^7$ and $R^8$ are each independently is substituted or unsubstituted phenyl or substituted or unsubstituted heterocyclic ring, wherein the phenyl or heterocyclic ring may be substituted with one or more groups selected from halo, oxo, hydroxy, amino, alkyl, and alkoxy. In certain other embodiments, $R^7$ is unsubstituted 3- to 8-member heterocyclic ring. In certain other embodiments, $R^7$ is substituted 3- to 8-member heterocyclic ring. In certain other embodiments, $R^8$ is phenyl which is optionally substituted with halo.

In certain embodiments, $R^7$ is in the R stereochemical configuration relative to the remainder of the molecule. In other embodiments, $R^7$ is in the S stereochemical configuration relative to the remainder of the molecule.

In certain embodiments, $R^8$ is in the R stereochemical configuration relative to the remainder of the molecule. In other embodiments, $R^8$ is in the S stereochemical configuration relative to the remainder of the molecule.

In some embodiments, $R^7$ is —$CO_2R^a$—$CONR^bR^c$; tetrazolyl or thiazolyl, wherein $R^a$ is —H or alkyl, for example $C_{1-6}$alkyl or methyl; and $R^b$ and $R^c$ are each independently —H or alkyl, for example $C_{1-6}$alkyl or methyl; and $R^{11}$ is phenyl which is optionally substituted with halo.

In some embodiments, $R^9$ is —H. In other embodiments, $R^9$ is alkyl, for example $C_{1-8}$alkyl, $C_{1-4}$alkyl, methyl, or ethyl. In some embodiments, $R^9$ is —H or methyl. In some embodiments, $R^9$ is methyl.

In some embodiments, $R^{10}$ is —H. In other embodiments, $R^{10}$ is alkyl, for example $C_{1-8}$alkyl, $C_{1-4}$alkyl, methyl, or ethyl. In some embodiments, $R^{10}$ is —H or methyl. In some embodiments, $R^{10}$ is methyl.

In some embodiments, $R^{11}$ is —H. In other embodiments, $R^{11}$ is alkyl, for example $C_{1-8}$alkyl, $C_{1-4}$alkyl, methyl, or ethyl. In some embodiments, $R^{11}$ is —H or methyl. In some embodiments, $R^1$ is methyl.

In some embodiments, $R^2$ is —H. In other embodiments, $R^{12}$ is alkyl, for example $C_{1-8}$alky, $C_{1-4}$alkyl, methyl, or ethyl. In some embodiments, $R^{12}$ is —H or methyl. In some embodiments, $R^{12}$ is methyl.

In some embodiments, $R^{13}$ is —H. In other embodiments, $R^{13}$ is alkyl, for example $C_{1-8}$alkyl, $C_{1-4}$alkyl, methyl, or ethyl. In some embodiments, $R^{13}$ is —H or methyl. In some embodiments, $R^{13}$ is methyl.

In some embodiments, $R^{14}$ is —H. In some embodiments, $R^{14}$ is alkyl, for example $C_{1-6}$alkyl, methyl, or ethyl. In some embodiments, $R^{14}$ is —OH.

In certain embodiments, $R^{14}$ is in the R stereochemical configuration relative to the remainder of the molecule. In other embodiments, $R^{14}$ is in the S stereochemical configuration relative to the remainder of the molecule.

In some embodiments, $R^7$ is —$CO_2R^a$, wherein $R^a$ is —H or alkyl, for example $C_{1-6}$alkyl or methyl; $R^8$ is phenyl; and $R^{14}$ is —H. In some embodiments, $R^7$ is —$CONR^bR^c$, wherein $R^b$ and $R^c$ are each independently —H or alkyl, for example $C_{1-6}$alkyl or methyl; $R^{14}$ is phenyl; and $R^{14}$ is —H. In some embodiments, $R^7$ is alkyl, for example $C_{1-6}$alkyl or methyl; $R^8$ is phenyl; and $R^{14}$ is —OH. In some embodiments, $R^7$ is methyl, $R^8$ is phenyl, and $R^{14}$ is —OH. In some embodiments, $R^7$ and $R^{14}$ are both —H, and $R^8$ is pyridinyl, piperidinyl, unsubstituted phenyl, or phenyl substituted with halo, for example fluoro, chloro, or bromo. In some embodiments, $R^7$ is —$CO_2R^a$, wherein $R^a$ is —H or alkyl, for example $C_{1-6}$alkyl or methyl; $R^8$ is —H or alkyl, for example $C_{1-6}$alkyl or methyl; and $R^{14}$ is alkyl, for example $C_{1-6}$alkyl, methyl, or ethyl. In some embodiments, $R^7$ is —$CO_2R^a$ wherein $R^a$ is —H or alkyl, for example $C_{1-6}$alkyl or methyl; $R^8$ is —H or alkyl, for example $C_{1-6}$alkyl or methyl; and $R^{14}$ is —OH.

In certain embodiments, $R^1$ and $R^2$ are each independently —H or $C_{1-6}$alkyl;

X is —O— or is absent;

$R^3$ is

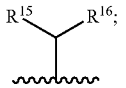

wherein $R^{15}$ and $R^{16}$ are each independently —H, —OH, or $C_{1-6}$allyl;

$R^4$ is

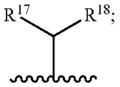

wherein $R^{17}$ is —OH, —$NH_2$, —SH, —$N_3$, —$CO_2H$, —$C_{1-6}$alkyl-$NH_2$, alkynyl, alkenyl, or —$C_{1-6}$alkyl-$N_3$; and $R^{18}$ is —H or $C_{1-6}$alkyl;

$R^5$ is sec-butyl;

$R^6$ is —H;

$R^7$ is —H, $C_{1-6}$alkyl, —$CO_2R^a$, —$CONR^bR^c$, tetrazolyl or thiazolyl; wherein $R^a$ is —H or $C_{1-6}$alkyl; and $R^b$ and $R^c$ are each —H or $C_{1-6}$alkyl;

$R^8$ is —H, $C_{1-6}$alkyl, substituted or unsubstituted phenyl or substituted or unsubstituted heterocyclic ring;

$R^9$ is —H;

$R^{10}$, $R^{11}$, $R^{12}$, and $R^{13}$ are each independently $C_{1-6}$alkyl; and $R^{14}$ is —H, $C_{1-6}$alkyl or —OH.

In certain embodiments, $R^1$ and $R^2$ are each independently —H or methyl;

X is —O— or is absent;

$R^3$ is

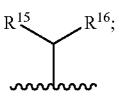

wherein $R^{15}$ and $R^{16}$ are each independently —H, —OH, or methyl;

$R^4$ is

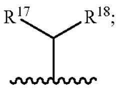

wherein $R^{17}$ is —OH, —$NH_2$, —SH, —$N_3$, —$CO_2H$, aminomethyl, alkynyl, alkenyl, or azidomethyl; and $R^{18}$ is —H or methyl;

$R^5$ is sec-butyl;

$R^6$ is —H;

$R^7$ is —H, methyl, —$CO_2R^a$, or —$CONR^bR^c$; wherein $R^a$ is —H or methyl; and $R^b$ and $R^c$ are each —H or methyl;

$R^8$ is —H, methyl, ethyl, pyridinyl, piperidinyl, unsubstituted phenyl, phenyl substituted with halo;

$R^9$ is —H;

$R^{10}$, $R^{11}$, $R^{12}$, and $R^{13}$ are each methyl; and $R^{14}$ is —H, methyl or —OH.

In certain embodiments, $R^1$ and $R^2$ are each independently —H or $C_{1-6}$alkyl;

X is absent;

$R^3$ is

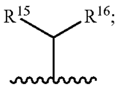

wherein $R^{15}$ and $R^{16}$ are each independently —H, —OH, or $C_{1-6}$alkyl;

$R^4$ is

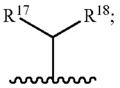

wherein $R^{17}$ is —$N_3$, and $R^{18}$ is —H or methyl;

$R^5$ is sec-butyl;

$R^6$ is —H;

$R^7$ is —H, $C_{1-6}$alkyl, —$CO_2R^a$, —$CONR^bR^c$, tetrazolyl or thiazolyl; wherein $R^a$ is —H or $C_{1-6}$alkyl; and $R^b$ and $R^c$ are each —H or $C_{1-6}$alkyl;

$R^8$ is —H, $C_{1-6}$alkyl, substituted or unsubstituted phenyl or substituted or unsubstituted heterocyclic ring;

$R^9$ is —H;

$R^{10}$, $R^{11}$, $R^{12}$, and $R^{13}$ are each independently $C_{1-6}$alkyl; and $R^{14}$ is —H, $C_{1-6}$alkyl or —OH.

In certain embodiments, $R^1$ and $R^2$ are each independently —H or $C_{1-6}$alkyl;

X is —O—;

$R^3$ is

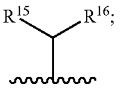

wherein $R^{15}$ and $R^{16}$ are each independently —H, —OH, or $C_{1-6}$alkyl;

$R^4$ is

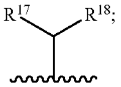

wherein $R^{17}$ is —$N_3$, and $R^{18}$ is —H or methyl;

$R^5$ is sec-butyl;

$R^6$ is —H;

$R^7$ is —H, $C_{1-6}$alkyl, —$CO_2R^a$, —$CONR^bR^c$, tetrazolyl or thiazolyl; wherein $R^a$ is —H or $C_{1-6}$alkyl; and $R^b$ and $R^c$ are each —H or $C_{1-6}$alkyl;

$R^8$ is —H, $C_{1-6}$alkyl, substituted or unsubstituted phenyl or substituted or unsubstituted heterocyclic ring;

$R^9$ is —H;

$R^{10}$, $R^{11}$, $R^{12}$, and $R^{13}$ are each independently $C_{1-6}$alkyl; and $R^{14}$ is —H, $C_{1-6}$alkyl or —OH.

In some embodiments of Formula (I), wherein, $R^1$ and $R^2$ are each methyl;

X is absent;

R3 is a group of the formula:

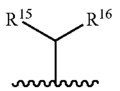

wherein $R^{15}$ and $R^{16}$ are each methyl;

$R^4$ is a group of the formula:

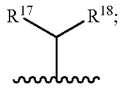

wherein $R^{17}$ is —$N_3$, —$NH_2$, —OH, —SH, and $R^{18}$ is —H or methyl;

$R^5$ is sec-butyl;

$R^6$ is —H;

$R^7$ is —$CO_2R^a$ or $CONR^bR^c$, wherein $R^a$ is —H or $C_{1-6}$alkyl;

$R^b$ and $R^c$ are each independently H or $C_{1-6}$alkyl;

$R^8$ is phenyl;

$R^9$ is —H;

$R^{10}$, $R^{11}$, $R^{12}$, and $R^{13}$ are each independently methyl; and $R^{14}$ is —H.

In some embodiments of Formula (I), wherein, $R^1$ and $R^2$ are each —H;

X is —O—;

R3 is a group of the formula:

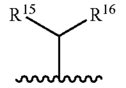

wherein $R^{15}$ and $R^{16}$ are each methyl $R^4$ is a group of the formula:

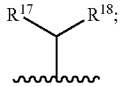

wherein $R^{17}$ is —$N_3$, and $R^{18}$ is —H or methyl;

$R^5$ is sec-butyl;

$R^6$ is —H;

$R^7$ is —$CO_2R^a$ or $CONR^bR^c$, wherein $R^a$ is —H or $C_{1-6}$alkyl;

$R^b$ and $R^c$ are each independently H or $C_{1-6}$alkyl;

$R^8$ is phenyl;

$R^9$ is —H;

$R^{10}$, $R^{11}$, $R^{12}$, and $R^3$ are each independently methyl; and $R^{14}$ is —H.

It is to be understood that any variable group definition provided herein can be used in combination with any other variable group definition provided herein, such that all possible combinations and permutations of variable groups provided herein, where chemically feasible, are contemplated.

In certain embodiments, compounds of Formula (I) are selected from the group consisting of:

(S)-methyl 2-((2R,3R)-3-((S)-1-((3R,4S,5S)-4-((S)-2-((S)-2-(dimethylamino)-3-methylbutanamido)-3-hydroxy-N-methylpropanamido)-3-methoxy-5-methylheptanoyl)pyrrolidin-2-yl)-3-methoxy-2-methylpropanamido)-3-phenylpropanoate;

(S)-methyl 2-((2R,3R)-3-((S)-1-((3R,4S,5S)-4-((2S,3R)-2-((S)-2-(dimethylamino)-3-methylbutanamido)-3-hydroxy-N-methylbutanamido)-3-methoxy-5-methylheptanoyl)pyrrolidin-2-yl)-3-methoxy-2-methylpropanamido)-3-phenylpropanoate;

(S)-2-(dimethylamino)-N—((S)-3-hydroxy-1-(((3R,4S,5S)-3-methoxy-1-((S)-2-((1R,2R)-1-methoxy-2-methyl-3-oxo-3-((2-(pyridin-2-yl)ethyl)amino)propyl)pyrrolidin-1-yl)-5-methyl-1-oxoheptan-4-yl)(methyl)amino)-1-oxopropan-2-yl)-3-methylbutanamide;

(2S,3R)-2-((S)-2-(dimethylamino)-3-methylbutanamido)-3-hydroxy-N-((3R,4S,5S)-3-methoxy-1-((S)-2-((1R,2R)-1-methoxy-2-methyl-3-oxo-3-((2-(pyridin-2-yl)ethyl)amino)propyl)pyrrolidin-1-yl)-5-methyl-1-oxoheptan-4-yl)-N-methylbutanamide;

(2S)-2-(dimethylamino)-N-((2S)-3-hydroxy-1-(((3R,4S,5S)-3-methoxy-1-((2S)-2-((1R,2R)-1-methoxy-2-methyl-3-oxo-3-((2-(piperidin-2-yl)ethyl)amino)propyl)pyrrolidin-1-yl)-5-methyl-1-oxoheptan-4-yl)(methyl)amino)-1-oxopropan-2-yl)-3-methylbutanamide;

(2S,3R)-2-((S)-2-(dimethylamino)-3-methylbutanamido)-3-hydroxy-N-((3R,4S,5S)-3-methoxy-1-((2S)-2-((1R,2R)-1-methoxy-2-methyl-3-oxo-3-((2-(piperidin-2-yl)ethyl)amino)propyl)pyrrolidin-1-yl)-5-methyl-1-oxoheptan-4-yl)-N-methylbutanamide;

(S)-methyl 2-((2R,3R)-3-((S)-1-((3R,4S,5S)-4-((2S,3S)-3-azido-2-((S)-2-(dimethylamino)-3-methylbutanamido)-N-methylbutanamido)-3-methoxy-5-methylheptanoyl)pyrrolidin-2-yl)-3-methoxy-2-methylpropanamido)-3-phenylpropanoate;

(S)-methyl 2-((2R,3R)-3-((S)-1-((3R,4S,5S)-4-((S)-3-amino-2-((S)-2-(dimethylamino)-3-methylbutanamido)-N-methylpropanamido)-3-methoxy-5-methylheptanoyl)pyrrolidin-2-yl)-3-methoxy-2-methylpropanamido)-3-phenylpropanoate;

(S)—N—((S)-3-amino-1-(((3R,4S,5S)-3-methoxy-1-((S)-2-((1R,2R)-1-methoxy-2-methyl-3-oxo-3-((2-(pyridin-2-yl)ethyl)amino)propyl)pyrrolidin-1-yl)-5-methyl-1-oxoheptan-4-yl)(methyl)amino)-1-oxopropan-2-yl)-2-(dimethylamino)-3-methylbutanamide;

(S)-methyl 2-((2R,3R)-3-((S)-1-((3R,4S,5S)-4-((S)-3-azido-2-((S)-2-(dimethylamino)-3-methylbutanamido)-N-methylpropanamido)-3-methoxy-5-methylheptanoyl)pyrrolidin-2-yl)-3-methoxy-2-methylpropanamido)-3-phenylpropanoate;

(S)-methyl 2-((2R,3R)-3-((S)-1-((3R,4S,5S)-4-((S)-4-azido-2-((S)-2-(dimethylamino)-3-methylbutanamido)-N-methylbutanamido)-3-methoxy-5-methylheptanoyl)pyrrolidin-2-yl)-3-methoxy-2-methylpropanamido)-3-phenylpropanoate;

(S)-methyl 2-((2R,3R)-3-((S)-1-((3R,4S,5S)-4-((S)-4-amino-2-((S)-2-(dimethylamino)-3-methylbutanamido)-N-methylbutanamido)-3-methoxy-5-methylheptanoyl)pyrrolidin-2-yl)-3-methoxy-2-methylpropanamido)-3-phenylpropanoate;

(S)-2-((S)-2-(aminooxy)-3-methylbutanamido)-N-(3R,4S,5S)-3-methoxy-1-((S)-2-((1R,2R)-1-methoxy-2-methyl-3-oxo-3-((2-(pyridin-2-yl)ethyl)amino)propyl)pyrrolidin-1-yl)-5-methyl-1-oxoheptan-4-yl)-N,3-dimethylbutanamide;

((2R,3R)-3-((S)-1-((3R,4S,5S)-4-((S)-2-((S)-2-(dimethylamino)-3-hydroxypropanamido)-N,3-dimethylbutanamido)-3-methoxy-5-methylheptanoyl)pyrrolidin-2-yl)-3-methoxy-2-methylpropanoyl)-L-phenylalanine;

((2R,3R)-3-((S)-1-((3R,4S,5S)-4-((S)-2-((2S,3R)-2-(dimethylamino)-3-hydroxybutanamido)-N,3-dimethylbutanamido)-3-methoxy-5-methylheptanoyl)pyrrolidin-2-yl)-3-methoxy-2-methylpropanoyl)-L-phenylalanine;

(S)-2-((2R,3R)-3-((S)-1-((3R,4S,5S)-4-((2S,3S)-3-azido-2-((S)-2-(dimethylamino)-3-methylbutanamido)-N-methylbutanamido)-3-methoxy-5-methylheptanoyl)pyrrolidin-2-yl)-3-methoxy-2-methylpropanamido)-3-phenylpropanoic acid;

(S)—N-((3R,4S,5S)-1-((S)-2-((1R,2R)-3-(((S)-1-amino-1-oxo-3-phenylpropan-2-yl)amino)-1-methoxy-2-methyl-3-oxopropyl)pyrrolidin-1-yl)-3-methoxy-5-methyl-1-oxoheptan-4-yl)-2-((2S,3R)-2-(dimethylamino)-3-hydroxybutanamido)-N,3-dimethylbutanamide;

(S)—N-((3R,4S,5S)-1-((S)-2-((1R,2R)-3-(((S)-1-amino-1-oxo-3-phenylpropan-2-yl)amino)-1-methoxy-2-methyl-3-oxopropyl)pyrrolidin-1-yl)-3-methoxy-5-methyl-1-oxoheptan-4-yl)-2-((S)-2-(dimethylamino)-3-hydroxypropanamido)-N,3-dimethylbutanamide;

(S)-methyl 2-((2R,3R)-3-((S)-1-((3R,4S,5S)-4-((R)-2-((S)-2-(dimethylamino)-3-methylbutanamido)-3-mercapto-N-methylpropanamido)-3-methoxy-5-methylheptanoyl)pyrrolidin-2-yl)-3-methoxy-2-methylpropanamido)-3-phenylpropanoate;

(S)-2-((2R,3R)-3-((S)-1-((3R,4S,5S)-4-((R)-2-((S)-2-(dimethylamino)-3-methylbutanamido)-3-mercapto-N-methylpropanamido)-3-methoxy-5-methylheptanoyl)pyrrolidin-2-yl)-3-methoxy-2-methylpropanamido)-3-phenylpropanoic acid;

(S)-2-((2R,3R)-3-((S)-1-((3R,4S,5S)-4-((S)-2-((S)-2-(dimethylamino)-3-methylbutanamido)-3-hydroxy-N-methylpropanamido)-3-methoxy-5-methylheptanoyl)pyrrolidin-2-yl)-3-methoxy-2-methylpropanamido)-3-phenylpropanoic acid;

(S)-2-((2R,3R)-3-((S)-1-((3R,4S,5S)-4-((2S,3R)-2-((S)-2-(dimethylamino)-3-methylbutanamido)-3-hydroxy-N-methylbutanamido)-3-methoxy-5-methylheptanoyl)pyrrolidin-2-yl)-3-methoxy-2-methylpropanamido)-3-phenylpropanoic acid;

(S)-methyl 2-((2R,3R)-3-((S)-1-((3R,4S,5S)-4-((S)-2-((S)-2-(dimethylamino)-3-hydroxypropanamido)-N,3-dimethylbutanamido)-3-methoxy-5-methylheptanoyl)pyrrolidin-2-yl)-3-methoxy-2-methylpropanamido)-3-phenylpropanoate;

(S)-methyl 2-((2R,3R)-3-((S)-1-((3R,4S,5S)-4-((S)-2-((2S,3R)-2-(dimethylamino)-3-hydroxybutanamido)-N,3-dimethylbutanamido)-3-methoxy-5-methylheptanoyl)pyrrolidin-2-yl)-3-methoxy-2-methylpropanamido)-3-phenylpropanoate;

(S)-methyl 2-((2R,3R)-3-((S)-1-((3R,4S,5S)-4-((2S,3S)-3-amino-2-((S)-2-(dimethylamino)-3-methylbutanamido)-N-methylbutanamido)-3-methoxy-5-methylheptanoyl)pyrrolidin-2-yl)-3-methoxy-2-methylpropanamido)-3-phenylpropanoate;

(S)-2-((2R,3R)-3-((S)-1-((3R,4S,5S)-4-((2S,3S)-3-amino-2-((S)-2-(dimethylamino)-3-methylbutanamido)-N-methylbutanamido)-3-methoxy-5-methylheptanoyl)pyrrolidin-2-yl)-3-methoxy-2-methylpropanamido)-3-phenylpropanoic acid;

(2S,3S)-3-azido-2-((S)-2-(dimethylamino)-3-methylbutanamido)-N-((3R,4S,5S)-3-methoxy-1-((S)-2-((1R,2R)-1-methoxy-2-methyl-3-oxo-3-(phenethylamino)propyl)pyrrolidin-1-yl)-5-methyl-1-oxoheptan-4-yl)-N-methylbutanamide;

(2S,3S)-3-azido-2-((S)-2-(dimethylamino)-3-methylbutanamido)-N-((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N-methylbutanamide;

(2S,3S)-3-azido-N-((3R,4S,5S)-1-((S)-2-((1R,2R)-3-((4-chlorophenethyl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N-methylbutanamide;

(2S,3S)-3-azido-N-((3R,4S,5S)-1-((S)-2-((1R,2R)-3-((2-chlorophenethyl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N-methylbutanamide;

(2S,3S)-3-amino-2-((S)-2-(dimethylamino)-3-methylbutanamido)-N-((3R,4S,5S)-3-methoxy-1-((S)-2-((1R,2R)-1-methoxy-2-methyl-3-oxo-3-(phenethylamino)propyl)pyrrolidin-1-yl)-5-methyl-1-oxoheptan-4-yl)-N-methylbutanamide;

(2S,3S)-3-amino-2-((S)-2-(dimethylamino)-3-methylbutanamido)-N-((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N-methylbutanamide;

(2S,3S)-3-amino-N-((3R,4S,5S)-1-((S)-2-((1R,2R)-3-((4-chlorophenethyl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N-methylbutanamide;

(2S,3S)-3-amino-N-((3R,4S,5S)-1-((S)-2-((1R,2R)-3-((2-chlorophenethyl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N-methylbutanamide;

(S)-4-amino-2-((S)-2-(dimethylamino)-3-methylbutanamido)-N-((3R,4S,5S)-3-methoxy-1-((S)-2-((1R,2R)-1-methoxy-2-methyl-3-oxo-3-(phenethylamino)propyl)pyrrolidin-1-yl)-5-methyl-1-oxoheptan-4-yl)-N-methylbutanamide;

(S)-4-amino-2-((S)-2-(dimethylamino)-3-methylbutanamido)-N-((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N-methylbutanamide;

(S)-4-amino-N-((3R,4S,5S)-1-((S)-2-((1R,2R)-3-((4-chlorophenethyl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N-methylbutanamide;

(S)-4-amino-N-((3R,4S,5S)-1-((S)-2-((1R,2R)-3-((2-chlorophenethyl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N-methylbutanamide;

methyl ((2R,3R)-3-((S)-1-((3R,4S,5S)-4-((S)-2-((S)-2-(dimethylamino)-3-methylbutanamido)-N-methylpent-4-ynamido)-3-methoxy-5-methylheptanoyl)pyrrolidin-2-yl)-3-methoxy-2-methylpropanoyl)-L-phenylalaninate;

(2S,3S)—N-((3R,4S,5S)-1-((S)-2-((1R,2R)-3-(((S)-1-amino-1-oxo-3-phenylpropan-2-yl)amino)-1-methoxy-2-methyl-3-oxopropyl)pyrrolidin-1-yl)-3-methoxy-5-methyl-1-oxoheptan-4-yl)-3-azido-2-((S)-2-(dimethylamino)-3-methylbutanamido)-N-methylbutanamide;

(2S,3S)-3-azido-2-((S)-2-(dimethylamino)-3-methylbutanamido)-N-((3R,4S,5S)-3-methoxy-1-((S)-2-((1R,2R)-1-methoxy-2-methyl-3-oxo-3-((2-(pyridin-2-yl)ethyl)amino)propyl)pyrrolidin-1-yl)-5-methyl-1-oxoheptan-4-yl)-N-methylbutanamide;

(2S,3S)-3-azido-N-((3R,4S,5S)-1-((S)-2-((1R,2R)-3-(((S)-1-(tert-butylamino)-1-oxo-3-phenylpropan-2-yl)amino)-1-methoxy-2-methyl-3-oxopropyl)pyrrolidin-1-yl)-3- methoxy-5-methyl-1-oxoheptan-4-yl)-2-((S)-2-(dimethylamino)-3-methylbutanamido)-N-methylbutanamide;
methyl ((2R,3R)-3-((S)-1-((3R,4S,5S)-4-((2S,3S)-3-azido-2-((S)-2-(dimethylamino)-3-methylbutanamido)-N-methylbutanamido)-3-methoxy-5-methylheptanoyl)pyrrolidin-2-yl)-3-methoxy-2-methylpropanoyl)-L-valinate;
methyl ((2R,3R)-3-((S)-1-((3R,4S,5S)-4-((S)-6-amino-2-((S)-2-(dimethylamino)-3-methylbutanamido)-N-methylhexanamido)-3-methoxy-5-methylheptanoyl)pyrrolidin-2-yl)-3-methoxy-2-methylpropanoyl)-L-phenylalaninate;
methyl ((2R,3R)-3-((S)-1-((3R,4S,5S)-4-((2S,4S)-4-azido-1-(dimethyl-L-valyl)-N-methylpyrrolidine-2-carboxamido)-3-methoxy-5-methylheptanoyl)pyrrolidin-2-yl)-3-methoxy-2-methylpropanoyl)-L-phenylalaninate;
(S)-3-((S)-2-(dimethylamino)-3-methylbutanamido)-4-(((3R,4S,5S)-3-methoxy-1-((S)-2-((1R,2R)-1-methoxy-3-(((S)-1-methoxy-1-oxo-3-phenylpropan-2-yl)amino)-2-methyl-3-oxopropyl)pyrrolidin-1-yl)-5-methyl-1-oxoheptan-4-yl)(methyl)amino)-4-oxobutanoic acid;
(2S,3R)-2-((S)-2-(dimethylamino)-3-methylbutanamido)-3-hydroxy-N-((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N-methylbutanamide;
methyl ((2R,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanoyl)-L-serinate;
methyl ((2R,3R)-3-((S)-1-((3R,4S,5S)-4-((2S,3S)-3-azido-2-((S)-2-(dimethylamino)-3-methylbutanamido)-N-methylbutanamido)-3-methoxy-5-methylheptanoyl)pyrrolidin-2-yl)-3-methoxy-2-methylpropanoyl)-L-isoleucinate;
(2S,3S)-3-amino-N-((3R,4S,5S)-1-((S)-2-((1R,2R)-3-(((S)-1-amino-1-oxo-3-phenylpropan-2-yl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N-methylbutanamide;
(2S,3S)-3-amino-N-((3R,4S,5S)-1-((S)-2-((1R,2R)-3-(((S)-1-(tert-butylamino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N-methylbutanamide;
methyl ((2R,3R)-3-((S)-1-((3R,4S,5S)-4-((S)-3-azido-N-methyl-2-((S)-3-methyl-2-(methylamino)butanamido)propanamido)-3-methoxy-5-methylheptanoyl)pyrrolidin-2-yl)-3-methoxy-2-methylpropanoyl)-L-phenylalaninate;
methyl ((2R,3R)-3-((S)-1-((3R,4S,5S)-4-((2S,3S)-3-azido-N-methyl-2-((S)-3-methyl-2-(methylamino)butanamido)butanamido)-3-methoxy-5-methylheptanoyl)pyrrolidin-2-yl)-3-methoxy-2-methylpropanoyl)-L-phenylalaninate;
(2S,3S)—N-((3R,4S,5S)-1-((S)-2-((1R,2R)-3-(((S)-1-amino-1-oxo-3-phenylpropan-2-yl)amino)-1-methoxy-2-methyl-3-oxopropyl)pyrrolidin-1-yl)-3-methoxy-5-methyl-1-oxoheptan-4-yl)-3-azido-N-methyl-2-((S)-3-methyl-2-(methylamino)butanamido)butanamide;
((2S,3S)-3-azido-N-((3R,4S,5S)-1-((S)-2-((1R,2R)-3-(((S)-1-(tert-butylamino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)-N-methyl-2-((S)-3-methyl-2-(methylamino)butanamido)butanamide;
tert-butyl ((2R,3R)-3-((S)-1-((3R,4S,5S)-4-((2S,3S)-3-azido-N-methyl-2-((S)-3-methyl-2-(methylamino)butanamido)butanamido)-3-methoxy-5-methylheptanoyl)pyrrolidin-2-yl)-3-methoxy-2-methylpropanoyl)-L-phenylalaninate;

((2R,3R)-3-((S)-1-((3R,4S,5S)-4-((2S,3S)-3-azido-N-methyl-2-((S)-3-methyl-2-(methylamino)butanamido)butanamido)-3-methoxy-5-methylheptanoyl)pyrrolidin-2-yl)-3-methoxy-2-methylpropanoyl)-L-phenylalanine;
tert-butyl ((2R,3R)-3-((S)-1-((3R,4S,5S)-4-((2S,3S)-3-azido-2-((S)-2-(dimethylamino)-3-methylbutanamido)-N-methylbutanamido)-3-methoxy-5-methylheptanoyl)pyrrolidin-2-yl)-3-methoxy-2-methylpropanoyl)-L-phenylalaninate;
(2S,3S)-3-azido-2-((S)-2-(dimethylamino)-3-methylbutanamido)-N-((3R,4S,5S)-3-methoxy-1-((S)-2-((1R,2R)-1-methoxy-2-methyl-3-oxo-3-(((S)-2-phenyl-1-(1H-tetrazol-5-yl)ethyl)amino)propyl)pyrrolidin-1-yl)-5-methyl-1-oxoheptan-4-yl)-N-methylbutanamide;
(2S,3S)-3-azido-N-((3R,4S,5S)-3-methoxy-1-((S)-2-((1R,2R)-1-methoxy-2-methyl-3-oxo-3-(((S)-2-phenyl-1-(1H-tetrazol-5-yl)ethyl)amino)propyl)pyrrolidin-1-yl)-5-methyl-1-oxoheptan-4-yl)-N-methyl-2-((S)-3-methyl-2-(methylamino)butanamido)butanamide;
(2S,3S)-3-azido-2-((S)-2-(dimethylamino)-3-methylbutanamido)-N-((3R,4S,5S)-3-methoxy-1-((S)-2-((1R,2R)-1-methoxy-2-methyl-3-oxo-3-(((S)-2-phenyl-1-(thiazol-2-yl)ethyl)amino)propyl)pyrrolidin-1-yl)-5-methyl-1-oxoheptan-4-yl)-N-methylbutanamide;
tert-butyl ((2R,3R)-3-((S)-1-((3R,4S,5S)-4-((2S,3S)-3-amino-2-((S)-2-(dimethylamino)-3-methylbutanamido)-N-methylbutanamido)-3-methoxy-5-methylheptanoyl)pyrrolidin-2-yl)-3-methoxy-2-methylpropanoyl)-L-phenylalaninate;
(2S,3S)-3-amino-2-((S)-2-(dimethylamino)-3-methylbutanamido)-N-((3R,4S,5S)-3-methoxy-1-((S)-2-((1R,2R)-1-methoxy-2-methyl-3-oxo-3-(((S)-2-phenyl-1-(1H-tetrazol-5-yl)ethyl)amino)propyl)pyrrolidin-1-yl)-5-methyl-1-oxoheptan-4-yl)-N-methylbutanamide; and
(2S,3S)-3-amino-2-((S)-2-(dimethylamino)-3-methylbutanamido)-N-((3R,4S,5S)-3-methoxy-1-((S)-2-((1R,2R)-1-methoxy-2-methyl-3-oxo-3-(((S)-2-phenyl-1-(thiazol-2-yl)ethyl)amino)propyl)pyrrolidin-1-yl)-5-methyl-1-oxoheptan-4-yl)-N-methylbutanamide;
and pharmaceutically acceptable salts thereof.

Also provided herein are pharmaceutically acceptable salts of the compounds of Formula (I), preferably of those described above and the specific compounds exemplified herein, pharmaceutical compositions comprising such salts, and methods of using such salts.

A "pharmaceutically acceptable salt" is intended to mean a salt of a free acid or base of a compound represented herein that is non-toxic, biologically tolerable, or otherwise biologically suitable for administration to the subject. See, generally, S. M. Berge, et al. "Pharmaceutical Salts," *J. Pharm. Sci.* 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include acid addition salts such as sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates, and salts with inorganic bases such as sodium, potassium, magnesium, calcium, aluminum, and the like or organic bases such as methylamine, ethylamine, ethanolamine, lysine, ornithine, and the like, salts with various amino acids or amino acid derivatives such as acetylleucine and the like, ammonium salts, etc.

For treatment purposes, pharmaceutical compositions comprising compounds described herein may further comprise one or more pharmaceutically-acceptable excipients. A pharmaceutically-acceptable excipient is a substance that is non-toxic and otherwise biologically suitable for administration to a subject. Such excipients facilitate formulation and administration of a compound described herein and are compatible with the active ingredient. Examples of pharmaceutically-acceptable excipients include stabilizers, lubricants, surfactants, diluents, anti-oxidants, binders, coloring agents, emulsifiers, or taste-modifying agents. In preferred embodiments, pharmaceutical compositions are sterile compositions.

The pharmaceutical compositions described herein may be formulated as solutions, emulsions, suspensions, or dispersions in suitable pharmaceutical solvents or carriers, or as pills, tablets, lozenges, suppositories, powders for reconstitution, or capsules along with solid carriers according to conventional methods known in the art for preparation of various dosage forms. For topical applications, the compounds described herein are preferably formulated as creams or ointments or a similar vehicle suitable for topical administration. The pharmaceutical compositions and compounds described herein may be administered in the inventive methods by a suitable route of delivery, e.g., oral, nasal, parenteral, rectal, topical, ocular, or by inhalation.

The term "treat" or "treating" as used herein is intended to refer to administration of a compound described herein to a subject for the purpose of creating a therapeutic benefit. Treating includes reversing, ameliorating, alleviating, inhibiting the progress of, or lessening the severity of, a disease, disorder, or condition, or one or more symptoms of cancer. The term "subject" refers to a mammalian patient in need of such treatment, such as a human.

In treatment methods provided herein, "an effective amount" means an amount or dose sufficient to generally bring about the desired therapeutic benefit in subjects needing such treatment. Effective amounts or doses of the compounds described herein may be ascertained by routine methods, such as modeling, dose escalation or clinical trials, taking into account routine factors, e.g., the mode or route of administration or drug delivery, the pharmacokinetics of the agent, the severity and course of the infection, the subject's health status, condition, and weight, and the judgment of the treating physician. An exemplary dose is in the range of about 1 ug to 2 mg of active compound per kilogram of subject's body weight per day, preferably about 0.05 to 100 mg/kg/day, or about 1 to 35 mg/kg/day, or about 0.1 to 10 mg/kg/day. The total dosage may be given in single or divided dosage units (e.g., BID, TID, QID).

The compounds described herein may be used in pharmaceutical compositions or methods in combination with additional active ingredients in the treatment of cancer. The additional active ingredients may be administered separately from a compound described herein or may be included with a compound described herein in a pharmaceutical composition provided herein. For example, additional active ingredients are those that are known or discovered to be effective in treating cancer, including those active against another target associated with cancer, such as but not limited to, Velcade, Rituximab, Methotrexate, Herceptin, Vincristine, Prednisone, Irinotecan, or the like, or a combination thereof. Such a combination may serve to increase efficacy, decrease one or more side effects, or decrease the required dose of a disclosed compound.

The compounds described herein may be used in pharmaceutical compositions or methods in combination with additional active ingredients in the treatment of cancer. The additional active ingredients may be administered separately from a compound described herein or may be included with a compound described herein in a pharmaceutical composition provided herein. For example, additional active ingredients are those that are known or discovered to be effective in treating cancer, including those active against another target associated with cancer, such as but not limited to, Velcade, Rituximab, Methotrexate, Herceptin, Vincristine, Prednisone, Irinotecan, or the like, or a combination thereof. Such a combination may serve to increase efficacy, decrease one or more side effects, or decrease the required dose of a disclosed compound.

Compounds of Formula (I) will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. In addition, one of skill in the art will recognize that protecting groups may be used to protect certain functional groups (amino, carboxy, or side chain groups) from reaction conditions, and that such groups are removed under standard conditions when appropriate. Each of the reactions depicted in Scheme A is preferably run at a temperature from about room temperature to the reflux temperature of the organic solvent used. Unless otherwise specified, the variables are as defined above in reference to Formula (I).

Scheme A

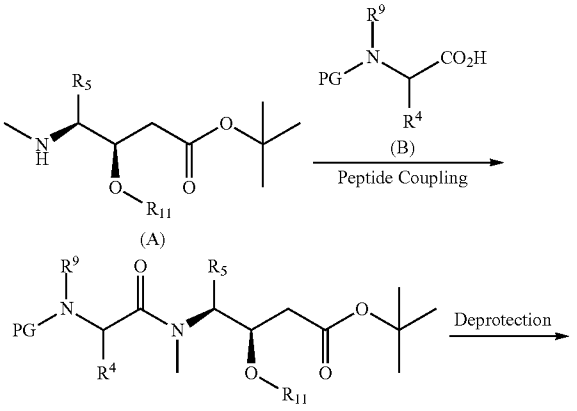

(C)

-continued

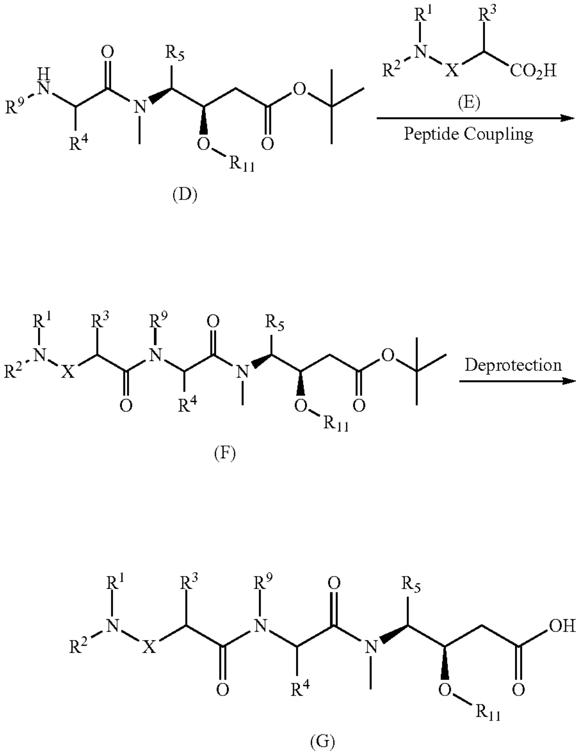

(D) (E) (F) (G)

Scheme B

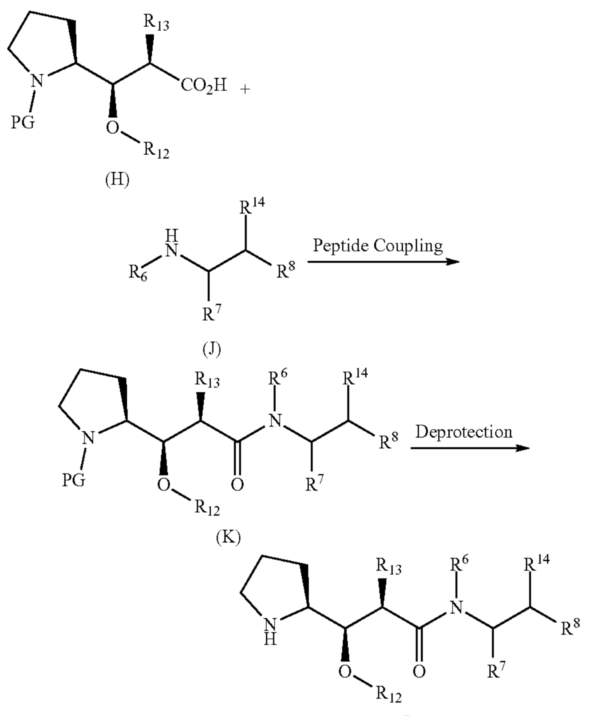

(H) (J) (K) (L)

Referring to Scheme A, the preparation of compounds of Formula (I) begins with a protected acid form of dolaisoleuine (Dil) labeled (A) (see Pettit et al. (1994) *J. Org. Chem.* 59:1796-1800). Compound (A) is depicted with a tert-butyl ester protecting group, but one of skill in the art may select an appropriate replacement. Coupling with a nitrogen-protected valine or isoleucine derivative (B), where PG is a suitable amino protecting group such as a Boc (t-butoxycarbonyl) or fluorenylmethyloxycarbonyl (Fmoc) group, is effected under standard peptide coupling conditions. For example, reactions are run in the presence of diethyl cyanophosphonate (DEPC), PyBrOP, PyBOP, BOP, diisopropylcarbodiimide (DIC), dicyclohexylcarbodiimide (DCC), 1-(3-dimethylaminopropyl)-3-ethylcarbodiimide hydrochloride (EDCI), 1-hydroxybenzotriazole (HOBt), 1-hydroxy-7-aza-benzotriazole (HOAt), HBTU (O-benzotriazol-1-yl-N,N,N',N'-tetramethyluronium hexafluorophosphate), HATU (0-(7-azabenzotriazol-1-yl)-1,1,3,3-tetramethyluronium hexafluorophosphate), and the like, or a combination thereof. Reactions are typically run in the presence of a tertiary amine base, such as diisopropylethylamine. Suitable solvents include dichloromethane, N,N-dimethylformamide (DMF), dimethyl sulfoxide (DMSO), ethyl acetate and the like. The amino protecting group on resultant dipeptide (C) is removed by deprotection under suitable conditions. For example, where PG is a Boc group, compound (C) is treated with trifluoroacetic acid to form free amine (D). Where PG is an Fmoc group, compound (C) is treated with piperidine or diethylamine to yield compound (D). Compound (D) is then coupled to amino acid derivative (E), in protected form if necessary, under peptide coupling conditions as described above, to generate tripeptide (F). Treatment with acid removes the carboxy protecting group to provide free acid (G).

Referring to Scheme B, the amino-protected dolaproine (Dap) designated as (H) (see Pettit et al. (1994) *J. Org. Chem.* 59:6287-6295) is coupled with amine (J) (which is prepared using methods known to one in the art) under peptide coupling conditions as described above. Resulting dipeptide (K) is deprotected as discussed for Scheme A to provide compound (L).

Scheme C (G) + (L) Peptide Coupling (I)

Referring to Scheme C, acid (G) and amine (L) are coupled under peptide coupling conditions as discussed above to provide compounds of Formula (I). Where the result of the reaction is a protected form of Formula (I), suitable deprotection conditions are employed to give the target compound.

EXAMPLES

The following examples are offered to illustrate but not to limit the compositions, uses, and methods provided herein. The compounds are prepared using the general methods described above.

The following chemical abbreviations are used throughout the Examples: Dov (dolavaline); Abu (2-aninobutyric acid); Dil (dolaisoleuine); Dpr (2,3-dianinopropionic acid); Su (succinimidinyl); Dab (2,4-diaminobutyric acid); Dap (dolaproine); Bzl (benzyl); and Tr (trityl).

LCMS retention times were acquired on an Aquity UPLC BeH C8 1.7 μm 2.1×50 mm column, 40° C., using one of the following methods (as indicated):

Method A: 0-0.50 min: isocratic 80 water/10 acetonitrile/10 1% formic acid in water; 0.50-3.50 min: linear gradient 80 water/10 acetonitrile/10 1% formic acid in water to 0 water/90 acetonitrile/10 1% formic acid in water; 3.50-3.99 min isocratic 0 water/90 acetonitrile/10 1% formic acid in water; 3.99-4.00 min linear gradient 0 water/90 acetonitrile/10 1% formic acid in water to 80 water/10 acetonitrile/10 1% formic acid in water.

Method B: 0-0.50 min: isocratic 85 water/5 acetonitrile/10 1% formic acid in water; 0.50-1.60 min: linear gradient 85 water/5 acetonitrile/10 1% formic acid in water to 0 water/98 acetonitrile/2 1% formic acid in water; 1.60-1.80 min isocratic 0 water/98 acetonitrile/2 1% formic acid in water; 1.80-1.90 min linear gradient 0 water/98 acetonitrile/2 1% formic acid in water to 85 water/5 acetonitrile/10 1% formic acid in water; 1.90-2.00 min isocratic 85 water/5 acetonitrile/10 1% formic acid in water.

Example 1

(S)-methyl 2-((2R,3R)-3-((S)-1-((3R,4S,5S)-4-((S)-2-((S)-2-(dimethylamino)-3-methylbutanamido)-3-hydroxy-N-methylpropanamido)-3-methoxy-5-methylheptanoyl)pyrrolidin-2-yl)-3-methoxy-2-methylpropanamido)-3-phenylpropanoate

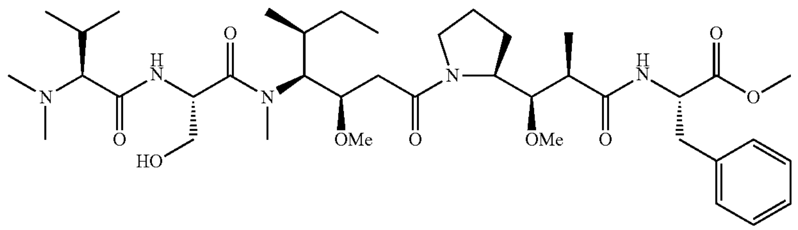

To a stirred room temperature suspension of Boc-Dap-OH dicyclohexylamine salt (8.00 g, 17.1 mmol) and H-Phe-OMe HCl salt (4.42 g, 20.5 mmol) in $CH_2Cl_2$ (20 mL) was added diisopropylethylamine (DIEA; 9.13 mL, 51.3 mmol), followed by diethylpyrocarbonate (DEPC; 5.15 mL, 34.2 mmol). After 10 h, analysis by liquid chromatography/mass spectrometry (LCMS) showed the reaction was complete. Boc-Dap-Phe-OMe was isolated by flash chromatography on silica gel (silica gel 40 m, 60 Å, 3.0×17.0 cm) using 2% to 10% MeOH in $CH_2Cl_2$ as the eluent. A total of 7.45 g of Boc-Dap-Phe-OMe (16.61 mmol, 97% yield) was obtained.

To a stirred room temperature solution of Boc-Dap-Phe-OMe (4.67 g, 10.4 mmol) in $CH_2Cl_2$ (10 mL) was added trifluoroacetic acid (TFA; 10 mL). After 10 h, analysis by LCMS showed the reaction was complete. The crude oil was purified by preparatory RP-HPLC with a Phenomenex Synergi 10 Max-RP 80 Å column (150×30 mm) using 10% to 90% MeCN in 0.05% aqueous TFA as the eluent. A total of 2.52 g H-Dap-Phe-OMe (6.23 mmol, 59%) was obtained as the TFA salt.

To a stirred room temperature solution of Fmoc-Ser(Bzl)-OH (2.82 g, 6.76 mmol) and H-Dil-OtBu hydrochloride (2.00 g, 6.76 mmol) in ethyl acetate (EtOAc; 15 mL) was added DIEA (2.17 mL, 12.2 mmol). The solution was cooled to (0° C.) and stirred for 20 min. DIEA (2.17 mL, 12.2 mmol) was added to the reaction mixture. The solution was cooled to (0° C.) and stirred for 20 min. 2-Chloro-1-methylpyridinium iodide (CMPI; 2.76 g, 10.8 mmol) was added to the reaction mixture and the reaction mixture was allowed to reach room temperature. After 12 h, analysis by LCMS showed the reaction was complete. The crude reaction was washed with 0.1 M HCl (150 mL×2). The organic fraction was dried over a pad of magnesium sulfate, filtered and concentrated in vacuo. Fmoc-Ser(Bzl)-Dil-OtBu was isolated by flash chromatography on silica gel (silica gel 40 μm, 60 Å, 3.0×17.0 cm) using 18% to 90% EtOAc in hexanes as the eluent. A total of 3.75 g of Fmoc-Ser(Bzl)-Dil-OtBu (5.69 mmol, 84% yield) was obtained.

To a stirred room temperature solution of Fmoc-Ser(Bzl)-Dil-OtBu (1.79 g, 2.72 mmol) in MeCN (5 mL) was added piperidine (4 mL). After 5 h, analysis by LCMS showed the reaction was complete. The crude reaction mixture was extracted with Hexanes and the MeCN layer was concentrated in vacuo to yield crude H-Ser(Bzl)-Dil-OtBu that was used without further purification.

To a stirred room temperature suspension of crude H-Ser (Bzl)-Dil-OtBu and Dov (0.790 g, 5.44 mmol) in DMF (10 mL) was added DIEA (1.45 mL, 8.16 mmol), followed by HATU (2.07 g, 5.44 mmol). After 5 h, analysis by LCMS showed that the reaction was complete. The crude reaction mixture was diluted with saturated sodium bicarbonate (10 mL) and extracted with EtOAc (40 mL×2). The combined organic fractions were washed with brine, dried over a pad of magnesium sulfate, filtered, and concentrated in vacuo. The crude oil was purified by preparatory RP-HPLC with a Phenomenex Synergi 10p Max-RP 80 Å column (150×30 mm) using 10% to 90% MeCN in 0.05% aqueous TFA as the eluent. A total of 0.882 g Dov-Ser(Bzl)-Dil-OtBu (1.30 mmol, 48%) was obtained as the TFA salt.

To a room temperature solution of Dov-Ser(Bzl)-Dil-OtBu (0.288 g, 0.425 mmol) in $CH_2Cl_2$ (5 mL) was added TFA (4 mL). After 10 h, analysis by LCMS showed the reaction was complete. Volatile organics were evaporated in vacuo to yield crude Dov-Ser(Bzl)-Dil-OH TFA salt that was used without further purification.

To a stirred room temperature suspension of crude Dov-Ser(Bzl)-Dil-OH TFA salt and H-Dap-Phe-OMe TFA salt (0.163 g, 0.467 mmol) in DMF (10 mL) was added DIEA (0.303 mL, 1.70 mmol), followed by HATU (0.323 g, 0.850 mmol). After 6 h, analysis by LCMS showed the reaction was complete. The crude reaction mixture was diluted with saturated sodium bicarbonate (10 mL) and extracted with EtOAc (40 mL×2). The combined organic fractions were washed with brine, dried over a pad of magnesium sulfate, filtered, and concentrated in vacuo. The crude oil was purified by preparatory RP-HPLC with a Phenomenex Synergi 10p Max-RP 80 Å column (150×30 mm) using 10% to 90% MeCN in 0.05% aqueous TFA as the eluent. A total of 0.217 g Dov-Ser(Bzl)-Dil-Dap-Phe-OMe (0.228 mmol, 54%) was obtained as the TFA salt.

A stirred room temperature suspension of Dov-Ser(Bzl)-Dil-Dap-Phe-OMe TFA salt (0.217 g, 0.228 mmol) and palladium on activated charcoal (10% Pd basis, 0.174 g) in MeOH (5 mL) was hydrogenated under refluxing conditions. After 48 h, analysis by LCMS showed the reaction was complete. The crude reaction mixture was filtered over a pad of diatomaceous earth and the filtrate was concentrated. The crude oil was purified by preparatory RP-HPLC with a Phenomenex Synergi 10 μL Max-RP 80 Å column (150×30 mm) using 10% to 90% MeCN in 0.05% aqueous TFA as the eluent. A total of 0.104 g of the title compound was obtained as the TFA salt (0.121 mmol, 47%). LCMS RT=2.32 min (Method A); ESI-MS m/z 748.72 $[M+H]^+$; HRMS m/z 748.4846 $[C_{39}H_{65}N_5O_9+H]^+$.

Example 2

(S)-methyl 2-((2R,3R)-3-((S)-1-((3R,4S,5S)-4-((2S,3R)-2-((S)-2-(dimethylamino)-3-methylbutanamido)-3-hydroxy-N-methylbutanamido)-3-methoxy-5-methylheptanoyl)pyrrolidin-2-yl)-3-methoxy-2-methylpropanamido)-3-phenylpropanoate

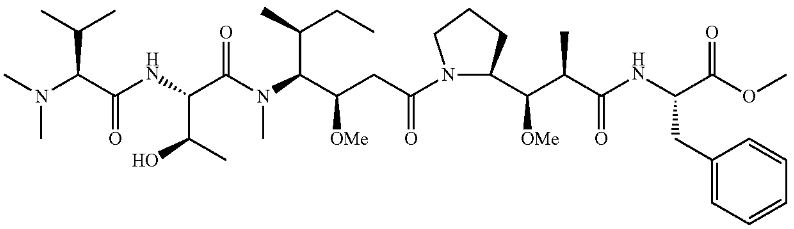

To a stirred room temperature solution of Fmoc-Thr(Bzl)-OH (2.92 g, 6.76 mmol) and H-Dil-OtBu hydrochloride (2.00 g, 6.76 mmol) in EtOAc (15 mL) was added DIEA (2.17 mL, 12.2 mmol). The solution was cooled (0° C.) and stirred for 20 min. DIEA (2.17 mL, 12.2 mmol) was added to the reaction mixture. The solution was cooled (0° C.) and stirred for 20 min. CMPI (2.76 g, 10.8 mmol) was added to the reaction mixture and the reaction mixture was allowed to reach room temperature. After 12 h, analysis by LCMS showed the reaction was complete. The crude reaction was washed with 0.1 M HCl (100 mL×2). The organic fraction was dried over a pad of magnesium sulfate, filtered and concentrated in vacuo. Fmoc-Thr(Bzl)-Dil-OtBu was isolated by flash chromatography on silica gel (silica gel 40 μm, 60 Å, 3.0×17.0 cm) using 18% to 90% EtOAc in hexanes as the eluent. A total of 3.71 g of Fmoc-Thr(Bzl)-Dil-OtBu (5.51 mmol, 82% yield) was obtained.

To a stirred room temperature solution of Fmoc-Thr(Bzl)-Dil-OtBu (3.71 g, 5.51 mmol) in MeCN (5 mL) was added piperidine (4 mL). After 5 h, analysis by LCMS showed the reaction was complete. The crude reaction mixture was extracted with Hexanes and the MeCN layer was concentrated in vacuo to yield crude H-Thr(Bzl)-Dil-OtBu that was used without further purification.

To a stirred room temperature suspension of crude H-Thr(Bzl)-Dil-OtBu and Dov (1.60 g, 11.0 mmol) in DMF (20 mL) was added DIEA (2.95 mL, 16.5 mmol), followed by HATU (4.19 g, 11.0 mmol). After 6 h, analysis by LCMS showed that the reaction was complete. The crude reaction mixture was diluted with saturated sodium bicarbonate (10 mL) and extracted with EtOAc (40 mL×2). The combined organic fractions were washed with brine, dried over a pad of magnesium sulfate, filtered, and concentrated in vacuo. The crude oil was purified by preparatory RP-HPLC with a Phenomenex Synergi 10μ Max-RP 80 Å column (150×30 mm) using 10% to 90% MeCN in 0.05% aqueous TFA as the eluent. A total of 1.09 g Dov-Ser(Bzl)-Dil-OtBu (1.58 mmol, 29%) was obtained as the TFA salt.

To a room temperature solution of Dov-Thr(Bzl)-Dil-OtBu TFA salt (0.331 g, 0.478 mmol) in $CH_2Cl_2$ (5 mL) was added TFA (4 mL). After 10 h, analysis by LCMS showed the reaction was complete. Volatile organics were evaporated in vacuo to yield crude Dov-Thr(Bzl)-Dil-OH TFA salt that was used without further purification.

To a stirred room temperature suspension of crude Dov-Thr(Bzl)-Dil-OH TFA salt and H-Dap-Phe-OMe TFA salt (0.183 g, 0.526 mmol) in DMF (10 mL) was added DIEA (0.341 mL, 1.92 mmol), followed by HATU (0.364 g, 0.957 mmol). After 24 h, analysis by LCMS showed the reaction was complete. The crude reaction mixture was diluted with saturated sodium bicarbonate (10 mL) and extracted with EtOAc (40 mL×2). The combined organic fractions were washed with brine, dried over a pad of magnesium sulfate, filtered, and concentrated in vacuo. The crude oil was purified by preparatory RP-HPLC with a Phenomenex Synergi 10μ Max-RP 80× column (150×30 mm) using 10% to 90% MeCN in 0.05% aqueous TFA as the eluent. A total of 0.290 g Dov-Thr(Bzl)-Dil-Dap-Phe-OMe (0.300 mmol, 63%) was obtained as the TFA salt.

A stirred room temperature suspension of Dov-Thr(Bzl)-Dil-Dap-Phe-OMe TFA salt (0.290 g, 0.300 mmol) and palladium on activated charcoal (10% Pd basis, 0.232 g) in MeOH (5 mL) was hydrogenated. After 24 h, analysis by LCMS showed the reaction was complete. The crude reaction mixture was filtered over a pad of diatomaceous earth and the filtrate was concentrated. The crude oil was purified by preparatory RP-HPLC with a Phenomenex Synergi Max-RP 80 Å column (150×30 mm) using 10% to 90% MeCN in 0.05% aqueous TFA as the eluent. A total of 0.129 g of the title compound was obtained as the TFA salt (0.147 mmol, 43%). LCMS RT=2.40 min (Method A); ESI-MS m/z 762.75 $[M+H]^+$; HRMS m/z 762.5009 $[C_{40}H_{67}N_5O_9+H]^+$.

Example 3

(S)-2-(dimethylamino)-N—((S)-3-hydroxy-1-(((3R,4S,5S)-3-methoxy-1-((S)-2-((1R,2R)-1-methoxy-2-methyl-3-oxo-3-((2-(pyridin-2-yl)ethyl)amino)propyl)pyrrolidin-1-yl)-5-methyl-1-oxoheptan-4-yl)(methyl)amino)-1-oxopropan-2-yl)-3-methylbutanamide

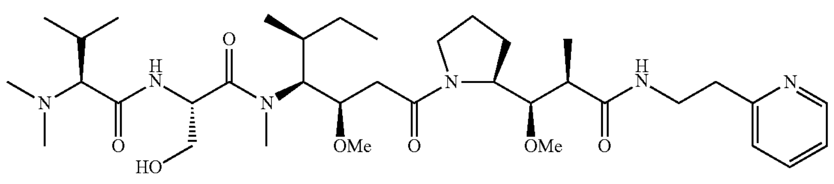 [SMILES: CC[C@H](C)[C@@H]([C@@H](CC(=O)N1CCC[C@H]1[C@H](OC)[C@@H](C)C(=O)NCCc1ccccn1)OC)N(C)C(=O)[C@H](CO)NC(=O)[C@H](C(C)C)N(C)C]

To a stirred room temperature suspension of Boc-Dap-OH dicyclohexylamine salt (10.0 g, 21.4 mmol) and 2-(2-pyridyl)ethylamine (3.83 mL, 32.0 mmol) in $CH_2Cl_2$ (20 mL) was added DIEA (11.4 mL, 64.1 mmol), followed by DEPC (4.83 mL, 32.0 mmol). After overnight stirring, analysis by LCMS showed the reaction was complete. Boc-Dap-2-(2-pyridyl)ethylamine was isolated by flash chromatography on silica gel (silica gel 40 μm, 60 Å, 3.0×17.0 cm) using 2% to 10% MeOH/1% $NEt_3$ in $CH_2Cl_2$ as the eluent. A total of 7.42 g of Boc-Dap-2-(2-pyridyl) ethylamine (19.0 mmol, 89% yield) was obtained.

To a stirred room temperature solution of Boc-Dap-2-(2-pyridyl)ethylamine (7.42 g, 19.0 mmol) in $CH_2Cl_2$ (10 mL) was added TFA (10 mL). After overnight stirring, analysis by LCMS showed the reaction was complete. The crude oil was purified by preparatory RP-HPLC with a Phenomenex Synergi 10 Max-RP 80 Å column (150×30 mm) using 10% to 90% MeCN in 0.05% aqueous TFA as the eluent. A total of 4.50 g H-Dap-(2-pyridyl)ethylamine (11.1 mmol, 59%) was obtained as the TFA salt.

To a room temperature solution of Dov-Ser(Bzl)-Dil-OtBu (0.287 g, 0.423 mmol) in $CH_2Cl_2$ (5 mL) was added TFA (4 mL). After 10 h, analysis by LCMS showed the reaction was complete. Volatile organics were evaporated in vacuo to yield crude Dov-Ser(Bzl)-Dil-OH TFA salt that was used without further purification.

To a stirred room temperature suspension of crude Dov-Ser(Bzl)-Dil-OH TFA salt and H-Dap-2-(2-pyridyl)ethylamine TFA salt (0.136 g, 0.466 mmol) in DMF (10 mL) was added DIEA (0.302 mL, 1.70 mmol) followed by HATU (0.322 g, 0.847 mmol). After 6 h, analysis by LCMS showed the reaction was complete. The crude reaction mixture was diluted with saturated sodium bicarbonate (10 mL) and extracted with EtOAc (40 mL×2). The combined organic fractions were washed with brine, dried over a pad of magnesium sulfate, filtered, and concentrated in vacuo. The crude oil was purified by preparatory RP-HPLC with a Phenomenex Synergi 10 Max-RP 80 Å column (150×30 mm) using 10% to 90% MeCN in 0.05% aqueous TFA as the eluent. A total of 0.258 g Dov-Ser(Bzl)-Dil-Dap-2-(2-pyridyl)ethylamine (0.288 mmol, 68%) was obtained as the TFA salt.

A stirred room temperature suspension of Dov-Ser(Bzl)-Dil-Dap-2-(2-pyridyl)ethylamine TFA salt (0.258 g, 0.330 mmol), ammonium formate (0.062 g, 0.991 mmol), and palladium on activated charcoal (10% Pd basis, 0.100 g) in MeOH (5 mL) was hydrogenated. After 12 h, analysis by LCMS showed the reaction was complete. The crude reaction mixture was filtered over a pad of diatomaceous earth and the filtrate was concentrated.

The crude oil was purified by preparatory RP-HPLC with a Phenomenex Synergi 10p Max-RP 80 Å column (150×30 mm) using 10% to 90% MeCN in 0.05% aqueous TFA as the eluent. A total of 0.014 g of the title compound was obtained as the TFA salt (0.017 mmol, 5%). LCMS RT=1.76 min (Method A); ESI-MS m/z 691.56 $[M+H]^+$; HRMS m/z 691.4755 $[C_{36}H_{62}N_6O_7+H]^+$.

Example 4

(2S,3R)-2-((S)-2-(dimethylamino)-3-methylbutanamido)-3-hydroxy-N-((3R,4S,5S)-3-methoxy-1-((S)-2-((1R,2R)-1-methoxy-2-methyl-3-oxo-3-((2-(pyridin-2-yl)ethyl)amino)propyl)pyrrolidin-1-yl)-5-methyl-1-oxoheptan-4-yl)-N-methylbutanamide

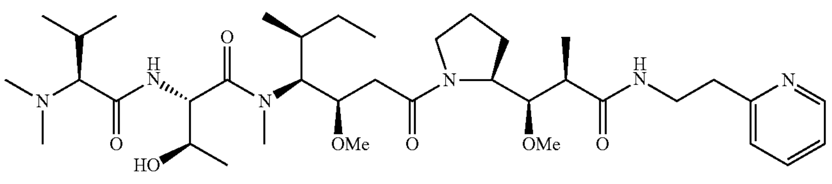 [SMILES: CC[C@H](C)[C@@H]([C@@H](CC(=O)N1CCC[C@H]1[C@H](OC)[C@@H](C)C(=O)NCCc1ccccn1)OC)N(C)C(=O)[C@@H](NC(=O)[C@H](C(C)C)N(C)C)[C@@H](C)O]

To a room temperature solution of Dov-Thr(Bzl)-Dil-OtBu (0.357 g, 0.618 mmol) in $CH_2Cl_2$ (5 mL) was added TFA (4 mL). After 10 h, analysis by LCMS showed the reaction was complete. Volatile organics were evaporated in vacuo to yield crude Dov-Thr(Bzl)-Dil-OH TFA salt that was used without further purification.

To a stirred room temperature suspension of crude Dov-Thr(Bzl)-Dil-OH TFA salt and H-Dap-2-(2-pyridyl)ethylamine TFA salt (0.198 g, 0.680 mmol) in DMF (10 mL) was added DIEA (0.441 mL, 2.47 mmol), followed by HATU (0.470 g, 1.24 mmol) and HOBt (0.189 g, 1.24 mmol). After 6 h, analysis by LCMS showed the reaction was complete. The crude reaction mixture was diluted with saturated sodium bicarbonate (10 mL) and extracted with EtOAc (40 mL×2). The combined organic fractions were washed with brine, dried over a pad of magnesium sulfate, filtered, and concentrated in vacuo. The crude oil was purified by preparatory RP-HPLC with a Phenomenex Synergi 10 μL Max-RP 80 Å column (150×30 mm) using 10% to 90% MeCN in 0.05% aqueous TFA as the eluent. A total of 0.356 g Dov-Thr(Bzl)-Dil-Dap-2-(2-pyridyl)ethylamine (0.392 mmol, 63%) was obtained as the TFA salt.

A stirred room temperature suspension of Dov-Thr(Bzl)-Dil-Dap-2-(2-pyridyl)ethylamine TFA salt (0.356 g, 0.392 mmol), ammonium formate (0.085 g, 1.35 mmol), and palladium on activated charcoal (10% Pd basis, 0.175 g) in MeOH (5 mL) was hydrogenated. After 12 h, analysis by LCMS showed the reaction was complete. The crude reaction mixture was filtered over a pad of diatomaceous earth and the filtrate was concentrated. The crude oil was purified by preparatory RP-HPLC with a Phenomenex Synergi 10p Max-RP 80 Å column (150×30 mm) using 10% to 90% MeCN in 0.05% aqueous TFA as the eluent. A total of 0.010 g of the title compound was obtained as the TFA salt (0.012 mmol, 3%). LCMS RT=1.72 min (Method A); ESI-MS m/z 705.56 $[M+H]^+$; 728.33 $[M+Na]^+$; HRMS m/z 705.4917 $[C_{37}H_{64}N_6O_7+H]^+$.

Example 5

(2S)-2-(dimethylamino)-N-((2S)-3-hydroxy-1-(((3R,4S,5S)-3-methoxy-1-((2S)-2-((1R,2R)-1-methoxy-2-methyl-3-oxo-3-((2-(piperidin-2-yl)ethyl)amino)propyl)pyrrolidin-1-yl)-5-methyl-1-oxoheptan-4-yl)(methyl)amino)-1-oxopropan-2-yl)-3-methylbutanamide

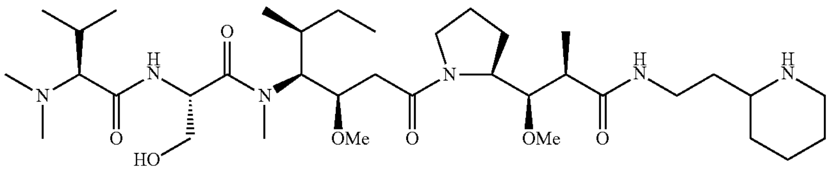 [SMILES: CC[C@H](C)[C@@H]([C@@H](CC(=O)N1CCC[C@H]1[C@H](OC)[C@@H](C)C(=O)NCCC1CCCCN1)OC)N(C)C(=O)[C@H](CO)NC(=O)[C@H](C(C)C)N(C)C]

The title compound was obtained as a byproduct of the hydrogenation step in Example 3. A total of 0.010 g of the title compound was obtained as the TFA salt (0.001 mmol). LCMS RT=1.83 min (Method A); ESI-MS m/z 697.76 $[M+H]^+$; HRMS m/z 697.5226 $[C_{36}H_{68}N_6O_7+H]^+$.

Example 6

(2S,3R)-2-((S)-2-(dimethylamino)-3-methylbutanamido)-3-hydroxy-N-((3R,4S,5S)-3-methoxy-1-((2S)-2-((1R,2R)-1-methoxy-2-methyl-3-oxo-3-((2-(piperidin-2-yl)ethyl)amino)propyl)pyrrolidin-1-yl)-5-methyl-1-oxoheptan-4-yl)-N-methylbutanamide

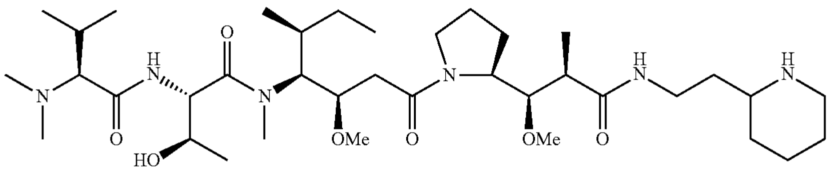 [SMILES: CC[C@H](C)[C@@H]([C@@H](CC(=O)N1CCC[C@H]1[C@H](OC)[C@@H](C)C(=O)NCCC1CCCCN1)OC)N(C)C(=O)[C@@H](NC(=O)[C@H](C(C)C)N(C)C)[C@@H](C)O]

The title compound was obtained as a byproduct of the hydrogenation step in Example 4. A total of 0.010 g of the title compound was obtained as the TFA salt (0.012 mmol). LCMS RT=1.81 min (Method A); ESI-MS m/z 711.43 $[M+H]^+$; HRMS m/z 711.5389 $[C_{37}H_{70}N_6O_7+H]^+$.

Example 7

(S)-methyl 2-((2R,3R)-3-((S)-1-((3R,4S,5S)-4-((2S, 3S)-3-azido-2-((S)-2-(dimethylamino)-3-methylbutanamido)-N-methylbutanamido)-3-methoxy-5-methylheptanoyl)pyrrolidin-2-yl)-3-methoxy-2-methylpropanamido)-3-phenylpropanoate

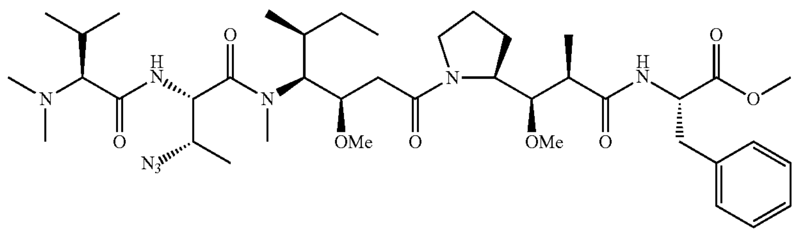 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@H](C(C)C)N(C)C)[C@H](C)N=[N+]=[N-]]

To a stirred room temperature solution of (2S,3S)-Fmoc-Abu(3-$N_3$)—OH (1.00 g, 2.74 mmol) and H-Dil-OtBu hydrochloride (0.810 g, 2.74 mmol) in EtOAc (10 mL) was added DIEA (0.880 mL, 4.93 mmol). The solution was cooled (0° C.) and stirred for 20 min. DIEA (0.880 mL, 4.93 mmol) was added to the reaction mixture. The solution was cooled (0° C.) and stirred for 20 min. CMPI (1.12 g, 4.38 mmol) was added to the reaction mixture and the reaction mixture was allowed to reach room temperature. After 12 h, analysis by LCMS showed the reaction was complete. The crude reaction was washed with 0.1 M HCl (100 mL×2), followed by brine (20 mL×2). The organic fraction was dried over a pad of magnesium sulfate, filtered, and concentrated in vacuo to yield crude Fmoc-Abu(3-$N_3$)-Dil-OtBu (1.12 g, 1.84 mmol) that was used without further purification.

To a stirred room temperature solution of Fmoc-Abu(3-$N_3$)-Dil-OtBu (1.00 g, 1.65 mmol) in MeCN (10 mL) was added piperidine (2 mL). After 5 h, analysis by LCMS showed the reaction was complete. To the crude reaction mixture was extracted with Hexanes and the MeCN layer was concentrated in vacuo to yield crude H-Abu(3-$N_3$)-Dil-OtBu that was used without further purification.

To a stirred room temperature suspension of crude H-Abu (3-$N_3$)-Dil-OtBu and Dov (0.478 g, 3.29 mmol) in DMF (10 mL) was added DIEA (0.880 mL, 4.94 mmol), followed by HATU (1.25 g, 3.29 mmol). After 6 h, analysis by LCMS showed that the reaction was complete. The crude reaction mixture was diluted with saturated sodium bicarbonate (10 mL) and extracted with EtOAc (40 mL×2). The combined organic fractions were washed with brine, dried over a pad of magnesium sulfate, filtered, and concentrated in vacuo. The crude oil was purified by preparatory RP-HPLC with a Phenomenex Synergi 10p Max-RP 80 Å column (150×30 mm) using 10% to 90% MeCN in 0.05% aqueous TFA as the eluent. A total of 0.670 g Dov-Abu(3-$N_3$)-Dil-OtBu (1.07 mmol, 65%) was obtained as the TFA salt.

To a room temperature solution of Dov-Abu(3-$N_3$)-Dil-OtBu TFA salt (0.289 g, 0.425 mmol) in $CH_2Cl_2$ (5 mL) was added TFA (5 mL). After 12 h, analysis by LCMS showed the reaction was complete. Volatile organics were evaporated in vacuo to yield crude Dov-Abu(3-$N_3$)-Dil-OH TFA salt that was used without further purification.

To a stirred room temperature suspension of crude Dov-Abu(3-$N_3$)-Dil-OH TFA salt (1.04 g, 1.82 mmol) and H-Dap-Phe-OMe TFA salt (1.59 g, 3.44 mmol) in DMF (10 mL) was added DIEA (1.18 g, 1.60 mL, 9.11 mmol), followed by the addition of HATU (1.74 g, 4.56 mmol). After 10 h, analysis by LCMS showed the reaction was complete. The crude reaction mixture was diluted with saturated sodium bicarbonate (10 mL) and extracted with EtOAc (20 mL×3). The combined organic fractions were washed with brine, dried over a pad of magnesium sulfate, filtered, and concentrated in vacuo. The crude oil was purified by preparatory RP-HPLC with a Phenomenex Gemini NX-C18 10μ 110 Å column (150×30 mm) using 10% to 90% MeCN in 0.1% aqueous formic acid. A total of 935 mg of the title compound was obtained as the formic acid salt (1.12 mmol, 49%). LCMS RT=1.09 min (Method A); ESI-MS m/z 787.53 $[M+H]^+$; HRMS m/z 787.5072 $[C_{40}H_{66}N_8O_8+H]^+$.

Example 8

(S)-methyl 2-((2R,3R)-3-((S)-1-((3R,4S,5S)-4-((S)-3-amino-2-((S)-2-(dimethylamino)-3-methylbutanamido)-N-methylpropanamido)-3-methoxy-5-methylheptanoyl)pyrrolidin-2-yl)-3-methoxy-2-methylpropanamido)-3-phenylpropanoate

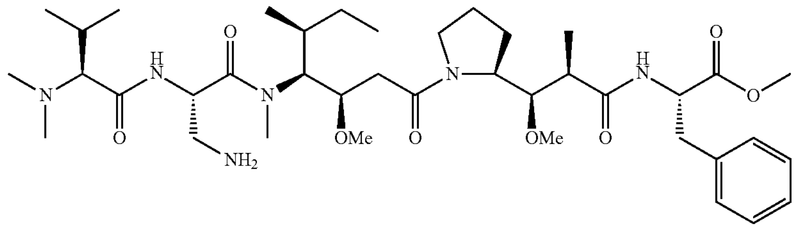 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@H](CN)NC(=O)[C@H](C(C)C)N(C)C]

To a stirred room temperature solution of Fmoc-Dpr(Boc)-OH (1.44 g, 3.38 mmol) and H-Dil-OtBu hydrochloride (1.00 g, 3.38 mmol) in EtOAc (10 mL) was added DIEA (1.08 mL, 6.08 mmol). The solution was cooled to (0° C.) and stirred for 20 min. Additional DIEA (1.08 mL, 6.08 mmol) was added to the reaction mixture and the 0° C. solution was stirred for 20 min. CMPI (1.38 g, 5.41 mmol) was then added to the reaction mixture and the reaction mixture was allowed to warm to room temperature. After 12 h, analysis by LCMS showed the reaction was complete. The crude reaction was washed with 0.1 M HCl (100 mL×2), followed by brine (20 mL×2). The organic fraction was dried over a pad of magnesium sulfate, filtered, and concentrated in vacuo. Fmoc-Dpr(Boc)-Dil-OtBu was isolated by flash chromatography on silica gel (silica gel 40 μm, 60 Å, 3.0×17.0 cm) using 18% to 90% EtOAc in Hexanes as the eluent. A total of 1.27 g of Fmoc-Dpr(Boc)-Dil-OtBu (1.90 mmol, 56% yield) was obtained.

To a stirred room temperature solution Fmoc-Dpr(Boc)-Dil-OtBu (1.27 g, 1.90 mmol) in MeCN (10 mL) was added piperidine (2 mL). After 5 h, analysis by LCMS showed the reaction was complete. The crude reaction mixture was extracted with hexanes and the MeCN layer was concentrated in vacuo to yield crude H-Dpr(Boc)-Dil-OtBu that was used without further purification.

To a stirred room temperature suspension of crude H-Dpr(Boc)-Dil-OtBu and Dov (0.552 g, 3.80 mmol) in DMF (10 mL) was added DIEA (1.02 mL, 5.70 mmol), followed by HATU (1.45 g, 3.80 mmol). After 6 h, analysis by LCMS showed that the reaction was complete. The crude reaction mixture was diluted with saturated sodium bicarbonate (10 mL) and extracted with EtOAc (40 mL×2). The combined organic fractions were washed with brine, dried over a pad of magnesium sulfate, filtered, and concentrated in vacuo. The crude oil was purified by preparatory RP-HPLC with a Phenomenex Synergi 10p Max-RP 80 Å column (150×30 mm) using 10% to 90% MeCN in 0.05% aqueous TFA as the eluent. A total of 0.598 g Dov-Dpr(Boc)-Dil-OtBu (0.871 mmol, 46%) was obtained as the TFA salt.

To a room temperature solution Dov-Dpr(Boc)-Dil-OtBu TFA salt (1.52 g, 2.65 mmol) in $CH_2Cl_2$ (10 mL) was added TFA (5 mL). After 10 h, analysis by LCMS showed the reaction was complete. Volatile organics were evaporated in vacuo to yield crude Dov-Dpr-Dil-OH TFA salt that was used without further purification.

To a stirred room temperature suspension of Dov-Dpr-Dil-OH TFA salt (1.00 g, 1.89 mmol) and Fmoc-OSu (0.891 g, 2.64 mmol) in $CH_2C_2$ (10 mL) was added DIEA (0.460 mL, 2.64 mmol). After 12 h, analysis by LCMS showed the reaction was complete. Volatile organics were evaporated in vacuo. The crude oil was purified by preparatory RP-HPLC with a Phenomenex Synergi 10 Max-RP 80 Å column (150×30 mm) using 10% to 90% MeCN in 0.1% aqueous formic acid as the eluent. A total of 1.49 g of enriched Dov-Dpr(Fmoc)-Dil-OH was obtained as the formic acid salt.

To a stirred 23° C. suspension of Dov-Dpr(Fmoc)-Dil-OH formic acid salt (1.20 g, 1.75 mmol) and H-Dap-Phe-OMe TFA salt (0.982 g, 2.13 mmol) in DMF (10 mL) was added DIEA (0.970 g, 1.30 mL, 7.514 mmol) followed by the addition of HATU (1.43 g, 3.76 mmol). After 10 h, analysis by LCMS showed the reaction was complete. The crude reaction was diluted with saturated sodium bicarbonate (10 mL) and extracted with EtOAc (20 mL×3). The combined organic fractions were washed with brine, dried over a pad of magnesium sulfate, filtered, and concentrated in vacuo. The crude oil was purified by preparatory RP-HPLC with a Phenomenex Gemini NX-C18 10μ 110 Å column (150×30 mm) using 10% to 90% MeCN in 0.1% aqueous $NH_4OH$ as the eluent. A total of 1.01 g of Dov-Dpr(Fmoc)-Dil-Dap-Phe-OMe (1.04 mmol, 56%) was obtained.

To a stirred 23° C. solution of Dov-Dpr(Fmoc)-Dil-Dap-Phe-OMe (1.01 g, 1.04 mmol) in acetonitrile (10 mL) was added piperidine (5 mL). After 3 h, analysis by LCMS showed the reaction was complete. To the crude reaction solution was added hexanes. The acetonitrile layer was concentrated in vacuo. The crude oil was purified by preparatory RP-HPLC with a Phenomenex Gemini NX-C18 10μ 110 Å column (150×30 mm) using 5% to 95% MeCN in 0.1% aqueous formic acid as the eluent. A total of 413 g of the title compound was obtained as the formic acid salt (0.521 mmol, 50%). LCMS RT=2.10 min (Method A); ESI-MS m/z 747.84 $[M+H]^+$; HRMS m/z 747.5008 $[C_{39}H_{66}N_6O_8+H]^+$.

Example 9

(S)—N—((S)-3-amino-1-(((3R,4S,5S)-3-methoxy-1-((S)-2-((1R,2R)-1-methoxy-2-methyl-3-oxo-3-((2-(pyridin-2-yl)ethyl)amino)propyl)pyrrolidin-1-yl)-5-methyl-1-oxoheptan-4-yl)(methyl)amino)-1-oxopropan-2-yl)-2-(dimethylamino)-3-methylbutanamide

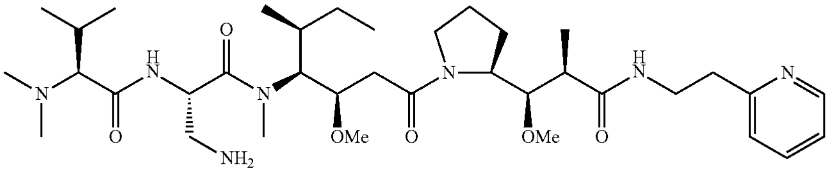 [SMILES: CC[C@H](C)[C@@H]([C@@H](CC(=O)N1CCC[C@H]1[C@H](OC)[C@@H](C)C(=O)NCCc1ccccn1)OC)N(C)C(=O)[C@H](CN)NC(=O)[C@H](C(C)C)N(C)C]

To a stirred room temperature suspension of crude Dov-Dpr(Fmoc)-Dil-OH and H-Dap-2-(2-pyridyl)ethylamine TFA salt (0.230 g, 0.789 mmol) in DMF (10 mL) was added DIEA (0.511 mL, 2.87 mmol), followed by HATU (0.545 g, 1.43 mmol). After 6 h, analysis by LCMS showed the reaction was complete. The crude reaction mixture was diluted with saturated sodium bicarbonate (10 mL) and extracted with EtOAc (25 mL×3). The combined organic fractions were washed with brine, dried over a pad of magnesium sulfate, filtered, and concentrated in vacuo. The crude oil was purified by preparatory RP-HPLC with a Phenomenex Synergi 10μ. Max-RP 80 Å column (150×30 mm) using 10% to 90% MeCN in 0.05% aqueous TFA as the eluent. A total of 0.150 g of Dov-Dpr(Fmoc)-Dil-Dap-2-(2-pyridyl)ethylamine was obtained as the TFA salt (0.146 mmol, 20%).

To a stirred room temperature solution Dov-Dpr(Fmoc)-Dil-Dap-2-(2-pyridyl)ethylamine TFA salt (0.150 g, 0.146 mmol) in MeCN (10 mL) was added piperidine (2 mL). After 5 h, analysis by LCMS showed the reaction was complete. The crude reaction mixture was extracted with hexanes and the MeCN layer was concentrated in vacuo. The crude oil was purified by preparatory RP-HPLC with a Phenomenex Synergi 10μ Max-RP 80 Å column (150×30 mm) using 10% to 90% MeCN in 0.05% aqueous TFA as the eluent. A total of 0.089 g of the title compound was obtained as the TFA salt (0.111 mmol, 75%). LCMS RT=1.52 min (Method A); ESI-MS m/z 690.67 $[M+H]^+$; HRMS m/z 690.4917 $[C_{36}H_{63}N_7O_6+H]^+$.

Example 10

(S)-methyl 2-((2R,3R)-3-((S)-1-((3R,4S,5S)-4-((S)-3-azido-2-((S)-2-(dimethylamino)-3-methylbutanamido)-N-methylpropanamido)-3-methoxy-5-methylheptanoyl)pyrrolidin-2-yl)-3-methoxy-2-methylpropanamido)-3-phenylpropanoate

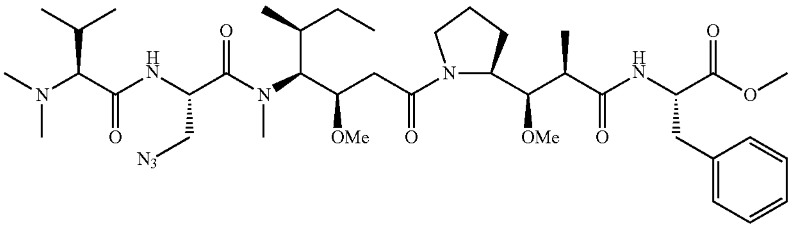 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@H](CN=[N+]=[N-])NC(=O)[C@H](C(C)C)N(C)C]

To a stirred room temperature solution of N-Boc-4-Azido-Alanine dicyclohexylamine salt (1.02 g, 2.47 mmol) and H-Dil-OtBu hydrochloride (0.730 g, 2.74 mmol) in EtOAc (10 mL) was added DIEA (0.792 mL, 4.44 mmol). The solution was cooled (0° C.) and stirred for 20 min. DIEA (0.792 mL, 4.44 mmol) was added to the reaction mixture. The solution was cooled (0° C.) and stirred for 20 min. CMPI (1.01 g, 3.95 mmol) was added to the reaction mixture and the reaction mixture was allowed to reach room temperature. After 12 h, analysis by LCMS showed the reaction was complete. The crude reaction was washed with 0.1 M HCl (100 mL×2), followed by brine (20 mL×2). The organic fraction was dried over a pad of magnesium sulfate, filtered, and concentrated in vacuo to yield crude N-Boc-4-Azido-Ala-Dil-OtBu (1.08 g, 2.29 mmol) that was used without further purification.

To a room temperature solution of N-Boc-4-Azido-Ala-Dil-OtBu (1.08 g, 2.29 mmol) in $CH_2Cl_2$ (5 mL) was added TFA (3 mL). After 10 h, analysis by LCMS showed the reaction was complete. Volatile organics were evaporated in vacuo to yield crude H-4-Azido-Ala-Dil-OH TFA salt that was used without further purification.

To a stirred room temperature suspension of Dov (0.739 g, 5.09 mmol) in DMF (10 mL) was added DIEA (1.36 mL, 7.63 mmol), followed by HATU (1.95 g, 5.09 mmol). After 10 min crude H-4-Azido-Ala-Dil-OH was added to the reaction mixture. After 6 h, analysis by LCMS showed that the reaction was complete. The crude oil was purified by preparatory RP-HPLC with a Phenomenex Synergi 10 Max-RP 80 Å column (150×30 mm) using 10% to 90% MeCN in 0.05% aqueous TFA as the eluent. A total of 0.130 g Dov-4-Azido-Ala-Dil-OH (0.261 mmol, 10%) was obtained as the TFA salt.

To a stirred room temperature suspension of Dov-4-Azido-Ala-Dil-OH TFA salt (0.130 g, 0.261) and H-Dap-Phe-OMe TFA salt (0.205 g, 0.588 mmol) in DMF (10 mL) was added DIEA (0.140 mL, 0.783 mmol), followed by HATU (0.198 g, 0.522 mmol). After 6 h, analysis by LCMS showed the reaction was complete. The crude reaction mixture was diluted with saturated sodium bicarbonate (10 mL) and extracted with EtOAc (40 mL×2). The combined organic fractions were washed with brine, dried over a pad of magnesium sulfate, filtered, and concentrated in vacuo. The crude oil was purified by preparatory RP-HPLC with a Phenomenex Synergi 10 Max-RP 80 Å column (150×30 mm) using 10% to 90% MeCN in 0.05% aqueous TFA as the eluent. A total of 0.015 g of the title compound was obtained as the TFA salt (0.017 mmol, 7%). LCMS RT=2.36 min (Method A); ESI-MS m/z 773.48 $[M+H]^+$; HRMS m/z 773.4916 $[C_{39}H_{64}N_8O_8+H]^+$.

Example 11

(S)-methyl 2-((2R,3R)-3-((S)-1-((3R,4S,5S)-4-((S)-4-azido-2-((S)-2-(dimethylamino)-3-methylbutanamido)-N-methylbutanamido)-3-methoxy-5-methylheptanoyl)pyrrolidin-2-yl)-3-methoxy-2-methylpropanamido)-3-phenylpropanoate

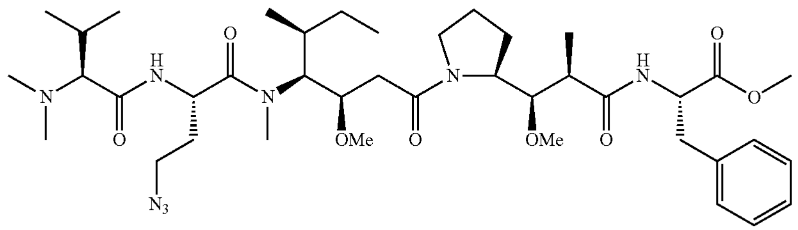 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@H](CCN=[N+]=[N-])NC(=O)[C@H](C(C)C)N(C)C]

To a stirred room temperature solution of N-Boc-4-Azido-homoalanine dicyclohexylamine salt (1.01 g, 2.37 mmol) and H-Dil-OtBu hydrochloride (0.700 g, 2.37 mmol) in EtOAc (10 mL) was added DIEA (0.759 mL, 4.26 mmol). The solution was cooled (0° C.) and stirred for 20 min. DIEA (0.759 mL, 4.26 mmol) was added to the reaction mixture. The solution was cooled (0° C.) and stirred for 20 min. CMPI (0.967 g, 3.79 mmol) was added to the reaction mixture and the reaction mixture was allowed to reach room temperature. After 12 h, analysis by LCMS showed the reaction was complete. The crude reaction was washed with 0.1 M HCl (100 mL×2), followed by brine (20 mL×2). The organic fraction was dried over a pad of magnesium sulfate, filtered, and concentrated in vacuo to yield crude N-Boc-4-Azido-homoAla-Dil-OtBu (1.09 g, 2.25 mmol) that was used without further purification.

To a room temperature solution of N-Boc-4-Azido-homoAla-Dil-OtBu (1.09 g, 2.25 mmol) in $CH_2Cl_2$ (5 mL) was added TFA (3 mL). After 10 h, analysis by LCMS showed the reaction was complete. Volatile organics were evaporated in vacuo to yield crude H-4-Azido-homoAla-Dil-OH TFA salt that was used without further purification.

To a stirred room temperature suspension of Dov (0.652 g, 4.49 mmol) in DMF (10 mL) was added DIEA (1.20 mL, 6.73 mmol), followed by HATU (1.71 g, 4.49 mmol). After 10 min crude H-4-Azido-homoAla-Dil-OH TFA salt was added to the reaction mixture. After 6 h, analysis by LCMS showed that the reaction was complete. The crude oil was purified by preparatory RP-HPLC with a Phenomenex Synergi 10μ Max-RP 80 Å column (150×30 mm) using 10% to 90% MeCN in 0.05% aqueous TFA as the eluent. A total of 0.127 g Dov-4-Azido-homoAla-Dil-OH (0.223 mmol, 10%) was obtained as the TFA salt.

To a stirred room temperature suspension of Dov-4-Azido-homoAla-Dil-OH TFA salt (0.127 g, 0.223) and H-Dap-Phe-OMe TFA salt (0.198 g, 0.568 mmol) in DMF (10 mL) was added DIEA (0.140 mL, 0.783 mmol), followed by HATU (0.198 g, 0.522 mmol). After 6 h, analysis by LCMS showed the reaction was complete. The crude reaction mixture was diluted with saturated sodium bicarbonate (10 mL) and extracted with EtOAc (40 mL×2). The combined organic fractions were washed with brine, dried over a pad of magnesium sulfate, filtered, and concentrated in vacuo. The crude oil was purified by preparatory RP-HPLC with a Phenomenex Synergi 10 Max-RP 80 Å column (150×30 mm) using 10% to 90% MeCN in 0.05% aqueous TFA as the eluent. A total of 0.015 g of the title compound was obtained as the TFA salt (0.017 mmol, 7%). LCMS RT=2.38 min (Method A); ESI-MS m/z 787.49 $[M+H]^+$; HRMS m/z 787.5078 $[C_{40}H_{66}N_8O_8+H]^+$.

Example 12

(S)-methyl 2-((2R,3R)-3-((S)-1-((3R,4S,5S)-4-((S)-4-amino-2-((S)-2-(dimethylamino)-3-methylbutanamido)-N-methylbutanamido)-3-methoxy-5-methylheptanoyl)pyrrolidin-2-yl)-3-methoxy-2-methylpropanamido)-3-phenylpropanoate

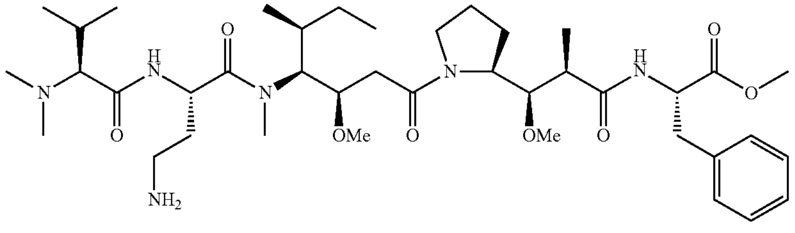 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@H](CCN)NC(=O)[C@H](C(C)C)N(C)C]

To a stirred room temperature solution of Fmoc-Dab(Boc)-OH (1.54 g, 3.38 mmol) and H-Dil-OtBu hydrochloride (1.00 g, 3.38 mmol) in EtOAc (10 mL) was added DIEA (1.08 mL, 6.08 mmol). The solution was cooled (0° C.) and stirred for 20 min. Additional DIEA (1.08 mL, 6.08 mmol) was added to the reaction mixture, and the 0° C. solution was stirred for 20 min. Then CMPI (1.38 g, 5.41 mmol) was added to the reaction mixture and the reaction mixture was allowed to warm to room temperature. After 12 h, analysis by LCMS showed the reaction was complete. The crude reaction was washed with 0.1 M HCl (100 mL×2), followed by brine (20 mL×2). The organic fraction was dried over a pad of magnesium sulfate, filtered, and concentrated in vacuo. Fmoc-Dab(Boc)-Dil-OtBu was isolated by flash chromatography on silica gel (silica gel 40 μm, 60 Å, 3.0×17.0 cm) using 18% to 90% EtOAc in hexanes as the eluent. A total of 1.18 g of Fmoc-Dpr(Boc)-Dil-OtBu (1.73 mmol, 51% yield) was obtained.

To a stirred room temperature solution Fmoc-Dab(Boc)-Dil-OtBu (1.18 g, 1.73 mmol) in MeCN (10 mL) was added piperidine (2 mL). After 5 h, analysis by LCMS showed the reaction was complete. The crude reaction mixture was extracted with Hexanes and the MeCN layer was concentrated in vacuo to yield crude H-Dab(Boc)-Dil-OtBu that was used without further purification.

To a stirred room temperature suspension of crude H-Dab(Boc)-Dil-OtBu and Dov (0.502 g, 3.46 mmol) in DMF (10 mL) was added DIEA (0.925 mL, 5.19 mmol), followed by HATU (1.32 g, 3.46 mmol). After 6 h, analysis by LCMS showed that the reaction was complete. The crude reaction mixture was diluted with saturated sodium bicarbonate (10 mL) and extracted with EtOAc (40 mL×2). The combined organic fractions were washed with brine, dried over a pad of magnesium sulfate, filtered, and concentrated in vacuo. The crude oil was purified by preparatory RP-HPLC with a Phenomenex Synergi 10μ Max-RP 80 Å column (150×30 mm) using 10% to 90% MeCN in 0.05% aqueous TFA as the eluent. A total of 0.410 g of Dov-Dab(Boc)-Dil-OtBu (0.583 mmol, 34%) was obtained as the TFA salt.

To a room temperature solution Dov-Dab(Boc)-Dil-OtBu TFA salt (0.240 g, 0.419 mmol) in $CH_2Cl_2$ (5 mL) was added TFA (2 mL). After 10 h, analysis by LCMS showed the reaction was complete. Volatile organics were evaporated in vacuo to yield crude Dov-Dab-Dil-OH TFA salt that was used without further purification.

To a stirred room temperature suspension of Dov-Dab-Dil-OH TFA salt (0.175 g, 0.406 mmol) and Fmoc-OSu (0.151 g, 0.447 mmol) in $CH_2Cl_2$ (5 mL) was added DIEA (0.080 mL, 0.447 mmol). After 12 h, analysis by LCMS showed the reaction was complete. Volatile organics were evaporated in vacuo. The crude reaction mixture was dissolved in EtOAc and was washed with 0.1 M HCl (100 mL×2), followed by brine (20 mL×2). The organic fraction was dried over a pad of magnesium sulfate, filtered, and concentrated in vacuo to yield crude Dov-Dab(Fmoc)-Dil-OH that was used without further purification.

To a stirred room temperature suspension of crude Dov-Dab(Fmoc)-Dil-OH (0.363 g, 0.556 mmol) and H-Dap-Phe-OMe TFA salt (0.194 g, 0.420 mmol) in DMF (10 mL) was added DIEA (0.291 mL, 1.67 mmol), followed by HATU (0.424 g, 1.11 mmol). After 10 h, analysis by LCMS showed the reaction was complete. The crude reaction mixture was diluted with saturated sodium bicarbonate (10 mL) and extracted with EtOAc (30 mL×2). The combined organic fractions were washed with brine, dried over a pad of magnesium sulfate, filtered, and concentrated in vacuo. The crude oil was purified by preparatory RP-HPLC with a Phenomenex Synergi 10 Max-RP 80 Å column (150×30 mm) using 10% to 90% MeCN in 0.2% aqueous formic acid as the eluent. A total of 449 mg of enriched Dov-Dab(Fmoc)-Dil-Dap-Phe-OMe was obtained as the formic acid salt.

To a stirred room temperature solution enriched Dov-Dab(Fmoc)-Dil-Dap-Phe-OMe formic acid salt (0.449 g) in MeCN (10 mL) was added piperidine (5 mL). After 10 h, analysis by LCMS showed the reaction was complete. The crude reaction mixture was extracted with hexanes and the MeCN layer was concentrated in vacuo. The crude oil was purified by RP-HPLC with a Phenomenex Gemini NX C18 10μ Max-RP 110 Å column (150×30 mm) using 10% to 90% MeCN in 0.1% aqueous formic acid as the eluent. A total of 43.0 g of the title compound was obtained as the formic acid salt (0.053 mmol, 13%). LCMS RT=1.24 min (Method B); ESI-MS m/z 761.57 $[M+H]^+$; HRMS m/z 761.5165 $[C_{40}H_{68}N_6O_8+H]^+$.

Example 13

(S)-2-((S)-2-(aminooxy)-3-methylbutanamido)-N-((3R,4S,5S)-3-methoxy-1-((S)-2-((1R,2R)-1-methoxy-2-methyl-3-oxo-3-((2-(pyridin-2-yl)ethyl)amino)propyl)pyrrolidin-1-yl)-5-methyl-1-oxoheptan-4-yl)-N,3-dimethylbutanamide

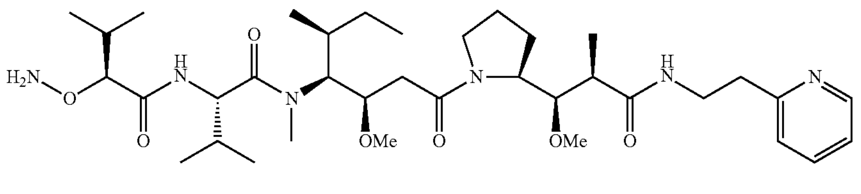 [SMILES: CC[C@H](C)[C@@H]([C@@H](CC(=O)N1CCC[C@H]1[C@H](OC)[C@@H](C)C(=O)NCCc1ccccn1)OC)N(C)C(=O)[C@@H](NC(=O)[C@@H](ON)C(C)C)C(C)C]

To a solution of H-Dil-OtBu hydrochloride (0.60 g, 2.03 mmol) and Fmoc-Val-OH (0.829 g, 2.44 mmol) stirring in EtOAc (3 mL) was added DIEA (0.65 mL, 3.7 mmol). The reaction was cooled to 0° C. and stirred for 20 min, followed by addition of DIEA (0.65 mL, 3.7 mmol). The reaction mixture was cooled (0° C.) for another 20 min, followed by the addition of CMPI (0.83 g, 3.7 mmol). After 8 h, analysis by LCMS showed the reaction was complete. The reaction mixture was washed with 1 M HCl (25 mL×2) and brine (50 mL). The organic phase was dried over magnesium sulfate, filtered, and concentrated in vacuo. Fmoc-Val-Dil-OtBu was isolated by flash chromatography on silica gel (silica gel 40 m, 60 Å, 3.0×17.0 cm) using 18% to 90% EtOAc in hexanes as the eluent. A total of 1.1 g of Fmoc-Val-Dil-OtBu (1.9 mmol, 93% yield) was obtained.

To a stirred room temperature suspension of Fmoc-Val-Dil-OtBu (0.883 g, 1.52 mmol) and Boc-Dap-2-(2-pyridyl) ethylamine (0.451 g, 1.52 mmol) in $CH_2C_2$ (10 mL) was added TFA (5 mL). After 8 h, analysis by LCMS showed the reaction was complete. Volatile organics were evaporated in vacuo to yield crude Fmoc-Val-Dil-OH and H-Dap-2-(2-pyridyl)ethylamine TFA salt, which were used without further purification.

To a stirred room temperature suspension of crude H-Dap-2-(2-pyridyl)ethylamine TFA salt and Fmoc-Val-Dil-OH in EtOAc (2 mL) was added DIEA (1.10 mL, 6.08 mmol), followed by DEPC (0.92 mL, 6.08 mmol). After 15 h, analysis by LCMS showed the reaction was complete. The reaction was washed with a saturated $NaHCO_3$ solution (50 mL) followed by water (50 mL×2). The organic fraction was filtered through a pad of magnesium sulfate and concentrated in vacuo. The resulting viscous oil was purified by flash chromatography on silica gel (silica gel 40 µm, 60 Å, 23×123 mm) using 5% to 10% MeOH in $CH_2Cl_2$ as the eluent. A total of 0.888 g of Fmoc-Val-Dil-Dap-2-(2-pyridyl) ethylamine (1.11 mmol, 73% yield) was obtained.

To a stirred room temperature solution of Fmoc-Val-Dil-Dap-2-(2-pyridyl)ethylamine (1.75 g, 2.19 mmol) in $CH_2Cl_2$ (5 mL) was added piperidine (5 mL). After 8 h, analysis by LCMS showed the reaction was complete. Volatile organics were evaporated in vacuo to yield crude H-Val-Dil-Dap-2-(2-pyridyl)ethylamine that was used without further purification.

To a stirred room temperature suspension of crude H-Val-Dil-Dap-2-(2-pyridyl)ethylamine and N-Boc-N-hydroxy-Val-OH (0.390 g, 1.67 mmol) in DMF (5 mL) was added DIEA (0.797 mL, 5.02 mmol), followed by HATU (1.28 g, 3.34 mmol). After 8 h, analysis by LCMS showed that the reaction was complete. The crude reaction mixture was diluted with saturated sodium bicarbonate (10 mL) and extracted with EtOAc (50 mL×3). The combined organic fractions were washed with brine, dried over a pad of magnesium sulfate, filtered, and concentrated in vacuo to yield 0.563 g of crude N-Boc-N-hydroxyVal-Val-Dil-Dap-2-(2-pyridyl)ethylamine (0.712 mmol, 43%) that was used without further purification.

To a room temperature solution of N-Boc-N-hydroxyVal-Val-Dil-Dap-2-(2-pyridyl)ethylamine (0.563 g, 0.712 mmol) in DMF (2 mL) was added TFA (2 mL). After 2 h, analysis by LCMS showed the reaction was complete. Volatile organics were evaporated in vacuo. The crude oil was purified by preparatory RP-HPLC with a Phenomenex Synergi 10µ.

Max-RP 80 Å column (150×30 mm) using 10% to 90% MeCN in 0.05% aqueous TFA as the eluent. A total of 0.209 g of the title compound was obtained as the TFA salt (0.302 mmol, 43%). LCMS RT=1.70 min (Method A); ESI-MS m/z 691.53 $[M+H]^+$; HRMS m/z 691.4755 $[C_{36}H_{62}N_6O_7+H]^+$.

Example 14

((2R,3R)-3-((S)-1-((3R,4S,5S)-4-((S)-2-((S)-2-(dimethylamino)-3-hydroxypropanamido)-N,3-dimethylbutanamido)-3-methoxy-5-methylheptanoyl)pyrrolidin-2-yl)-3-methoxy-2-methylpropanoyl)-L-phenylalanine

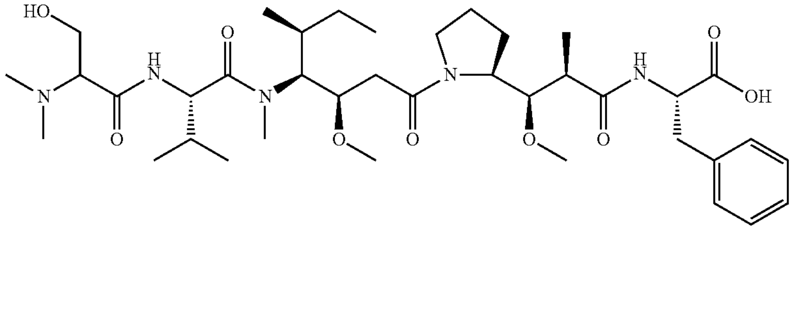 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)C(CO)N(C)C)C(C)C]

To a stirred room temperature solution of H-Ser(Bzl)-OH (0.500 g, 2.56 mmol) and paraformaldehyde (1.15 g, 38.4 mmol) in MeOH (10 mL) was added $HCO_2NH_4$ (0.808 g, 12.8 mmol) and palladium on activated charcoal (10% Pd basis, 0.250 g). After 72 h, analysis by LCMS showed the reaction was complete. The crude reaction mixture was filtered over a pad of diatomaceous earth and the filtrate was concentrated. The crude oil was purified by preparatory RP-HPLC with a Phenomenex Synergi 10μ Max-RP 80 Å column (150×30 mm) using 10% to 90% MeCN in 0.05% aqueous TFA as the eluent. A total of 0.168 g of N,N-dimethylSer(Bzl)-OH (0.498 mmol, 19%) was obtained as the TFA salt.

To a stirred room temperature solution of crude Fmoc-Val-Dil-OtBu (13.3 g, 22.8 mmol) in $CH_2Cl_2$ (20 mL) was added piperidine (15 mL). After 8 h, analysis by LCMS showed the reaction was complete. Volatile organics were evaporated in vacuo to yield crude H-Val-Dil-OtBu that was used without further purification.

To a stirred room temperature suspension of crude H-Val-Dil-OtBu and N,N-dimethylSer(Bzl)-OH TFA salt (0.780 g, 3.49 mmol) in DMF (10 mL) was added DIEA (1.25 mL, 6.99 mmol), followed by HATU (1.77 g, 4.66 mmol). After 6 h, analysis by LCMS showed that the reaction was complete. The crude reaction mixture was diluted with saturated sodium bicarbonate (10 mL) and extracted with EtOAc (40 mL×2). The combined organic fractions were washed with brine, dried over a pad of magnesium sulfate, filtered, and concentrated in vacuo. The crude oil was purified by preparatory RP-HPLC with a Phenomenex Synergi 10μ Max-RP 80 Å column (150×30 mm) using 10% to 90% MeCN in 0.05% aqueous TFA as the eluent. A total of 0.220 g of N,N-dimethylSer(Bzl)-Val-Dil-OtBu (0.325 mmol, 14%) was obtained as the TFA salt.

To a room temperature solution N,N-dimethylSer(Bzl)-Val-Dil-OtBu TFA salt (0.220 g, 0.325 mmol) in $CH_2Cl_2$ (5 mL) was added TFA (2 mL). After 10 h, analysis by LCMS showed the reaction was complete. Volatile organics were evaporated in vacuo to yield crude N,N-dimethylSer(Bzl)-Val-Dil-OH TFA salt that was used without further purification.

To a stirred room temperature suspension of crude N,N-dimethylSer(Bzl)-Val-Dil-OH TFA salt and H-Dap-Phe-OMe TFA salt (0.166 g, 0.477 mmol) in DMF (5 mL) was added DIEA (0.207 mL, 1.30 mmol), followed by HATU (0.330 g, 0.868 mmol). After 4 h, analysis by LCMS showed the reaction was complete. The crude reaction mixture was diluted with saturated sodium bicarbonate (10 mL) and extracted with EtOAc (40 mL×2). The combined organic fractions were washed with brine, dried over a pad of magnesium sulfate, filtered, and concentrated in vacuo. The crude oil was purified by preparatory RP-HPLC with a Phenomenex Synergi 10 Max-RP 80 Å column (150×30 mm) using 10% to 90% MeCN in 0.05% aqueous TFA as the eluent. A total of 0.201 g N,N-dimethylSer(Bzl)-Val-Dil-Dap-Phe-OMe (0.211 mmol, 49%) was obtained as the TFA salt.

To a stirred room temperature suspension of N,N-dimethylSer(Bzl)-Val-Dil-Dap-Phe-OMe TFA salt (0.201 g, 0.211 mmol) and $NH_4HCO_2$ (2.00 g, 31.7 mmol) in MeOH (6 mL) and water (1.0 mL) was added 10% Pd/C (10 mg). The solution was stirred vigorously at room temperature. After 10 h, analysis by LCMS showed the reaction was complete, along with hydrolysis of the methyl ester of phenylalanine. The reaction mixture was filtered through a pad of a diatomaceous earth and the filtrate was concentrated. The crude oil was purified by preparatory RP-HPLC with a Phenomenex Synergi 10μ Max-RP 80 Å column (150×30 mm) using 10% to 90% MeCN in 0.05% aqueous TFA as the eluent. A total of 63.0 mg of the title compound was obtained as the TFA salt (0.074 mmol, 31%). LCMS RT=2.01 min (Method A); ESI-MS m/z 734.61 $[M+H]^+$; HRMS m/z 734.4715 $[C_{38}H_{63}N_5O_9+H]^+$.

Example 15

((2R,3R)-3-((S)-1-((3R,4S,5S)-4-((S)-2-((2S,3R)-2-(dimethylamino)-3-hydroxybutanamido)-N,3-dimethylbutanamido)-3-methoxy-5-methylheptanoyl)pyrrolidin-2-yl)-3-methoxy-2-methylpropanoyl)-L-phenylalanine

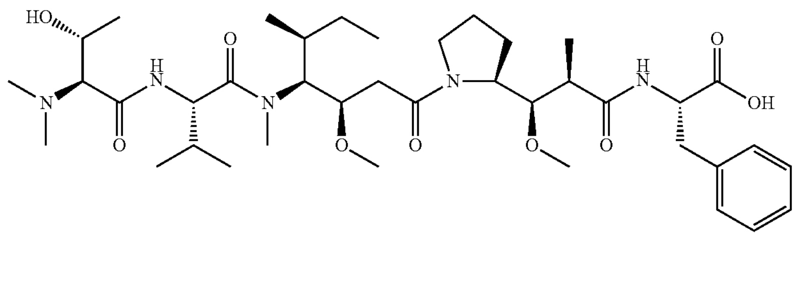 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H]([C@@H](C)O)N(C)C)C(C)C]

To a stirred room temperature solution of H-Thr(Bzl)-OH (2.00 g, 9.56 mmol) and paraformaldehyde (9.87 g, 95.6 mmol) in MeOH (40 mL) was added $HCO_2NH_4$ (3.01 g, 47.8 mmol) and palladium on activated charcoal (10% Pd basis, 1.00 g). After 72 h, analysis by LCMS showed the reaction was complete. The crude reaction mixture was filtered over a pad of diatomaceous earth and the filtrate was concentrated. The crude oil was purified by preparatory RP-HPLC with a Phenomenex Synergi 10 Max-RP 80 Å column (150×30 mm) using 10% to 90% MeCN in 0.05% aqueous TFA as the eluent. A total of 1.54 g of N,N-dimethylThr(Bzl)-OH (4.38 mmol, 19%) was obtained as the TFA salt.

To a stirred room temperature suspension of crude H-Val-Dil-OtBu and N,N-dimethylThr(Bzl)-OH TFA salt (1.21 g, 5.10 mmol) in DMF (20 mL) was added DIEA (1.82 mL, 10.2 mmol), followed by HATU (2.59 g, 6.80 mmol). After 6 h, analysis by LCMS showed that the reaction was complete. The crude reaction mixture was diluted with saturated sodium bicarbonate (15 mL) and extracted with EtOAc (40 mL×2). The combined organic fractions were washed with brine, dried over a pad of magnesium sulfate, filtered, and concentrated in vacuo. The crude oil was purified by preparatory RP-HPLC with a Phenomenex Synergi 10μ Max-RP 80 Å column (150×30 mm) using 10% to 90% MeCN in 0.05% aqueous TFA as the eluent. A total of 0.161 g of N,N-dimethylThr(Bzl)-Val-Dil-OtBu (0.234 mmol, 7%) was obtained as the TFA salt.

To a room temperature solution N,N-dimethylThr(Bzl)-Val-Dil-OtBu TFA salt (0.220 g, 0.325 mmol) in $CH_2Cl_2$ (5 mL) was added TFA (2 mL). After 10 h, analysis by LCMS showed the reaction was complete. Volatile organics were evaporated in vacuo to yield crude N,N-dimethylThr(Bzl)-Val-Dil-OH TFA salt that was used without further purification.

To a stirred room temperature suspension of crude N,N-dimethylThr(Bzl)-Val-Dil-OH TFA salt and H-Dap-Phe-OMe TFA salt (0.118 g, 0.339 mmol) in DMF (5 mL) was added DIEA (0.147 mL, 0.927 mmol), followed by HATU (0.235 g, 0.618 mmol). After 4 h, analysis by LCMS showed the reaction was complete. The crude reaction mixture was diluted with saturated sodium bicarbonate (10 mL) and extracted with EtOAc (40 mL×2). The combined organic fractions were washed with brine, dried over a pad of magnesium sulfate, filtered, and concentrated in vacuo. The crude oil was purified by preparatory RP-HPLC with a Phenomenex Synergi 10 Max-RP 80 Å column (150×30 mm) using 10% to 90% MeCN in 0.05% aqueous TFA as the eluent. A total of 0.186 g N,N-dimethylThr(Bzl)-Val-Dil-Dap-Phe-OMe (0.193 mmol, 62%) was obtained as the TFA salt.

To a stirred room temperature suspension of N,N-dimethylThr(Bzl)-Val-Dil-Dap-Phe-OMe TFA salt (0.186 g, 0.193 mmol) and $NH_4HCO_2$ (2.00 g, 31.7 mmol) in MeOH (6 mL) and water (1.0 mL) was added 10% Pd/C (100 mg). The solution was stirred vigorously at room temperature. After 72 h, analysis by LCMS showed the reaction was complete, along with hydrolysis of the methyl ester of phenylalanine. The reaction mixture was filtered through a pad of diatomaceous earth and the filtrate was concentrated. The crude oil was purified by preparatory RP-HPLC with a Phenomenex Synergi 10μ Max-RP 80 Å column (150×30 mm) using 10% to 90% MeCN in 0.05% aqueous TFA as the eluent. A total of 63.0 mg of the title compound was obtained as the TFA salt (0.073 mmol, 38%). LCMS RT=2.04 min (Method A); ESI-MS m/z 748.58 $[M+H]^+$; HRMS m/z 748.4854 $[C_{39}H_{65}N_5O_9+H]^+$.

Example 16

(S)-2-((2R,3R)-3-((S)-1-((3R,4S,5S)-4-((2S,3S)-3-azido-2-((S)-2-(dimethylamino)-3-methylbutanamido)-N-methylbutanamido)-3-methoxy-5-methylheptanoyl)pyrrolidin-2-yl)-3-methoxy-2-methylpropanamido)-3-phenylpropanoic acid

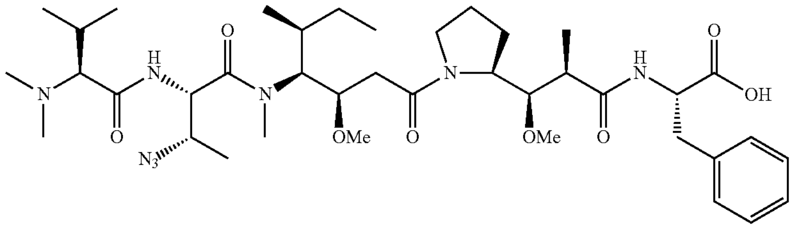 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)C)[C@H](C)N=[N+]=[N-]]

To a stirred room temperature solution of Dov-Abu(3-$N_3$)-Dil-Dap-Phe-OMe TFA salt (60 mg, 0.067 mmol) in MeOH (0.1 mL) and THF (0.1 mL) was added lithium hydroxide monohydrate (9.6 mg, 0.229 mmol) in water (0.1 mL). After 12 h, analysis by LCMS showed the reaction was complete. The crude oil was purified by preparatory RP-HPLC with a Phenomenex Synergi 10 Max-RP 80 Å column (150×30 mm) using 10% to 90% MeCN in 0.05% aqueous TFA as the eluent. A total of 55.0 mg of the title compound was obtained as the TFA salt (0.062 mmol, 93%). LCMS RT=2.25 min (Method A); ESI-MS m/z 773.45 $[M+H]^+$; HRMS m/z 773.49119 $[C_{39}H_{64}N_8O_8+H]^+$.

Example 17

(S)—N-((3R,4S,5S)-1-((S)-2-((1R,2R)-3-(((S)-1-amino-1-oxo-3-phenylpropan-2-yl)amino)-1-methoxy-2-methyl-3-oxopropyl)pyrrolidin-1-yl)-3-methoxy-5-methyl-1-oxoheptan-4-yl)-2-((2S,3R)-2-(dimethylamino)-3-hydroxybutanamido)-N,3-dimethylbutanamide

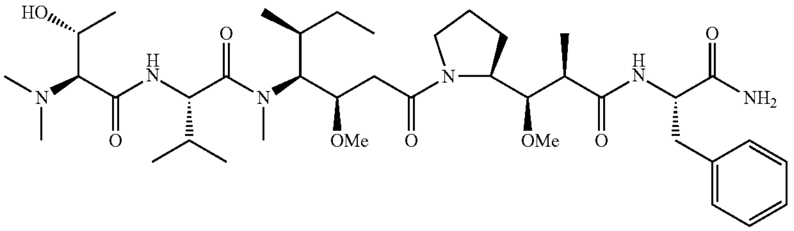 [SMILES: CC[C@H](C)[C@@H]([C@@H](CC(=O)N1CCC[C@H]1[C@H](OC)[C@@H](C)C(=O)N[C@@H](Cc1ccccc1)C(N)=O)OC)N(C)C(=O)[C@@H](NC(=O)[C@H]([C@@H](C)O)N(C)C)C(C)C]

To a stirred room temperature solution of N,N-dimethyl-Thr-Val-Dil-Dap-Phe-OH TFA salt (40 mg, 0.053 mmol) in $CH_2Cl_2$ (10 mL) was added ammonium chloride (5.72 mg, 0.107 mmol), DIEA (28.6 μL, 0.160 mmol) and EDCI (30.3 mg, 0.107 mmol). After 12 h, analysis by LCMS showed the reaction was complete. The crude oil was purified by preparatory RP-HPLC with a Phenomenex Synergi 10μ Max-RP 80 Å column (150×30 mm) using 10% to 90% MeCN in 0.05% aqueous TFA as the eluent. A total of 28.0 mg of the title compound was obtained as the TFA salt (0.037 mmol, 70%). LCMS RT=2.14 min (Method A); ESI-MS m/z 747.61 $[M+H]^+$; HRMS m/z 747.5017 $[C_{39}H_{66}N_6O_8+H]^+$.

Example 18

(S)—N-((3R,4S,5S)-1-((S)-2-((1R,2R)-3-(((S)-1-amino-1-oxo-3-phenylpropan-2-yl)amino)-1-methoxy-2-methyl-3-oxopropyl)pyrrolidin-1-yl)-3-methoxy-5-methyl-1-oxoheptan-4-yl)-2-((S)-2-(dimethylamino)-3-hydroxypropanamido)-N,3-dimethylbutanamide

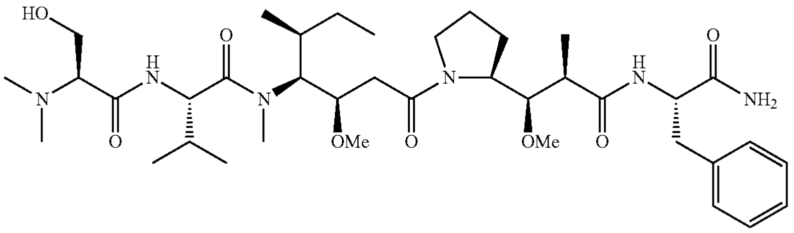 [SMILES: CC[C@H](C)[C@@H]([C@@H](CC(=O)N1CCC[C@H]1[C@H](OC)[C@@H](C)C(=O)N[C@@H](Cc1ccccc1)C(N)=O)OC)N(C)C(=O)[C@@H](NC(=O)[C@H](CO)N(C)C)C(C)C]

To a stirred room temperature solution of N,N-dimethyl-Ser-Val-Dil-Dap-Phe-OH TFA salt (12 mg, 0.016 mmol) in $CH_2Cl_2$ (10 mL) was added ammonium chloride (1.00 mg, 0.019 mmol), DIEA (3.21 µL, 0.018 mmol) and EDCI (5.09 mg, 0.018 mmol). After 12 h, analysis by LCMS showed the reaction was complete. The crude oil was purified by preparatory RP-HPLC with a Phenomenex Synergi 10 Max-RP 80 Å column (150×30 mm) using 10% to 90% MeCN in 0.05% aqueous TFA as the eluent. A total of 10.0 mg of the title compound was obtained as the TFA salt (0.014 mmol, 83%). LCMS RT=2.07 min (Method A); ESI-MS m/z 733.63 $[M+H]^+$; HRMS m/z 733.4866 $[C_{38}H_{64}N_6O_8+H]^+$.

Example 19

(S)-methyl 2-((2R,3R)-3-((S)-1-((3R,4S,5S)-4-((R)-2-((S)-2-(dimethylamino)-3-methylbutanamido)-3-mercapto-N-methylpropanamido)-3-methoxy-5-methylheptanoyl)pyrrolidin-2-yl)-3-methoxy-2-methylpropanamido)-3-phenylpropanoate

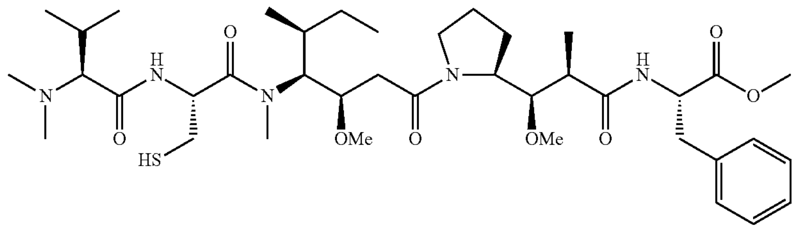

To a stirred room temperature solution of Fmoc-Cys(Trt)-OH (3.96 g, 6.76 mmol) and H-Dil-OtBu hydrochloride (2.00 g, 6.76 mmol) in EtOAc (15 mL) was added DIEA (2.17 mL, 12.2 mmol). The solution was cooled (0° C.) and stirred for 20 min. Additional DIEA (2.17 mL, 12.2 mmol) was added to the reaction mixture, and the 0° C. solution was stirred for 20 min. Then CMPI (2.76 g, 10.8 mmol) was added to the reaction mixture and the reaction mixture was allowed to reach room temperature. After 12 h, analysis by LCMS showed the reaction was complete. The crude reaction was washed with 0.1 M HCl (100 mL×2), followed by brine (20 mL×2). The organic fraction was dried over a pad of magnesium sulfate, filtered and concentrated in vacuo. Fmoc-Cys(Trt)-Dil-OtBu was isolated by flash chromatography on silica gel (silica gel 40 µm, 60 Å, 3.0×17.0 cm) using 18% to 90% EtOAc in hexanes as the eluent. A total of 4.73 g of Fmoc-Cys(Trt)-Dil-OtBu (5.72 mmol, 85% yield) was obtained.

To a stirred room temperature solution of Fmoc-Cys(Trt)-Dil-OtBu (2.61 g, 3.16 mmol) in MeCN (10 mL) was added piperidine (5 mL). After 5 h, analysis by LCMS showed the reaction was complete. The crude reaction mixture was extracted with hexanes and the MeCN layer was concentrated in vacuo to yield crude H-Cys(Trt)-Dil-OtBu that was used without further purification.

To a stirred room temperature suspension of crude H-Cys(Trt)-Dil-OtBu and Dov (0.916 g, 6.31 mmol) in DMF (15 mL) was added DIEA (1.69 mL, 9.47 mmol), followed by HATU (2.40 g, 6.31 mmol). After 8 h, analysis by LCMS showed that the reaction was complete. The crude reaction mixture was diluted with saturated sodium bicarbonate (10 mL) and extracted with EtOAc (40 mL×2). The combined organic fractions were washed with brine, dried over a pad of magnesium sulfate, filtered, and concentrated in vacuo. The crude oil was purified by preparatory RP-HPLC with a Phenomenex Synergi 10µ Max-RP 80 Å column (150×30 mm) using 10% to 90% MeCN in 0.05% aqueous TFA as the eluent. A total of 1.40 g Dov-Cys(Trt)-Dil-OtBu (1.66 mmol, 52%) was obtained as the TFA salt.

To a room temperature solution of Dov-Cys(Trt)-Dil-OtBu TFA salt (1.40 g, 1.66 mmol) in $CH_2Cl_2$ (10 mL) was added TFA (5 mL). After 10 h, analysis by LCMS showed the reaction was complete. Volatile organics were evaporated in vacuo to yield crude Dov-Cys(Trt)-Dil-OH TFA salt that was used without further purification.

To a stirred room temperature suspension of Dov-Cys(Trt)-Dil-OH TFA salt (0.225 g, 285 mmol) and H-Dap-Phe-OMe TFA salt (0.139 g, 0.301 mmol) in DMF (10 mL) was added DIEA (0.237 mL, 1.33 mmol), followed by HOBt (0.102 g, 0.666 mmol) and HATU (0.253 g, 0.666 mmol). After overnight stirring, analysis by LCMS showed the reaction was complete. The crude reaction mixture was diluted with saturated sodium bicarbonate (10 mL) and extracted with EtOAc (50 mL×3). The combined organic fractions were washed with brine, dried over a pad of magnesium sulfate, filtered, and concentrated in vacuo and used without further purification.

To a room temperature solution of Dov-Cys(Trt)-Dil-Dap-Phe-OMe TFA salt (0.568 g, 0.507 mmol) was added TFA (10 mL). After 12 h at 60° C., analysis by LCMS showed the reaction was complete. Volatile organics were evaporated in vacuo. The crude oil was purified by preparatory RP-HPLC with a Phenomenex Synergi 10µ Max-RP 80 Å column (150×30 mm) using 10% to 90% MeCN in 0.05% aqueous TFA as the eluent. A total of 10.0 mg of the title compound was obtained as the disulfide bridge dimer TFA salt (0.011 mmol, 3%). LCMS RT=2.50 min (Method A); ESI-MS n/z 764.60 $[M+H]^+$; HRMS m/z 763.4547 z=2.

Example 20

(S)-2-((2R,3R)-3-((S)-1-((3R,4S,5S)-4-((R)-2-((S)-2-(dimethylamino)-3-methylbutanamido)-3-mercapto-N-methylpropanamido)-3-methoxy-5-methylheptanoyl)pyrrolidin-2-yl)-3-methoxy-2-methylpropanamido)-3-phenylpropanoic acid

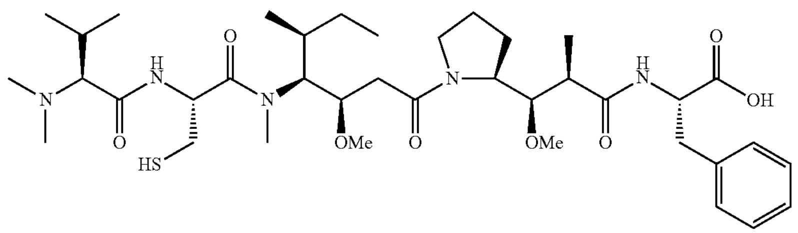

To a stirred room temperature solution of Boc-Dap-OH dicyclohexylamine salt (6.47 g, 13.8 mmol) and H-Phe-OtBu HCl salt (3.91 g, 15.2 mmol) in DCM (20 mL) was added DIEA (8.78 mL, 55.2 mmol), followed by DEPC (3.12 mL, 20.7 mmol). After 8 h, analysis by LCMS showed the reaction was complete. The volatile organic were evaporated in vacuo to give crude product that was used without further purification.

To a stirred room temperature solution of Boc-Dap-Phe-OtBu (5.25 g, 10.7 mmol) in $CH_2Cl_2$ (10 mL) was added TFA (10 mL). After 12 h, analysis by LCMS showed the reaction was complete as a mixture of the free phenylalanine carboxylic acid and the tBu ester. The crude oil was purified by preparatory RP-HPLC with a Phenomenex Synergi 10μ Max-RP 80 Å column (150×30 mm) using 10% to 90% MeCN in 0.05% aqueous TFA as the eluent. A total of 2.85 g of H-Dap-Phe-OtBu TFA salt (5.65 mmol) was obtained as an amber oil and a total of 2.01 g of H-Dap-Phe-OH TFA salt (4.49 mmol) was obtained as a yellow oil.

To a stirred room temperature suspension of crude Dov-Cys(Trt)-Dil-OH TFA salt (0.208 g) and H-Dap-Phe-OtBu TFA salt (0.144 g, 0.369 mmol) in DMF (10 mL) was added DIEA (0.219 mL, 1.23 mmol), followed by HATU (0.234 g, 0.615 mmol). After 10 h, analysis by LCMS showed the reaction was complete. The crude reaction mixture was diluted with saturated sodium bicarbonate (10 mL) and extracted with EtOAc (40 mL×2). The combined organic fractions were washed with brine, dried over a pad of magnesium sulfate, filtered, and concentrated in vacuo. The crude oil was purified by preparatory RP-HPLC with a Phenomenex Synergi 10p. Max-RP 80 Å column (150×30 mm) using 10% to 90% MeCN in 0.05% aqueous TFA as the eluent. A total of 0.509 g of enriched Dov-Cys(Trt)-Dil-Dap-Phe-OtBu was obtained as the TFA salt.

To a room temperature solution of enriched Dov-Cys(Trt)-Dil-Dap-Phe-OtBu TFA salt (0.509) was added TFA (5 mL). The solution was heated to 60° C. and stirred for 24 h. After 24 h, analysis by LCMS showed the reaction was complete. Volatile organics were evaporated in vacuo. The crude oil was purified by preparatory RP-HPLC with a Phenomenex Synergi 10μ Max-RP 80 Å column (150×30 mm) using 10% to 90% MeCN in 0.05% aqueous TFA as the eluent. A total of 56.0 mg of the title compound was obtained as the TFA salt (0.065 mmol, 25%). LCMS RT=2.32 min (Method A); ESI-MS m/z 750.60 $[M+H]^+$; HRMS m/z 750.4460 $[C_{38}H_{63}N_5O_8S+H]^+$.

Example 21

(S)-2-((2R,3R)-3-((S)-1-((3R,4S,5S)-4-((S)-2-((S)-2-(dimethylamino)-3-methylbutanamido)-3-hydroxy-N-methylpropanamido)-3-methoxy-5-methylheptanoyl)pyrrolidin-2-yl)-3-methoxy-2-methylpropanamido)-3-phenylpropanoic acid

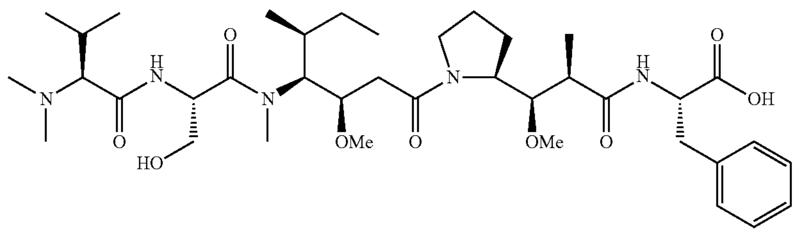 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@H](CS)NC(=O)[C@H](C(C)C)N(C)C]

To a stirred room temperature suspension of crude Dov-Ser(Bzl)-Dil-OH TFA salt (0.232 g) and H-Dap-Phe-OtBu TFA salt (0.196 g, 0.389 mmol) in DMF (10 mL) was added DIEA (0.326 mL, 1.83 mmol), followed by HATU (0.348, 0.914 mmol). After 6 h, analysis by LCMS showed the reaction was complete. The crude reaction mixture was diluted with saturated sodium bicarbonate (10 mL) and extracted with EtOAc (40 mL×2). The combined organic fractions were washed with brine, dried over a pad of magnesium sulfate, filtered, and concentrated in vacuo. The crude oil was purified by preparatory RP-HPLC with a Phenomenex Synergi 10μ Max-RP 80 Å column (150×30 mm) using 10% to 90% MeCN in 0.05% aqueous TFA as the eluent. A total of 0.378 g Dov-Ser(Bzl)-Dil-Dap-Phe-OtBu (0.380 mmol, 98%) was obtained as the TFA salt.

To a room temperature solution of Dov-Ser(Bzl)-Dil-Dap-Phe-OtBu TFA salt (0.455 g, 0.517 mmol) in $CH_2Cl_2$ (5 mL) was added TFA (2 mL). After 12 h, analysis by LCMS showed the reaction was complete. Volatile organics were evaporated in vacuo to yield crude of Dov-Ser(Bzl)-Dil-Dap-Phe-OH TFA salt that was used without further purification.

A stirred room temperature suspension of crude Dov-Ser (Bzl)-Dil-Dap-Phe-OH TFA salt from the previous step and palladium on activated charcoal (10% Pd basis, 10.0 mg) in MeOH (10 mL) was hydrogenated. After 12 h, analysis by LCMS showed the reaction was complete. The crude reaction mixture was filtered over a pad of diatomaceous earth and the filtrate was concentrated. The crude oil was purified by preparatory RP-HPLC with a Phenomenex Synergi 10 Max-RP 80 Å column (150×30 mm) using 10% to 90% MeCN in 0.05% aqueous TFA as the eluent. A total of 0.115 g of the title compound was obtained as the TFA salt (0.136 mmol, 28%). LCMS RT=2.10 min (Method A); ESI-MS m/z 734.61 $[M+H]^+$; HRMS m/z 734.4708 $[C_{38}H_{63}N_5O_9+H]^+$.

Example 22

(S)-2-((2R,3R)-3-((S)-1-((3R,4S,5S)-4-((2S,3R)-2-((S)-2-(dimethylamino)-3-methylbutanamido)-3-hydroxy-N-methylbutanamido)-3-methoxy-5-methylheptanoyl)pyrrolidin-2-yl)-3-methoxy-2-methylpropanamido)-3-phenylpropanoic acid

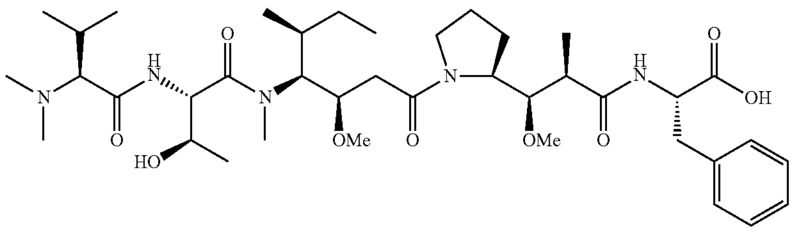 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)C)[C@@H](C)O]

To a stirred room temperature suspension of crude Dov-Thr(Bzl)-Dil-OH TFA salt (0.180 g) and H-Dap-Phe-OtBu TFA salt (0.148 g, 0.294 mmol) in DMF (10 mL) was added DIEA (0.246 mL, 1.38 mmol), followed by HATU (0.262, 0.690 mmol). After 6 h, analysis by LCMS showed the reaction was complete. The crude reaction mixture was diluted with saturated sodium bicarbonate (10 mL) and extracted with EtOAc (40 mL×2). The combined organic fractions were washed with brine, dried over a pad of magnesium sulfate, filtered, and concentrated in vacuo. The crude oil was purified by preparatory RP-HPLC with a Phenomenex Synergi 10μ Max-RP 80 Å column (150×30 mm) using 10% to 90% MeCN in 0.05% aqueous TFA as the eluent. A total of 0.298 g Dov-Thr(Bzl)-Dil-Dap-Phe-OtBu (0.296 mmol, 78%) was obtained as the TFA salt.

To a room temperature solution of Dov-Thr(Bzl)-Dil-Dap-Phe-OtBu TFA salt (0.298 g, 0.296 mmol) in $CH_2Cl_2$ (5 mL) was added TFA (2 mL). After 10 h, analysis by LCMS showed the reaction was complete. Volatile organics were evaporated in vacuo to yield crude of Dov-Thr(Bzl)-Dil-Dap-Phe-OH TFA salt that was used without further purification.

A stirred room temperature suspension of crude Dov-Thr(Bzl)-Dil-Dap-Phe-OH TFA salt from the previous step and palladium on activated charcoal (10% Pd basis, 10.0 mg) in MeOH (10 mL) was hydrogenated. After 12 h, analysis by LCMS showed the reaction was complete. The crude reaction mixture was filtered over a pad of diatomaceous earth and the filtrate was concentrated. The crude oil was purified by preparatory RP-HPLC with a Phenomenex Synergi 10 Max-RP 80 Å column (150×30 mm) using 10% to 90% MeCN in 0.05% aqueous TFA as the eluent. A total of 0.120 g of the title compound was obtained as the TFA salt (0.139 mmol, 47%). LCMS RT=2.22 min (Method A); ESI-MS m/z 748.62 $[M+H]^+$; HRMS m/z 748.4842 $[C_{39}H_{65}N_5O_9+H]^+$.

Example 23

(S)-methyl 2-((2R,3R)-3-((S)-1-((3R,4S,5S)-4-((S)-2-((S)-2-(dimethylamino)-3-hydroxypropanamido)-N,3-dimethylbutanamido)-3-methoxy-5-methylheptanoyl)pyrrolidin-2-yl)-3-methoxy-2-methylpropanamido)-3-phenylpropanoate

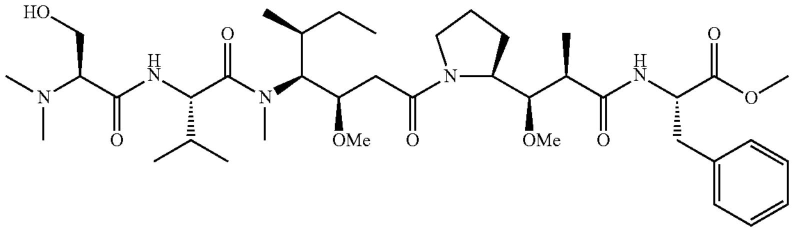

A stirred room temperature suspension of N,N-dimethyl-Ser(Bzl)-Val-Dil-Dap-Phe-OMe TFA salt (50.0 mg, 0.053 mmol) and palladium on activated charcoal (10% Pd basis, 10 mg) in MeOH (10 mL) was hydrogenated. After 10 h, analysis by LCMS showed the reaction was complete. The crude reaction mixture was filtered over a pad of diatomaceous earth and the filtrate was concentrated. The crude oil was purified by preparatory RP-HPLC with a Phenomenex Synergi 10 μL Max-RP 80 Å column (150×30 mm) using 10% to 90% MeCN in 0.05% aqueous TFA as the eluent. A total of 8.00 mg of the title compound was obtained as the TFA salt (0.009 mmol, 18%). LCMS RT=2.38 min (Method A); ESI-MS m/z 748.57 $[M+H]^+$; HRMS m/z 748.4849 $[C_{39}H_{65}N_5O_9+H]^+$.

Example 24

(S)-methyl 2-((2R,3R)-3-((S)-1-((3R,4S,5S)-4-((S)-2-((2S,3R)-2-(dimethylamino)-3-hydroxybutanamido)-N,3-dimethylbutanamido)-3-methoxy-5-methylheptanoyl)pyrrolidin-2-yl)-3-methoxy-2-methylpropanamido)-3-phenylpropanoate

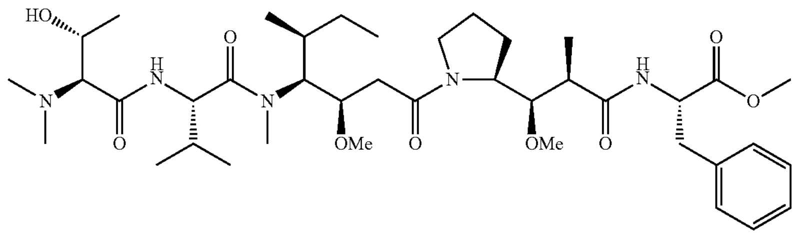

The title compound may be prepared using methods analogous to those described in the Examples and general synthetic schemes.

Example 25

(S)-methyl 2-((2R,3R)-3-((S)-1-((3R,4S,5S)-4-((2S,3S)-3-amino-2-((S)-2-(dimethylamino)-3-methylbutanamido)-N-methylbutanamido)-3-methoxy-5-methylheptanoyl)pyrrolidin-2-yl)-3-methoxy-2-methylpropanamido)-3-phenylpropanoate

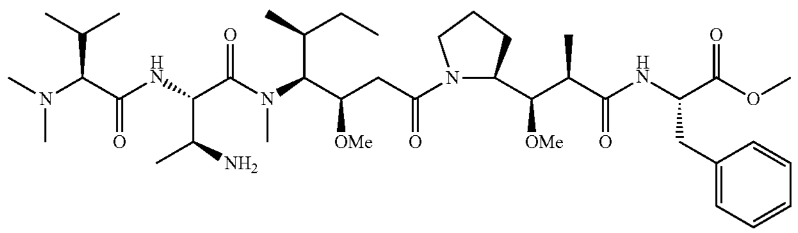

To a stirred room temperature solution of Dov-Abu(3-$N_3$)-Dil-Dap-Phe-OMe TFA salt (10 mg, 0.011 mmol) in THF (0.10 mL) was added trimethylphosphine in THF (1 M, 0.022 mL, 0.022 mmol). After 4 h, analysis by LCMS showed the reaction was complete and $H_2O$ (0.05 mL) was added to the reaction mixture. The crude reaction mixture was purified by preparatory RP-HPLC with a Phenomenex Synergi 10 Max-RP 80 Å column (150×30 mm) using 10% to 90% MeCN in 0.05% aqueous TFA as the eluent. A total of 6.00 mg of the title compound was obtained as the TFA salt (0.007 mmol, 62%). LCMS RT=2.12 min (Method A); ESI-MS m/z 761.63 $[M+H]^+$; HRMS m/z 761.5159 $[C_{40}H_{68}N_6O_8+H]^+$.

Example 26

(S)-2-((2R,3R)-3-((S)-1-((3R,4S,5S)-4-((2S,3S)-3-amino-2-((S)-2-(dimethylamino)-3-methylbutanamido)-N-methylbutanamido)-3-methoxy-5-methylheptanoyl)pyrrolidin-2-yl)-3-methoxy-2-methylpropanamido)-3-phenylpropanoic acid

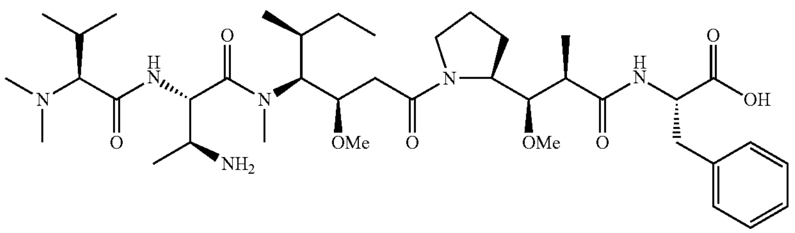 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)C)[C@H](C)N]

To a stirred room temperature solution of Dov-Abu(3-$N_3$)-Dil-Dap-Phe-OH TFA salt (10 mg, 0.011 mmol) in THF (0.10 mL) was added trimethylphosphine in THF (1 M, 0.022 mL, 0.022 mmol). After 4 h, analysis by LCMS showed the reaction was complete and $H_2O$ (0.05 mL) was added to the reaction mixture. The crude reaction mixture was purified by preparatory RP-HPLC with a Phenomenex Synergi 10μ Max-RP 80 Å column (150×30 mm) using 10% to 90% MeCN in 0.05% aqueous TFA as the eluent. A total of 2.00 mg of the title compound was obtained as the TFA salt (0.002 mmol, 21%). LCMS RT=2.02 min (Method A); ESI-MS m/z 747.65 $[M+H]^+$; HRMS m/z 747.5008 $[C_{39}H_{66}N_6O_8+H]^+$.

Example 27

(2S,3S)-3-azido-2-((S)-2-(dimethylamino)-3-methylbutanamido)-N-((3R,4S,5S)-3-methoxy-1-((S)-2-((1R,2R)-1-methoxy-2-methyl-3-oxo-3-(phenethylamino)propyl)pyrrolidin-1-yl)-5-methyl-1-oxoheptan-4-yl)-N-methylbutanamide

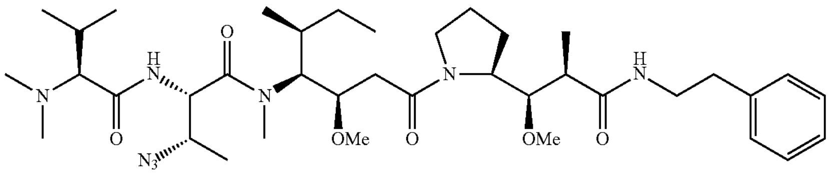 [SMILES: CC[C@H](C)[C@@H]([C@@H](CC(=O)N1CCC[C@H]1[C@H](OC)[C@@H](C)C(=O)NCCc1ccccc1)OC)N(C)C(=O)[C@@H](NC(=O)[C@H](C(C)C)N(C)C)[C@H](C)N=[N+]=[N-]]

To a stirred 25° C. solution of Boc-Dap-OH dicyclohexylamine salt (6.47 g, 13.8 mmol) and phenethylamine (3.914 g, 15.19 mmol) in $CH_2Cl_2$ (20 mL) was added DIEA (8.76 mL, 55.2 mmol), followed by DEPC (3.12 mL, 20.7 mmol). After 8 h, analysis by LCMS showed the reaction was complete. The volatile organic were evaporated in vacuo to give crude product that was used without further purification. A total of 4.04 g of Boc-Dap-phenethylamine (10.3 mmol) was obtained. LCMS RT=3.00 min (Method A); ESI-MS m/z 391.37 $[M+H]^+$.

To a stirred 25° C. solution of Boc-Dap-phenethylamine (4.04 g, 10.3 mmol) in $CH_2Cl_2$ (15.0 mL) was added TFA (15.0 mL). After 14 h, analysis by LCMS showed the reaction was complete. The volatile organic were evaporated in vacuo an the crude oil was purified by preparatory RP-HPLC with a Phenomenex Synergi 10μ Max-RP 80 Å column (150×30 mm) using 10% to 90% MeCN in 0.05% aqueous TFA as the eluent. A total of 2.51 g of H-Dap-phenethylamine (6.21 mmol) was obtained as the TFA salt. LCMS RT=1.72 min (Method A); ESI-MS m/z 291.29 $[M+H]^+$.

To a stirred room temperature solution of Dov-Abu(3-$N_3$)-Dil-OH TFA salt (0.300 g, 0.526 mmol) and H-Dap-phenethylamine TFA salt (0.191 g, 0.471 mmol) in DMF (5 mL) was added DIEA (0.343 mL, 1.97 mmol), followed by the addition of HATU (0.501 g, 1.31 mmol). After 10 h, analysis by LCMS showed the reaction was complete. The crude reaction was diluted with saturated sodium bicarbonate (10 mL) and extracted with EtOAc (20 mL×2). The combined organic fractions were washed with brine, dried using magnesium sulfate, filtered, and concentrated in vacuo. The crude oil was purified by preparatory RP-HPLC with a Phenomenex Synergi 10 Max-RP 80 Å column (150×30 mm) using 10% to 90% MeCN in 0.05% aqueous TFA as the eluent. A total of 196 mg of the title compound was obtained as the TFA salt (0.233 mmol, 49%). LCMS RT=2.45 min (Method A); ESI-MS m/z 729.55 $[M+H]^+$; HRMS m/z 729.5030 $[C_{38}H_{64}N_8O_6+H]^+$.

Example 28

(2S,3S)-3-azido-2-((S)-2-(dimethylamino)-3-methylbutanamido)-N-((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N-methylbutanamide

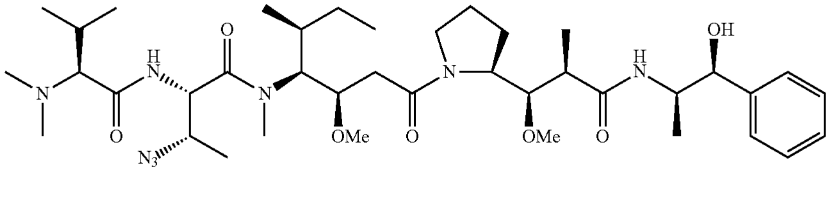 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C)[C@H](C)N=[N+]=[N-]]

To a stirred room temperature solution of Boc-Dap-OH dicyclohexylamine salt (10.0 g, 0.021 mol) and (1R,2S)-(−)-Norephedrine (3.87 g, 0.026 mol) in $CH_2Cl_2$ (20 mL) was added DIEA (11.4 mL, 0.064 mol) and DEPC (6.44 mL, 0.043 mol). After 14 h, analysis by LCMS showed the reaction was complete. To the crude reaction mixture was added 0.1 M HCl (20.0 mL). The organic layer was separated, dried over a pad of magnesium sulfate, filtered, and concentrated in vacuo to yield crude product. A total of 7.92 g of Boc-Dap-(1R,2S)-(−)-Norephedrine (18.8 mmol, 88%) was obtained. LCMS RT=2.25 min (Method A); ESI-MS m/z 421.31 $[M+H]^+$.

To a stirred room temperature solution of Boc-Dap-(1R,2S)-(−)-Norephedrine (7.92 g, 18.8 mmol) in $CH_2Cl_2$ (10 mL) was added TFA (10 mL). After 10 h, analysis by LCMS showed the reaction was complete. The crude oil was purified by preparatory RP-HPLC with a Phenomenex Synergi 10 Max-RP 80 Å column (150×30 mm) using 10% to 90% MeCN in 0.05% aqueous TFA as the eluent. A total of 5.00 g of H-Dap-(1R,2S)-(−)-Norephedrine (11.5 mmol, 61%) was prepared as the TFA salt. LCMS RT=1.10 min (Method A); ESI-MS m/z 321.33 $[M+H]^+$.

To a stirred room temperature solution of Dov-Abu(3-$N_3$)-Dil-OH TFA salt (0.300 g, 0.526 mmol) and H-Dap-(1R,2S)-(−)-Norephedrine TFA salt (0.211 g, 0.486 mmol) in DMF (5 mL) was added DIEA (0.351 mL, 1.97 mmol), followed by the addition of HATU (0.501 g, 1.31 mmol). After 10 h, analysis by LCMS showed the reaction was complete. The crude reaction was diluted with saturated sodium bicarbonate (10 mL) and extracted with EtOAc (20 mL×2). The combined organic fractions were washed with brine, dried using magnesium sulfate, filtered, and concentrated in vacuo. The crude oil was purified by preparatory RP-HPLC with a Phenomenex Synergi 10 Max-RP 80 Å column (150×30 mm) using 10% to 90% MeCN in 0.05% aqueous TFA as the eluent. A total of 128 mg of the title compound was obtained as the TFA salt (0.147 mmol, 30%). LCMS RT=1.95 min (Method A); ESI-MS m/z 759.65 $[M+H]^+$; HRMS m/z 759.5121 $[C_{39}H_{66}N_8O_7+H]^+$.

Example 29

(2S,3S)-3-azido-N-((3R,4S,5S)-1-((S)-2-((1R,2R)-3-((4-chlorophenethyl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N-methylbutanamide

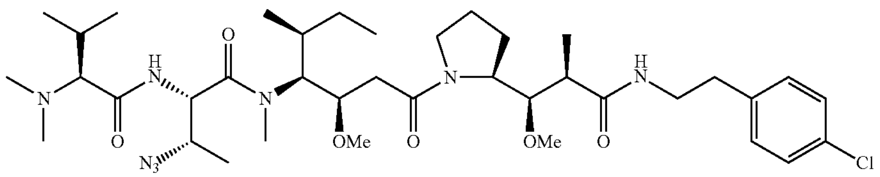 [SMILES: CC[C@H](C)[C@@H]([C@@H](CC(=O)N1CCC[C@H]1[C@H](OC)[C@@H](C)C(=O)NCCc1ccc(Cl)cc1)OC)N(C)C(=O)[C@@H](NC(=O)[C@H](C(C)C)N(C)C)[C@H](C)N=[N+]=[N-]]

To a stirred room temperature solution of Boc-Dap-OH dicyclohexylamine salt (5.00 g, 10.7 mmol) and 2-(4-chlorophenyl)ethylamine (1.85 g, 11.7 mmol) in $CH_2Cl_2$ (20 mL) was added DIEA (6.78 mL, 42.7 mmol) and DEPC (2.41 mL, 16.0 mmol). After 10 h, analysis by LCMS showed the reaction was complete. The volatile organic were evaporated in vacuo to give crude product that was used without further purification. A total of 4.25 g of Boc-Dap-2-(4-chlorophenyl)ethylamine (10.0 mmol, 94%) was obtained. LCMS RT=3.10 min (Method A); ESI-MS m/z 425.32 $[M+H]^+$.

To a stirred room temperature solution of Boc-Dap-2-(4-chlorophenyl)ethylamine (4.25 g, 10.0 mmol) in $CH_2Cl_2$ (15 mL) was added TFA (15 mL). After 10 h, analysis by LCMS showed the reaction was complete. The crude oil was purified by preparatory RP-HPLC with a Phenomenex Synergi 10 μL Max-RP 80 Å column (150×30 mm) using 10% to 90% MeCN in 0.05% aqueous TFA as the eluent. A total of 2.27 g of H-Dap-2-(4-chlorophenyl)ethylamine (5.18 mmol, 52%) was prepared as the TFA salt. LCMS RT=2.05 min (Method A); ESI-MS m/z 325.24 $[M+H]^+$.

To a stirred room temperature solution of Dov-Abu(3-$N_3$)-Dil-OH TFA salt (0.526 g, 0.923 mmol) and H-Dap-2-(4-chlorophenyl)ethylamine TFA salt (0.347 g, 0.792 mmol) in DMF (10 mL) was added DIEA (0.602 mL, 3.46 mmol), followed by the addition of HATU (0.878 g, 2.30 mmol). After 10 h, analysis by LCMS showed the reaction was complete. The crude reaction was diluted with saturated sodium bicarbonate (10 mL) and extracted with EtOAc (20 mL×2). The combined organic fractions were washed with brine, dried using magnesium sulfate, filtered, and concentrated in vacuo. The crude oil was purified by preparatory RP-HPLC with a Phenomenex Synergi 10μ Max-RP 80 Å column (150×30 mm) using 10% to 90% MeCN in 0.05% aqueous TFA as the eluent. A total of 596 mg of the title compound was obtained as the TFA salt (0.680 mmol, 85%). LCMS RT=2.38 min (Method A); ESI-MS m/z 763.71 $[M+H]^+$; HRMS m/z 763.4633 $[C_{38}H_{63}N_8O_6Cl+H]^+$.

Example 30

(2S,3S)-3-azido-N-((3R,4S,5S)-1-((S)-2-((1R,2R)-3-((2-chlorophenethyl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N-methylbutanamide

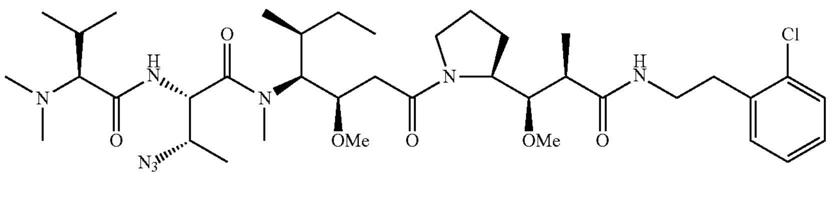 [SMILES: CC[C@H](C)[C@@H]([C@@H](CC(=O)N1CCC[C@H]1[C@H](OC)[C@@H](C)C(=O)NCCc1ccccc1Cl)OC)N(C)C(=O)[C@@H](NC(=O)[C@H](C(C)C)N(C)C)[C@H](C)N=[N+]=[N-]]

To a stirred room temperature solution of Boc-Dap-OH dicyclohexylamine salt (5.00 g, 10.7 mmol) and 2-(2-chlorophenyl)ethylamine (1.85 g, 11.7 mmol) in $CH_2Cl_2$ (10 mL) was added DIEA (4.76 mL, 26.7 mmol) and DEPC (2.41 mL, 16.0 mmol). After 10 h, analysis by LCMS showed the reaction was complete. The volatile organic were evaporated in vacuo to give crude product that was used without further purification. A total of 3.98 g of Boc-Dap-2-(2-chlorophenyl)ethylamine (9.37 mmol, 88%) was obtained. LCMS RT=3.04 min (Method A); ESI-MS m/z 425.23 $[M+H]^+$.

To a stirred room temperature solution of Boc-Dap-2-(2-chlorophenyl)ethylamine (3.98 g, 9.37 mmol) in $CH_2Cl_2$ (5 mL) was added TFA (5 mL). After 10 h, analysis by LCMS showed the reaction was complete. The crude oil was purified by preparatory RP-HPLC with a Phenomenex Synergi 10 Max-RP 80 Å column (150×30 mm) using 10% to 90% MeCN in 0.05% aqueous TFA as the eluent. A total of 2.87 g of H-Dap-2-(2-chlorophenyl)ethylamine (6.55 mmol, 70%) was prepared as the TFA salt. LCMS RT=1.83 min (Method A); ESI-MS m/z 325.22 $[M+H]^+$.

To a stirred room temperature solution of Dov-Abu(3-$N_3$)-Dil-OH TFA salt (0.450 g, 0.789 mmol) and H-Dap-2-(2-chlorophenyl)ethylamine TFA salt (0.320 g, 0.731 mmol) in DMF (10 mL) was added DIEA (0.515 mL, 2.96 mmol), followed by the addition of HATU (0.751 g, 1.97 mmol). After 10 h, analysis by LCMS showed the reaction was complete. The crude reaction mixture was purified by preparatory RP-HPLC with a Phenomenex Synergi 10μ Max-RP 80 Å column (150×30 mm) using 10% to 90% MeCN in 0.05% aqueous TFA as the eluent. A total of 253 mg of the title compound was obtained as the TFA salt (0.289 mmol, 32% based on RSM). LCMS RT=1.26 min (Method B); ESI-MS m/z 763.60 $[M+H]^+$; HRMS m/z 763.4632 $[C_{38}H_{63}N_8O_6Cl+H]^+$.

Example 31

(2S,3S)-3-amino-2-((S)-2-(dimethylamino)-3-methylbutanamido)-N-((3R,4S,5S)-3-methoxy-1-((S)-2-((1R,2R)-1-methoxy-2-methyl-3-oxo-3-(phenethylamino)propyl)pyrrolidin-1-yl)-5-methyl-1-oxoheptan-4-yl)-N-methylbutanamide

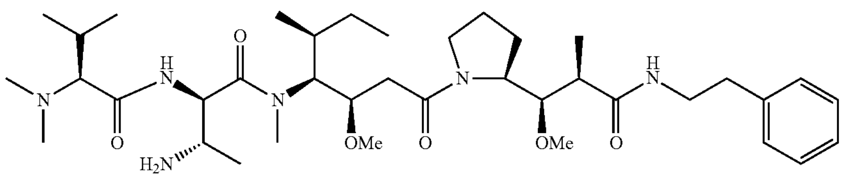 [SMILES: CC[C@H](C)[C@@H]([C@@H](CC(=O)N1CCC[C@H]1[C@H](OC)[C@@H](C)C(=O)NCCc1ccccc1)OC)N(C)C(=O)[C@H](NC(=O)[C@H](C(C)C)N(C)C)[C@H](C)N]

To a stirred room temperature solution of Dov-Abu(3-$N_3$)-Dil-Dap-PE TFA salt (25 mg, 0.030 mmol) in THF (0.5 mL) was added trimethylphosphine in THF (1 M, 0.045 mL, 0.045 mmol). After 1 h, analysis by LCMS showed the reaction was complete. The crude reaction mixture was purified by preparatory RP-HPLC with a Phenomenex Synergi 10μ Max-RP 80 Å column (150×30 mm) using 5% to 95% MeCN in 0.1% aqueous formic acid as the eluent. A total of 9.0 mg of the title compound was obtained as the formic acid salt (0.012 mmol, 41%). LCMS RT=1.02 min (Method B); ESI-MS m/z 703.71 $[M+H]^+$; HRMS m/z 703.5117 $[C_{38}H_{66}N_6O_6+H]^+$.

Example 32

(2S,3S)-3-amino-2-((S)-2-(dimethylamino)-3-methylbutanamido)-N-((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N-methylbutanamide

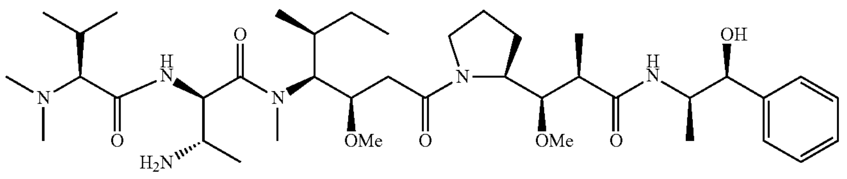 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@H](NC(=O)[C@H](C(C)C)N(C)C)[C@H](C)N]

To a stirred room temperature solution of Dov-Abu(3-$N_3$)-Dil-Dap-Norephedrine TFA salt (27 mg, 0.031 mmol) in THF (0.3 mL) was added trimethylphosphine in THF (1 M, 0.046 mL, 0.046 mmol). After 2 h, analysis by LCMS showed the reaction was complete. The crude reaction mixture was purified by preparatory RP-HPLC with a Phenomenex Synergi 10 Max-RP 80 Å column (150x30 mm) using 10% to 90% MeCN in 0.05% aqueous trifluoroacetic acid as the eluent. A total of 6.8 mg of the title compound was obtained as the TFA salt (0.008 mmol, 26%). LCMS RT=1.95 min (Method B); ESI-MS m/z 733.72 $[M+H]^+$; HRMS m/z 733.5227 $[C_{39}H_{68}N_6O_7+H]^+$.

Example 33

(2S,3S)-3-amino-N-((3R,4S,5S)-1-((S)-2-((1R,2R)-3-((4-chlorophenethyl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N-methylbutanamide

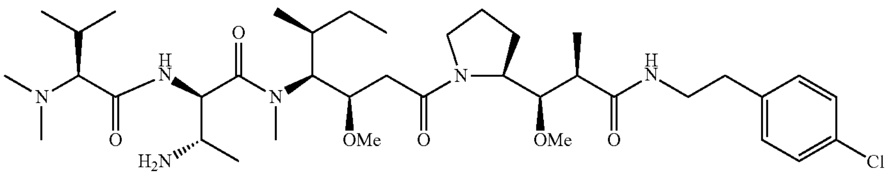 [SMILES: CC[C@H](C)[C@@H]([C@@H](CC(=O)N1CCC[C@H]1[C@H](OC)[C@@H](C)C(=O)NCCc1ccc(Cl)cc1)OC)N(C)C(=O)[C@H](NC(=O)[C@H](C(C)C)N(C)C)[C@H](C)N]

To a stirred room temperature solution of Dov-Abu(3-$N_3$)-Dil-Dap-2-(4-chlorophenyl)ethylamine TFA salt (117 mg, 0.133 mmol) in THF (0.3 mL) was added trimethylphosphine in THF (1 M, 0.2 mL, 0.2 mmol). After 2 h, analysis by LCMS showed the reaction was complete. The crude reaction mixture was purified by preparatory RP-HPLC with a Phenomenex Synergi 10 Max-RP 80 Å column (150x30 mm) using 5% to 95% MeCN in 0.1% aqueous formic acid as the eluent. A total of 9.0 mg of the title compound was obtained as the formic acid salt (0.011 mmol, 9%). LCMS RT=0.97 min (Method B); ESI-MS m/z 737.51 $[M+H]^+$; HRMS m/z 737.4731 $[C_{38}H_{65}N_6O_6Cl+H]^+$.

Example 34

(2S,3S)-3-amino-N-((3R,4S,5S)-1-((S)-2-((1R,2R)-3-((2-chlorophenethyl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N-methylbutanamide

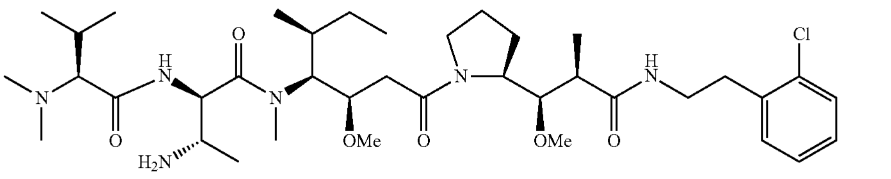 [SMILES: CC[C@H](C)[C@@H]([C@@H](CC(=O)N1CCC[C@H]1[C@H](OC)[C@@H](C)C(=O)NCCc1ccccc1Cl)OC)N(C)C(=O)[C@H](NC(=O)[C@H](C(C)C)N(C)C)[C@H](C)N]

To a stirred room temperature solution of Dov-Abu(3-$N_3$)-Dil-Dap-2-(2-chlorophenyl)ethylamine formic acid salt (46 mg, 0.057 mmol) in THF (1.0 mL) was added trimethylphosphine in THF (1 M, 0.085 mL, 0.085 mmol). After 1 h, the crude reaction mixture was purified by preparatory RP-HPLC with a Phenomenex Synergi 10 Max-RP 80 Å column (150×30 mm) using 5% to 95% MeCN in 0.1% aqueous formic acid as the eluent. A total of 13.6 mg of the title compound was obtained as the formic acid salt (0.017 mmol, 30%). LCMS RT=1.03 min (Method B); ESI-MS m/z 737.57 $[M+H]^+$; HRMS m/z 737.4731 $[C_{38}H_{65}N_6O_6Cl+H]^+$.

Example 35

(S)-4-amino-2-((S)-2-(dimethylamino)-3-methylbutanamido)-N-((3R,4S,5S)-3-methoxy-1-((S)-2-((1R,2R)-1-methoxy-2-methyl-3-oxo-3-(phenethylamino)propyl)pyrrolidin-1-yl)-5-methyl-1-oxoheptan-4-yl)-N-methylbutanamide

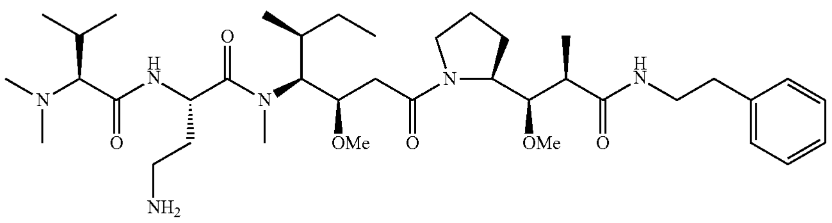 [SMILES: CC[C@H](C)[C@@H]([C@@H](CC(=O)N1CCC[C@H]1[C@H](OC)[C@@H](C)C(=O)NCCc1ccccc1)OC)N(C)C(=O)[C@H](CCN)NC(=O)[C@H](C(C)C)N(C)C]

To a stirred room temperature solution of Dov-Dab(Fmoc)-Dil-OH TFA salt (0.450 g, 0.587 mmol) and H-Dap-phenethylamine TFA salt (0.200 g, 0.495 mmol) in DMF (15 mL) was added DIEA (0.360 mL, 2.07 mmol), followed by the addition of HATU (0.526 g, 1.38 mmol). After 10 h, analysis by LCMS showed the reaction was complete. The crude reaction mixture was diluted with saturated sodium bicarbonate (10 mL) and extracted with EtOAc (20 mL×2). The combined organic fractions were washed with brine, dried using magnesium sulfate, filtered, and concentrated in vacuo. The crude oil was purified by preparatory RP-HPLC with a Phenomenex Synergi 10 Max-RP 80 Å column (150×30 mm) using 10% to 90% MeCN in 0.1% aqueous formic acid as the eluent. A total of 276 mg of Dov-Dab(Fmoc)-Dil-Dap-phenethylamine (0.266 mmol, 54%) was obtained as the formic acid salt. LCMS RT=1.37 min (Method B); ESI-MS m/z 925.48 $[M+H]^+$.

To a stirred room temperature solution of Dov-Dab(Fmoc)-Dil-Dap-phenethylamine (0.276 g, 0.266 mmol) in acetonitrile (10 mL) was added piperidine (5 mL). After 10 h, analysis by LCMS showed the reaction was complete. To the crude reaction mixture was added hexanes. The acetonitrile layer was concentrated in vacuo. The crude oil was purified by preparatory RP-HPLC with a Phenomenex Synergi 10 Max-RP 80 Å column (150×30 mm) using 10% to 90% MeCN in 0.1% aqueous formic acid as the eluent. A total of 98.0 mg of the title compound was obtained as a formic acid salt (0.120 mmol, 45%). LCMS RT=1.02 min (Method B); ESI-MS m/z 703.78 $[M+H]^+$; HRMS m/z 703.5117 $[C_{38}H_{66}N_6O_6+H]^+$.

Example 36

(S)-4-amino-2-((S)-2-(dimethylamino)-3-methylbutanamido)-N-((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N-methylbutanamide

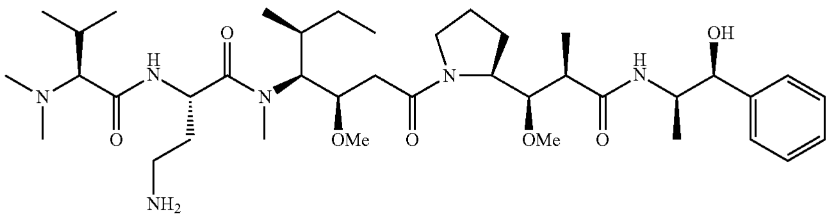 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@H](CCN)NC(=O)[C@H](C(C)C)N(C)C]

To a stirred room temperature solution of Dov-Dab(Fmoc)-Dil-OH TFA salt (0.459 g, 0.599 mmol) and H-Dap-(1R,2S)-(−)-Norephedrine TFA salt (0.225 g, 0.518 mmol) in DMF (15 mL) was added DIEA (0.376 mL, 2.11 mmol), followed by the addition of HATU (0.536 g, 1.41 mmol). After 10 h, analysis by LCMS showed the reaction was complete. The crude reaction mixture was diluted with saturated sodium bicarbonate (10 mL) and extracted with EtOAc (20 mL×2). The combined organic fractions were washed with brine, dried using magnesium sulfate, filtered, and concentrated in vacuo. The crude oil was purified by preparatory RP-HPLC with a Phenomenex Synergi 10μ Max-RP 80 Å column (150×30 mm) using 10% to 90% MeCN in 0.1% aqueous formic acid as the eluent. A total of 449 mg of Dov-Dab(Fmoc)-Dil-Dap-(1R,2S)-(−)-Norephedrine (0.420 mmol, 81%) was obtained as the formic acid salt. LCMS RT=1.35 min (Method B); ESI-MS m/z 955.74 $[M+H]^+$.

To a stirred room temperature solution of Dov-Dab(Fmoc)-Dil-Dap-(1R,2S)-(−)-Norephedrine formic acid salt (0.449 g, 0.420 mmol) in acetonitrile (10 mL) was added piperidine (5 mL). After 10 h, analysis by LCMS showed the reaction was complete. To the crude reaction mixture was added hexanes. The acetonitrile layer was concentrated in vacuo. The crude oil was purified by preparatory RP-HPLC with a Phenomenex Synergi 10μ Max-RP 80 Å column (150×30 mm) using 10% to 90% MeCN in 0.1% aqueous formic acid as the eluent. A total of 53.0 mg of the title compound was obtained as a formic acid salt (0.068 mmol, 14%). LCMS RT=0.79 min (Method B); ESI-MS m/z 733.71 $[M+H]^+$; HRMS m/z 733.5227 $[C_{39}H_{68}N_6O_7+H]^+$.

Example 37

(S)-4-amino-N-((3R,4S,5S)-1-((S)-2-((1R,2R)-3-((4-chlorophenethyl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N-methylbutanamide

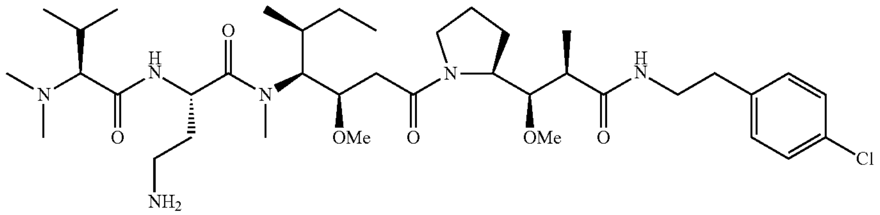 [SMILES: CC[C@H](C)[C@@H]([C@@H](CC(=O)N1CCC[C@H]1[C@H](OC)[C@@H](C)C(=O)NCCc1ccc(Cl)cc1)OC)N(C)C(=O)[C@H](CCN)NC(=O)[C@H](C(C)C)N(C)C]

To a stirred room temperature solution of Dov-Dab (Fmoc)-Dil-OH TFA salt (0.255 g, 0.333 mmol) and H-Dap-2-(4-chlorophenyl)ethylamine TFA salt (0.127 g, 0.290 mmol) in DMF (10 mL) was added DIEA (0.204 mL, 1.17 mmol), followed by the addition of HATU (0.298 g, 0.781 mmol). After 10 h, analysis by LCMS showed the reaction was complete. The crude reaction mixture was diluted with saturated sodium bicarbonate (10 mL) and extracted with EtOAc (20 mL×2). The combined organic fractions were washed with brine, dried using magnesium sulfate, filtered, and concentrated in vacuo. The crude oil was purified by preparatory RP-HPLC with a Phenomenex Synergi 10μ. Max-RP 80 Å column (150×30 mm) using 10% to 90% MeCN in 0.1% aqueous formic acid as the eluent. A total of 190 mg of Dov-Dab(Fmoc)-Dil-Dap-2-(4-chlorophenyl)ethylamine (0.177 mmol, 61%) was obtained as the formic acid salt. LCMS RT=1.49 min (Method B); ESI-MS m/z 959.62 $[M+H]^+$.

To a stirred room temperature solution of Dov-Dab (Fmoc)-Dil-Dap-2-(4-chlorophenyl)ethylamine formic acid salt (0.190 g, 0.177 mmol) in acetonitrile (5 mL) was added piperidine (5 mL). After 10 h, analysis by LCMS showed the reaction was complete. To the crude reaction mixture was added hexanes. The acetonitrile layer was concentrated in vacuo. The crude oil was purified by preparatory RP-HPLC with a Phenomenex Synergi 10 Max-RP 80 Å column (150×30 mm) using 10% to 90% MeCN in 0.1% aqueous formic acid as the eluent. A total of 118 mg of the title compound was obtained as a formic acid salt (0.151 mmol, 85%). LCMS RT=1.06 min (Method B); ESI-MS m/z 737.55 $[M+H]^+$; HRMS m/z 737.4729 $[C_{38}H_{65}N_6O_6Cl+H]^+$.

Example 38

(S)-4-amino-N-((3R,4S,5S)-1-((S)-2-((1R,2R)-3-((2-chlorophenethyl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N-methylbutanamide

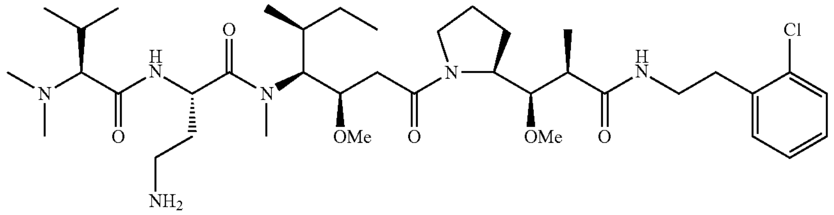 [SMILES: CC[C@H](C)[C@@H]([C@@H](CC(=O)N1CCC[C@H]1[C@H](OC)[C@@H](C)C(=O)NCCc1ccccc1Cl)OC)N(C)C(=O)[C@H](CCN)NC(=O)[C@H](C(C)C)N(C)C]

To a stirred room temperature solution of Dov-Dab (Fmoc)-Dil-OH TFA salt (0.306 g, 0.399 mmol) and H-Dap-2-(2-chlorophenyl)ethylamine TFA salt (0.170 g, 0.388 mmol) in DMF (5 mL) was added DIEA (0.300 g, 400 μL, 2.29 mmol), followed by the addition of HATU (360 mg, 0.944 mmol). After 10 h, analysis by LCMS showed the reaction was complete. The crude reaction was diluted with saturated sodium bicarbonate (10 mL) and extracted with EtOAc (10 mL×3). The combined organic fractions were washed with brine, dried over a pad of magnesium sulfate, filtered, and concentrated in vacuo. The crude oil was purified by preparatory RP-HPLC with a Phenomenex Gemini 10μ Max-RP 110 Å column (150×30 mm) using 10% to 90% MeCN in 0.1% aqueous $NH_4OH$ as the eluent. A total of 115 mg of Dov-Dab(Fmoc)-Dil-Dap-2-(2-chlorophenyl)ethylamine (0.120 mmol, 26%) was obtained as a white solid. LCMS RT=1.40 min (Method B); ESI-MS m/z 959.75 $[M+H]^+$.

To a stirred room temperature solution of Dov-Dab (Fmoc)-Dil-Dap-2-(2-chlorophenyl)ethylamine (0.115 g, 0.120 mmol) in acetonitrile (10 mL) was added piperidine (2 mL). After 3 h, analysis by LCMS showed the reaction was complete. To the crude reaction mixture was added hexanes. The acetonitrile layer was concentrated in vacuo. The crude oil was purified by preparatory RP-HPLC with a Phenomenex Synergi 10μ Max-RP 80 Å column (150×30 mm) using 10% to 90% MeCN in 0.1% aqueous $NH_4OH$ as the eluent. A total of 30.0 mg of the title compound was obtained as a white solid (0.041 mmol, 34%). LCMS RT=1.15 min (Method B); ESI-MS m/z 737.68 $[M+H]^+$; HRMS m/z 737.4729 $[C_{38}H_{65}N_6O_6Cl+H]^+$.

Example 39 methyl ((2R,3R)-3-((S)-1-((3R,4S,5S)-4-((S)-2-((S)-2-(dimethylamino)-3-methylbutanamido)-N-methylpent-4-ynamido)-3-methoxy-5-methylheptanoyl)pyrrolidin-2-yl)-3-methoxy-2-methylpropanoyl)-L-phenylalaninate

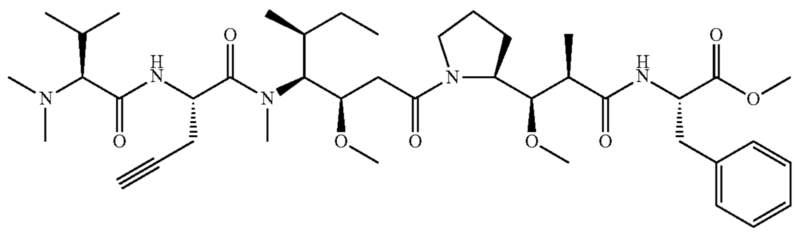

To a stirred 25° C. solution of Boc-propargylGly-OH (1.00 g, 4.69 mmol) and H-Dil-OtBu HCl salt (1.15 g, 3.90 mmol) in EtOAc (10 mL) was added DIEA (1.49 mL, 9.38 mmol). The solution was cooled to (0° C.) and stirred for 20 min and an additional portion of DIEA (1.49 mL, 9.38 mmol) was added and the reaction mixture stirred at 0° C. 20 min. Then CMPI (1.80 g, 7.04 mmol) was added to the reaction mixture which was allowed to warm to room temperature and stirred for 12 h. The crude reaction mixture was washed with 0.1 M HCl (20 mL×2), followed by brine (20 mL×2). The organic fraction was dried over anhydrous magnesium sulfate, filtered, and concentrated in vacuo to give the crude product. A total of 2.05 g of Boc-propargylGly-Dil-OtBu was obtained (4.50 mmol, 96%). LCMS RT=3.46 min (Method A); ESI-MS m/z 455.42 $[M+H]^+$.

To a stirred 25° C. solution of Boc-propargylGly-Dil-OtBu (2.05 g, 4.50 mmol) in $CH_2Cl_2$ (6 mL) was added TFA (6 mL). After 14 h, analysis by LCMS showed the reaction was complete. The volatile organics were concentrated in vacuo to give crude product that was used without further purification. A total of 1.30 g of H-propargylGly-Dil-OH was obtained as the TFA salt (3.16 mmol, 70%).

To a stirred 25° C. solution of Dov (1.27 g, 8.71 mmol) in DMF (10 mL) was added DIEA (2.33 mL, 13.1 mmol), followed by HATU (3.32 g, 8.71 mmol). After 10 min, a solution of H-propargylGly-Dil-OH TFA salt (1.30 g, 3.16 mmol) in DMF was added to the reaction. After 8 h, analysis by LCMS showed the reaction was complete. The crude oil was purified by preparatory RP-HPLC with a Phenomenex Synergi 10μ Max-RP 80 Å column (150×30 mm) using 10% to 90% MeCN in 0.05% aqueous TFA as the eluent. A total of 455 mg of Dov-propargyGly-Dil-OH was obtained as the TFA salt (0.844 mmol, 27% yield). LCMS RT=1.65 min (Method A); ESI-MS m/z 425.95 $[M+H]^+$.

To a stirred room temperature solution of Dov-propargylGly-Dil-OH TFA salt (0.198 g, 0.367 mmol) and H-Dap-Phe-OMe TFA salt (0.156 g, 0.338) in DMF (10 mL) was added DIEA (0.222 mL, 1.40 mmol), followed by the addition of HATU (0.355 g, 0.931 mmol). After 10 h, analysis by LCMS showed the reaction was complete. The crude reaction was diluted with saturated sodium bicarbonate (10 mL) and extracted with EtOAc (20 mL×2). The combined organic fractions were washed with brine, dried using magnesium sulfate, filtered, and concentrated in vacuo. The crude oil was purified by preparatory RP-HPLC with a Phenomenex Synergi 10μ Max-RP 80 Å column (150×30 mm) using 10% to 90% MeCN in 0.05% aqueous TFA as the eluent. A total of 10.0 mg of the title compound was obtained as the TFA salt (0.012 mmol, 3%). LCMS RT=2.50 min (Method A); ESI-MS m/z 756.44 $[M+H]^+$; HRMS m/z 756.4902 $[C_{41}H_{65}N_5O_8+H]^+$.

Example 40

(2S,3S)—N-((3R,4S,5S)-1-((S)-2-((1R,2R)-3-(((S)-1-amino-1-oxo-3-phenylpropan-2-yl)amino)-1-methoxy-2-methyl-3-oxopropyl)pyrrolidin-1-yl)-3-methoxy-5-methyl-1-oxoheptan-4-yl-3-azido-2-((S)-2-(dimethylamino)-3-methylbutanamido)-N-methylbutanamide

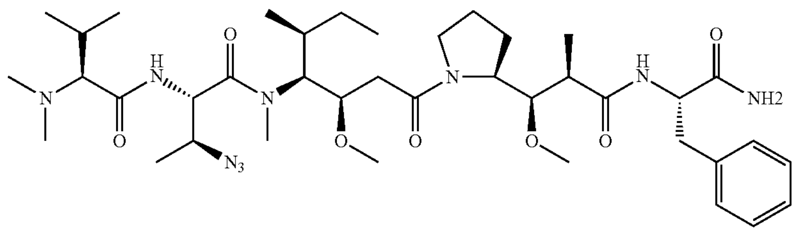 [SMILES: CC[C@H](C)[C@@H]([C@@H](CC(=O)N1CCC[C@H]1[C@H](OC)[C@@H](C)C(=O)N[C@@H](Cc1ccccc1)C(N)=O)OC)N(C)C(=O)[C@@H](NC(=O)[C@H](C(C)C)N(C)C)[C@H](C)N=[N+]=[N-]]

To a stirred room temperature solution of Dov-Abu(3-$N_3$)-Dil-Dap-Phe-OH formic acid salt (42.1 mg, 0.051 mmol), ammonium chloride (7.9 mg, 0.148 mmol), TBTU (52.5 mg, 0.163 mmol) in DMF (0.2 mL) was added Hunig's base (0.045 mL, 0.258 mmol). After 16 h, analysis by LCMS showed the reaction was complete. The crude reaction mixture was purified by preparatory RP-HPLC with a Phenomenex Gemini-NX 10μ C-18 110 Å column (150×30 mm) using 5% to 95% MeCN in 0.1% aqueous ammonium hydroxide as the eluent. A total of 13.4 mg of the title compound was obtained (0.017 mmol, 33%). LCMS RT=1.05 min (Method B); ESI-MS m/z 772.61 $[M+H]^+$; HRMS m/z 772.5078 $[C_{39}H_{65}N_9O_7+H]^+$.

Example 41

(2S,3S)-3-azido-2-((S)-2-(dimethylamino)-3-methylbutanamido)-N-((3R,4S,5S)-3-methoxy-1-((S)-2-((1R,2R)-1-methoxy-2-methyl-3-oxo-3-((2-(pyridin-2-yl)ethyl)amino)propyl)pyrrolidin-1-yl)-5-methyl-1-oxoheptan-4-yl)-N-methylbutanamide

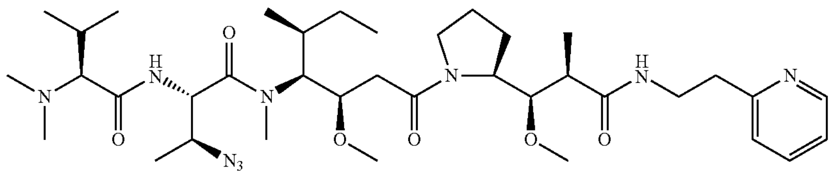 [SMILES: CC[C@H](C)[C@@H]([C@@H](CC(=O)N1CCC[C@H]1[C@H](OC)[C@@H](C)C(=O)NCCc1ccccn1)OC)N(C)C(=O)[C@@H](NC(=O)[C@H](C(C)C)N(C)C)[C@H](C)N=[N+]=[N-]]

To a stirred 23° C. solution of Dov-Abu(3-$N_3$)-Dil-OH TFA salt (0.300 g, 0.526 mmol) and H-Dap-2-(2-pyridyl) ethylamine TFA salt (0.287 g, 0.709 mmol) in DMF (10 mL) was added DIEA (343 μL, 1.97 mmol) followed by the addition of HATU (0.501 g, 1.31 mmol). After 10 h, analysis by LCMS showed the reaction was complete. The crude reaction was diluted with saturated sodium bicarbonate (10 mL) and extracted with EtOAc (20 mL×2). The combined organic fractions were washed with brine, dried over a pad of magnesium sulfate, filtered, and concentrated in vacuo. The crude oil was purified by preparatory RP-HPLC with a Phenomenex Gemini-NX 10μ C-18 110 Å column (150×30 mm) using 10% to 90% MeCN in 0.1% aqueous $NH_4OH$ as the eluent. A total of 139 mg of the title compound was obtained (0.190 mmol, 29%). LCMS RT=0.916 min (Method B); ESI-MS m/z 730.64 $[M+H]^+$; HRMS m/z 730.4985 $[C_{37}H_{63}N_9O_6+H]^+$.

Example 42

(2S,3S)-3-azido-N-((3R,4S,5S)-1-((S)-2-((1R,2R)-3-(((S)-1-(tert-butylamino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N-methylbutanamide

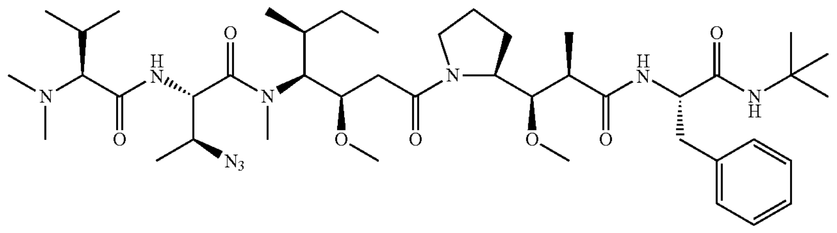 [SMILES: CC[C@H](C)[C@@H]([C@@H](CC(=O)N1CCC[C@H]1[C@H](OC)[C@@H](C)C(=O)N[C@@H](Cc1ccccc1)C(=O)NC(C)(C)C)OC)N(C)C(=O)[C@@H](NC(=O)[C@H](C(C)C)N(C)C)[C@H](C)N=[N+]=[N-]]

To a stirred room temperature solution of Dov-Abu(3-$N_3$)-Dil-Dap-Phe-OH formic acid salt (24.0 mg, 0.029 mmol), tert-butyl amine hydrochloride (7.9 mg, 0.072 mmol), HATU (24.5 mg, 0.064 mmol) in DMF (0.2 mL) was added Hunig's base (0.022 mL, 0.124 mmol). After 18 h, analysis by LCMS showed the reaction was complete. The crude reaction mixture was purified by preparatory RP-HPLC with a Phenomenex Gemini-NX 10μ C-18 110 Å column (150×30 mm) using 5% to 95% MeCN in 0.1% aqueous ammonium hydroxide as the eluent. A total of 15.4 mg of the title compound was obtained (0.017 mmol, 59%). LCMS RT=1.27 min (Method B); ESI-MS m/z 828.8 $[M+H]^+$; HRMS m/z 828.5671 $[C_{39}H_{66}N_6O_8+H]^+$.

Example 43 methyl ((2R,3R)-3-((S)-1-((3R,4S,5S)-4-((2S,3S)-3-azido-2-((S)-2-(dimethylamino)-3-methylbutanamido)-N-methylbutanamido)-3-methoxy-5-methylheptanoyl)pyrrolidin-2-yl)-3-methoxy-2-methylpropanoyl)-L-valinate

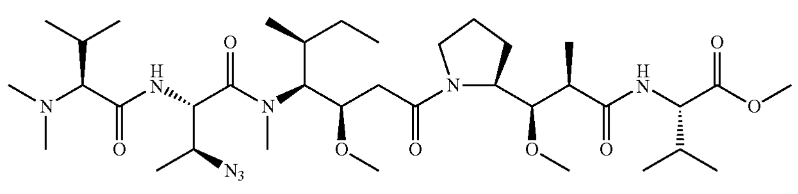

To a stirred 23° C. suspension of Boc-Dap-OH dicyclohexylamine (4.00 g, 8.54 mmol) and H-Val-OMe HCl salt (1.80 g, 10.7 mmol) in $CH_2C_2$ (20 mL) was added DIEA (4.44 g, 6.00 mL, 34.4 mmol), followed by the addition of HATU (2.15 g, 2.00 mL, 0.013 mol). After 10 h, analysis by LCMS showed the reaction was complete. The volatile organics were evaporated in vacuo to give crude product, that was used without further purification. A total of 6.80 g of Boc-Dap-Val-OMe was obtained as a colorless oil (17.0 mmol, 80%). LCMS RT=1.33 min (Method B); ESI-MS m/z 401.6 $[M+H]^+$.

A 23° C. suspension of Boc-Dap-Val-OMe (6.80 g, 17.0 mmol) in 4.0 M HCl in dioxane (20 mL) was stirred. After 4 h, analysis by LCMS showed the reaction was complete. The volatile organics were evaporated in vacuo to give crude product that was used without further purification. A total of 4.57 g of H-Dap-Val-OMe was obtained as the HCl salt (13.6 mmol, 80%). LCMS RT=0.726 min (Method B); ESI-MS m/z 301.45 $[M+H]^+$.

To a stirred 23° C. suspension of Dov-Abu(3-$N_3$)-Dil-OH TFA salt (0.144 g, 0.253 mmol) and H-Dap-Val-OMe HCl salt (0.332 g, 0.985 mmol) in DMF (10 mL) was added DIEA (0.222 g, 0.300 mL, 1.72 mmol), followed by the addition of HATU (0.240 g, 0.631 mmol). After 10 h, analysis by LCMS showed the reaction was complete. The crude reaction was diluted with saturated sodium bicarbonate (10 mL) and extracted with EtOAc (20 mL×3). The combined organic fractions were washed with brine, dried over a pad of magnesium sulfate, filtered, and concentrated in vacuo. The crude oil was purified by preparatory RP-HPLC with a Phenomenex Gemini-NX 10μ C-18 110 Å column (150×30 mm) using 5% to 90% MeCN in 0.1% aqueous $NH_4OH$ as the eluent. A total of 129 mg of the title compound was obtained as a pale yellow solid (0.175 mmol, 55%). LCMS RT=1.15 min (Method B); ESI-MS m/z 739.75 $[M+H]^+$; HRMS m/z 739.5074 $[C_{36}H_{66}N_8O_8+H]^+$.

Example 44 methyl ((2R,3R)-3-((S)-1-((3R,4S,5S)-4-((S)-6-amino-2-((S)-2-(dimethylamino)-3-methylbutanamido)-N-methylhexanamido)-3-methoxy-5-methylheptanoyl)pyrrolidin-2-yl)-3-methoxy-2-methylpropanoyl)-L-phenylalaninate

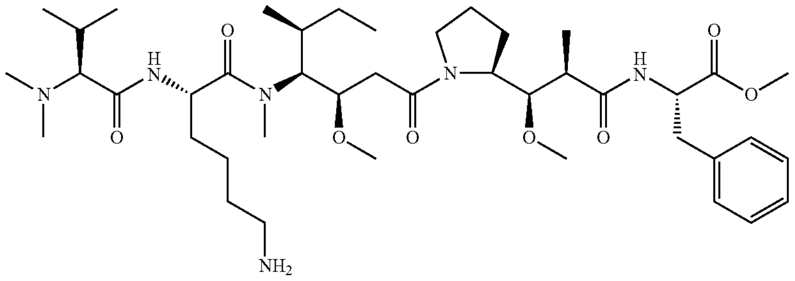

To a stirred 23° C. suspension of Boc-Lys(Fmoc)-OH (5.60 g, 12.0 mmol) and H-Dil-OtBu HCl (3.06 g, 10.9 mmol) in EtOAc (20 mL) was added DIEA (4.44 g, 6.00 mL, 34.4 mmol). The solution was cooled to 0° C. and stirred for 0.5 h. After 0.5 h, additional DIEA (4.44 g, 6.00 mL, 34.4 mmol) was added to the reaction mixture and the 0° C. reaction was stirred for 0.5 h. Then CMPI (4.20 g, 16.4 mmol) was added to the reaction mixture which was allowed to slowly warm to room temperature and stirred for 10 h. The crude reaction was washed with 1 M HCl (30 mL×2), followed by brine (25 mL×2). The organic fraction was dried over a pad of magnesium sulfate, filtered, and concentrated in vacuo. A total of 7.38 g of Boc-Lys(Fmoc)-Dil-OtBu was obtained as a pale yellow solid (10.4 mmol, 86%). LCMS RT=1.85 min (Method B); ESI-MS m/z 710.1 $[M+H]^+$.

A 23° C. suspension of Boc-Lys(Fmoc)-Dil-OtBu (7.38 g, 10.4 mmol) in 4.0 M HCl in dioxane (10.0 mL) was stirred. After 10 h, analysis by LCMS showed the reaction was complete. The volatile organics were evaporated in vacuo to give crude product that was used without further purification. A total of 7.05 g of H-Lys(Fmoc)-Dil-OH was obtained as a pale yellow HCl salt (0.012 mol, 89%). LCMS RT=1.20 min (Method B); ESI-MS m/z 554.54 $[M+H]^+$.

To a stirred 23° C. suspension of Dov-OH (2.50 g, 17.2 mmol) in DMF (20 mL) was added DIEA (4.44 g, 6.00 mL, 0.034 mol), followed by the addition of HATU (4.82 g, 12.6 mmol). After 5 min, H-Lys(Fmoc)-Dil-OH HCl salt (7.05 g, 0.012 mol) was added to the reaction mixture. After 4 h, analysis by LCMS showed the reaction was complete. The crude reaction mixture was diluted with saturated sodium bicarbonate (10 mL) and extracted with EtOAc (20 mL×2). The combined organic fractions were washed with brine, dried over a pad of magnesium sulfate, filtered, and concentrated in vacuo. The crude oil was purified by preparatory RP-HPLC with a Phenomenex Gemini NX-C18 10μ 110 Å column (150×30 mm) using 5% to 95% MeCN in 0.1% aqueous $NH_4OH$ as the eluent. A total of 4.45 g of Dov-Lys(Fmoc)-Dil-OH was obtained as a pale yellow solid (6.54 mmol, 78%). LCMS RT=1.21 min (Method B); ESI-MS m/z 681.68 $[M+H]^+$.

To a stirred 23° C. suspension of Dov-Lys(Fmoc)-Dil-OH (2.17 g, 3.19 mmol) and H-Dap-OMe TFA salt (1.78 g, 3.85 mmol) in DMF (10 mL) was added DIEA (1.65 g, 2.20 mL, 12.7 mmol), followed by the addition of HATU (1.94 g, 5.10 mmol). After 10 h, analysis by LCMS showed the reaction was complete. The crude reaction was diluted with saturated sodium bicarbonate (10 mL) and extracted with EtOAc (20 mL×3). The combined organic fractions were washed with brine, dried over a pad of magnesium sulfate, filtered, and concentrated in vacuo. The crude oil was purified by preparatory RP-HPLC with a Phenomenex Gemini 10μ Max-RP 110 Å column (150×30 mm) using 5% to 90% MeCN in 0.1% aqueous $NH_4OH$ as the eluent. A total of 2.25 g of Dov-Lys(Fmoc)-Dil-Dap-Phe-OMe was obtained as a pale yellow solid (2.23 mmol, 70%). LCMS RT=1.29 min (Method B); ESI-MS m/z 1011.77 $[M+H]^+$.

To a stirred 23° C. suspension of Dov-Lys(Fmoc)-Dil-Dap-Phe-OMe (2.25 g, 2.23 mmol) in acetonitrile (20 mL) was added piperidine (5 mL). After 2 h, analysis by LCMS showed the reaction was complete. To the crude reaction solution was added hexanes. The acetonitrile layer was concentrated in vacuo. The crude oil was purified by preparatory RP-HPLC with a Phenomenex Gemini NX-C18 10μ 110 Å column (150×30 mm) using 5% to 95% MeCN in 0.1% aqueous $NH_4OH$ as the eluent. A total of 898 mg of the title compound was obtained as a white solid (1.14 mmol, 51%). LCMS RT=0.840 min (Method B); ESI-MS m/z 789.5 $[M+H]^+$; HRMS m/z 789.5482 $[C_{42}H_{72}N_6O_8+H]^+$.

Example 45 methyl ((2R,3R)-3-((S)-1-((3R,4S,5S)-4-((2S,4S)-4-azido-1-(dimethyl-L-valyl)-N-methylpyrrolidine-2-carboxamido)-3-methoxy-5-methylheptanoyl)pyrrolidin-2-yl)-3-methoxy-2-methylpropanoyl)-L-phenylalaninate

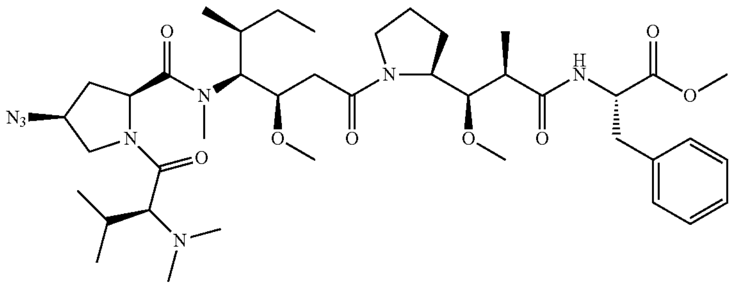 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H]1C[C@H](N=[N+]=[N-])CN1C(=O)[C@H](C(C)C)N(C)C]

To a stirred 23° C. suspension of cis-Fmoc-Pro(4-$N_3$)—OH (2.00 g, 5.27 mmol) and H-Dil-OtBu HCl (1.49 g, 5.27 mmol) in EtOAc (20 mL) was added DIEA (2.22 g, 3.0 mL, 17.2 mmol). The solution was cooled to 0° C. and stirred for 0.5 h. To the cooled reaction mixture was added additional DIEA (2.22 g, 3.0 mL, 17.2 mmol) and the 0° C. reaction mixture was stirred for 0.5 h. Then CMPI (2.03 g, 7.93 mmol) was added to the reaction mixture which was allowed to slowly warm to room temperature and stirred for 10 h. The crude reaction was washed with 1 M HCl (30 mL×2), followed by brine (25 mL×2). The organic fraction was dried over a pad of magnesium sulfate, filtered, and concentrated in vacuo. The crude product was used without further purification. A total of 3.13 g of cis-Fmoc-Pro(4-$N_3$)-Dil-OtBu was obtained as a yellow oil (5.05 mmol, 76%). LCMS RT=1.73 min (Method B); ESI-MS m/z 621.46 $[M+H]^+$.

To a stirred 23° C. solution of cis-Fmoc-Pro(4-$N_3$)-Dil-OtBu (3.13 g, 4.04 mmol) in acetonitrile (20 mL) was added piperidine (10 mL). After 10 h, analysis by LCMS showed the reaction was complete. To the crude reaction mixture was added hexanes. The acetonitrile layer was concentrated in vacuo and the crude product was used without further purification. A total of 1.57 g of H-Pro(4-$N_3$)-Dil-OtBu was obtained as a clear oil (3.95 mmol, 88%). LCMS RT=1.19 min (Method B); ESI-MS m/z 398.50 $[M+H]^+$.

To a stirred 23° C. suspension of Dov-OH (1.03 g, 7.12 mmol) and H-Pro(4-$N_3$)-Dil-OtBu (1.57 g, 3.56 mmol) in DMF (10 mL) was added DIEA (1.84 g, 2.50 mL, 0.014 mol), followed by the addition of HATU (2.03 g, 5.33 mmol). After 3 h, analysis by LCMS showed the reaction was complete. The crude reaction was diluted with saturated sodium bicarbonate (10 mL) and extracted with EtOAc (20 mL×2). The combined organic fractions were washed with brine, dried over a pad of magnesium sulfate, filtered, and concentrated in vacuo. The crude oil was purified by preparatory RP-HPLC with a Phenomenex Gemini NX-C18 10μ 110 Å column (150×30 mm) using 5% to 95% MeCN in 0.1% aqueous $NH_4OH$ as the eluent. A total of 817 mg of Dov-Pro(4-$N_3$)-Dil-OtBu was obtained as a white solid (1.56 mmol, 44%). LCMS RT=1.21 min (Method B); ESI-MS m/z 525.28 $[M+H]^+$.

A 23° C. suspension of Dov-Pro(4-$N_3$)-Dil-OtBu (0.817 g, 1.56 mmol) in 3.0 M HCl dioxane was stirred. After 10 h, analysis by LCMS showed the reaction was complete. The volatile organics were evaporated in vacuo to give crude product that was used without further purification. A total of 704 mg of Dov-Pro(4-$N_3$)-Dil-OH was obtained as the HCl salt (1.39 mmol, 89%). LCMS RT=0.676 min (Method B); ESI-MS m/z 469.44 $[M+H]^+$.

To a stirred 23° C. suspension of Dov-Pro(4-$N_3$)-Dil-OH HCl salt (0.120 g, 0.256 mmol) and H-Dap-Phe-OMe TFA salt (0.143 g, 0.310 mmol) in DMF (10 mL) was added DIEA (0.132 g, 0.200 mL, 1.02 mmol), followed by the addition of HATU (0.156 g, 0.410 mmol). After 10 h, analysis by LCMS showed the reaction was complete. The crude reaction was diluted with saturated sodium bicarbonate (10 mL) and extracted with EtOAc (20 mL×3). The combined organic fractions were washed with brine, dried over a pad of magnesium sulfate, filtered, and concentrated in vacuo. The crude oil was purified by preparatory RP-HPLC with a Phenomenex Gemini NX-C18 10μ 110 Å column (150×30 mm) using 5% to 90% MeCN in 0.1% aqueous $NH_4OH$ as the eluent. A total of 37.0 mg of the title compound was obtained as a yellow solid (0.046 mmol, 18%) was obtained as a yellow solid. LCMS RT=1.13 min (Method B); ESI-MS m/z 799.43 $[M+H]^+$; HRMS m/z 799.5064 $[C_{41}H_{66}N_8O_8+H]^+$.

Example 46

(S)-3-((S)-2-(dimethylamino)-3-methylbutanamido)-4-(((3R,4S,5S)-3-methoxy-1-((S)-2-((1R,2R)-1-methoxy-3-(((S)-1-methoxy-1-oxo-3-phenylpropan-2-yl)amino)-2-methyl-3-oxopropyl)pyrrolidin-1-yl)-5-methyl-1-oxoheptan-4-yl)(methyl)amino)-4-oxobutanoic acid

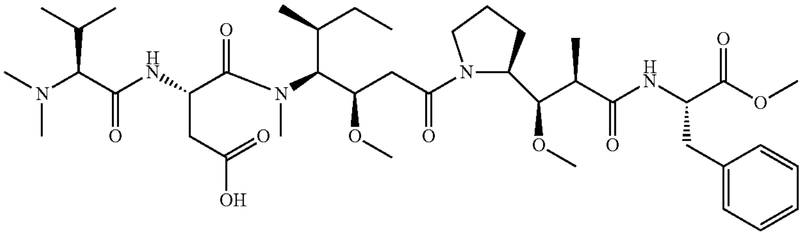 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@H](CC(=O)O)NC(=O)[C@H](C(C)C)N(C)C]

To a stirred 23° C. suspension of Boc-Asp(OBzl)-OH (5.00 g, 15.5 mmol) and H-Dil-OtBu TFA salt (4.36 g, 15.5 mmol) in EtOAc (20 mL) was added DIEA (6.00 g, 8.10 mL, 46.41 mmol). The reaction mixture was cooled to 0° C. and stirred for 0.5 h. After 0.5 h, additional DIEA (6.00 g, 8.01 mL, 46.4 mmol) was added to the reaction mixture and stirred for 0.5 h. Then CMPI (5.93 g, 23.2 mmol) was added to the reaction mixture which was allowed to slowly warm to room temperature and stirred for 10 h. The crude reaction was washed with 1 M HCl (30 mL×2), followed by brine (25 mL×2). The organic fraction was dried over anhydrous magnesium sulfate, filtered, and concentrated in vacuo. The crude product was used without further purification. A total of 7.85 g of Boc-Asp(OBzl)-Dil-OtBu was obtained as a brown oil (13.9 mmol, 90%). LCMS RT=1.72 min (Method B); ESI-MS m/z 565.3 $[M+H]^+$.

A 23° C. solution of Boc-Asp(OBzl)-Dil-OtBu (7.85 g, 13.9 mmol) in 4.0 M HCl in dioxane (20 mL) was stirred. After 10 h, analysis by LCMS showed the reaction was complete. The volatile organics were evaporated in vacuo to give crude product that was used without further purification. A total of 7.85 g of enriched H-Asp(OBzl)-Dil-OH was obtained as the HCl salt. LCMS RT=0.951 min (Method B); ESI-MS m/z 409.40 $[M+H]^+$.

To a stirred 23° C. suspension of Dov-OH (3.00 g, 20.7 mmol) in DMF (20 mL) was added DIEA (6.96 g, 9.40 mL, 0.054 mol) and HATU (7.60 g, 19.9 mmol), followed by the addition of enriched H-Asp(OBzl)-Dil-OH HCl salt (7.85 g). After 4 h, analysis by LCMS showed the reaction was complete. The crude reaction was diluted with saturated sodium bicarbonate (10 mL) and extracted with EtOAc (20 mL×2). The combined organic fractions were washed with brine, dried over a pad of magnesium sulfate, filtered, and concentrated in vacuo. The crude oil was purified by preparatory RP-HPLC with a Phenomenex Gemini NX-C18 10μ 110 Å column (150×30 mm) using 5% to 95% MeCN in 0.1% aqueous $NH_4OH$ as the eluent. A total of 2.00 g of Dov-Asp(OBzl)-Dil-OH was obtained as a white solid (3.74 mmol, 28%). LCMS RT=1.10 min (Method B); ESI-MS m/z 536.5 $[M+H]^+$.

To a stirred 23° C. suspension of Dov-Asp(OBzl)-Dil-OH (1.00 g, 1.87 mmol) and H-Dap-Phe-OMe TFA salt (1.04 g, 2.25 mmol) in DMF (10 mL) was added DIEA (0.970 g, 1.30 mL, 7.47 mmol), followed by the addition of HATU (1.14 g, 2.99 mmol). After 10 h, analysis by LCMS showed the reaction was complete. The crude reaction was diluted with saturated sodium bicarbonate (10 mL) and extracted with EtOAc (20 mL×3). The combined organic fractions were washed with brine, dried over a pad of magnesium sulfate, filtered, and concentrated in vacuo. The crude oil was purified by preparatory RP-HPLC with a Phenomenex Gemini NX-C18 10μ 110 Å column (150×30 mm) using 5% to 90% MeCN in 0.1% aqueous $NH_4OH$ as the eluent. A total of 1.25 g of Dov-Asp(OBzl)-Dil-Dap-Phe-OMe (1.44 mmol, 77%) was obtained as an orange solid. LCMS RT=1.21 min (Method B); ESI-MS m/z 866.6 $[M+H]^+$.

To a stirred 23° C. suspension of Dov-Asp(OBzl)-Dil-Dap-Phe-OMe (0.525 g, 0.606 mmol) in MeOH (10 mL) was added 10% Pd/C (50 mg), followed by the addition of a hydrogen atmosphere. After 5 h, analysis by LCMS showed the reaction was complete. The crude reaction mixture was filtered over a pad of diatomaceous earth, followed by evaporation of the volatile organics. The crude oil was purified by preparatory RP-HPLC with a Phenomenex Gemini NX-C18 10μ 110 Å column (150×30 mm) using 5% to 90% MeCN in 0.1% aqueous $NH_4OH$ as the eluent. A total of 6.00 mg of the title compound was obtained as a white solid (0.008 mmol, 1%). LCMS RT=1.04 min (Method B); ESI-MS m/z 776.43 $[M+H]^+$; HRMS m/z 776.4794 $[C_{40}H_{65}N_5O_{10}+H]^+$.

Example 47

(2S,3R)-2-((S)-2-(dimethylamino)-3-methylbutanamido)-3-hydroxy-N-((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N-methylbutanamide

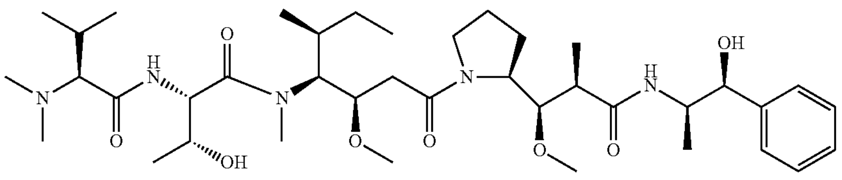 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C)[C@@H](C)O]

To a stirred 23° C. suspension of Dov-Thr(Bzl)-Dil-OH TFA salt (561 mg, 0.883 mmol) and H-Dap-(1R,2S)-(−)-Norephedrine TFA salt (345 mg, 0.794 mmol) in DMF (20 mL) was added DIEA (417 mg, 562μ L, 3.23 mmol) followed by the addition of HATU (820 mg, 2.15 mmol). After 8 h, analysis by LCMS showed the reaction was complete. The crude reaction was diluted with saturated sodium bicarbonate (10 mL) and extracted with EtOAc (20 mL×2). The combined organic fractions were washed with brine, dried over a pad of magnesium sulfate, filtered, and concentrated in vacuo. The crude oil was purified by preparatory RP-HPLC with a Phenomenex Gemini NX-C18 10μ. 110 Å column (150×30 mm) using 5% to 95% MeCN in 0.1% aqueous $NH_4OH$ as the eluent. A total of 326 mg of Dov-Thr(Bzl)-Dil-Dap-(1R,2S)-(−)-Norephedrine was obtained as a white solid (0.396 mmol, 37%). LCMS RT=1.20 min (Method B); ESI-MS m/z 824.76 $[M+H]^+$.

To a stirred 23° C. suspension of Dov-Thr(Bzl)-Dil-Dap-(1R,2S)-(−)-Norephedrine (326 mg, 0.396 mmol) in MeOH (10 mL) was loaded onto a continuous flow hydrogenation reactor using a RaNi (CatCart) and elevated temperature (120° C.) and pressure (80 bar). After elution, analysis by LCMS showed the reaction was complete. The volatile organics were evaporated in vacuo to give crude product, that was purified by preparatory RP-HPLC with a Phenomenex Gemini NX-C18 10μ 110 Å column (150×30 mm) using 5% to 95% MeCN in 0.1% aqueous $NH_4OH$ as the eluent. A total of 15 mg of the title compound was obtained as a white solid (0.020 mmol, 5%). LCMS RT=1.17 min (Method B); ESI-MS m/z 734.5 $[M+H]^+$; HRMS m/z 734.5053 $[C_{39}H_{67}N_5O_8+H]^+$.

Example 48 methyl ((2R,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanoyl)-L-serinate

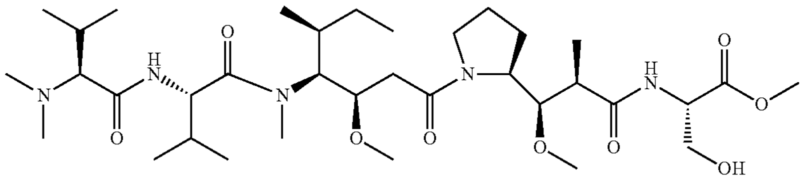

To a stirred 23° C. suspension of Dov-Val-Dil-OH TFA salt (583 mg, 1.07 mmol) and H-Dap-Ser-OMe TFA salt (783 mg, 1.97 mmol) in DMF (10 mL) was added DIEA (223 mg, 0.324 mL, 1.72 mmol), followed by the addition of HATU (1.03 g, 2.71 mmol). After 10 h, analysis by LCMS showed the reaction was complete. The crude reaction was diluted with saturated sodium bicarbonate (10 mL) and extracted with EtOAc (20 mL×3). The combined organic fractions were washed with brine, dried over a pad of magnesium sulfate, filtered, and concentrated in vacuo. The crude oil was purified by preparatory RP-HPLC with a Phenomenex Gemini NX-C18 10μ 110 Å column (150×30 mm) using 5% to 90% MeCN in 0.1% aqueous $NH_4OH$ as the eluent. A total of 704 mg of the title compound was obtained as a pale yellow solid (1.01 mmol, 74%). LCMS RT=0.917 min (Method B); ESI-MS m/z 700.43 $[M+H]^+$; HRMS m/z 700.4843 $[C_{35}H_{65}N_5O_9+H]^+$.

Example 49 methyl ((2R,3R)-3-((S)-1-((3R,4S,5S)-4-((2S,3S)-3-azido-2-((S)-2-(dimethylamino)-3-methylbutanamido)-N-methylbutanamido)-3-methoxy-5-methylheptanoyl)pyrrolidin-2-yl)-3-methoxy-2-methylpropanoyl)-L-isoleucinate

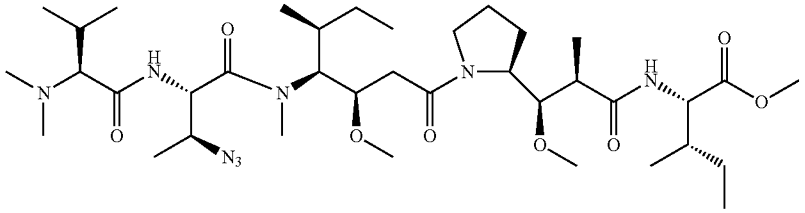

To a stirred 23° C. suspension of Boc-Dap-OH dicyclohexylamine salt (6.62 g, 14.1 mmol) and H-Ile-OMe (3.08 g, 21.2 mmol) in $CH_2Cl_2$ (20 mL) was added DIEA (7.30 g, 9.90 mL, 56.5 mmol), followed by the addition of HATU (3.44 g, 3.20 mL, 0.021 mol). After 10 h, analysis by LCMS showed the reaction was complete. The volatile organics were evaporated in vacuo to give crude product that was used without further purification. A total of 8.56 g of Boc-Dap-Ile-OMe was obtained as a brown oil (20.7 mmol, 88%). LCMS RT=1.51 min (Method B); ESI-MS m/z 415.16 $[M+H]^+$.

To a stirred 23° C. suspension of Boc-Dap-Ile-OMe (6.62 g, 16.0 mmol) in $CH_2Cl_2$ (20 mL) was added TFA (10 mL). After 10 h, analysis by LCMS showed the reaction was complete. The volatile organics were evaporated in vacuo. The crude oil was purified by preparatory RP-HPLC with a Phenomenex Gemini NX-C18 10μ 110 Å column (150×30 mm) using 5% to 95% MeCN in 0.1% aqueous $NH_4OH$ as the eluent. A total of 3.55 g of H-Dap-Ile-OMe was obtained as a yellow solid (8.29 mmol, 52%). LCMS RT=0.691 min (Method B); ESI-MS m/z 315.16 $[M+H]^+$.

To a stirred 23° C. suspension of Dov-Abu(3-$N_3$)-Dil-OH TFA salt (150 mg, 0.329 mmol) and H-Dap-Ile-OMe (207 mg, 0.657 mmol) in DMF (10 mL) was added DIEA (170 mg, 0.220 mL, 1.31 mmol), followed by the addition of HATU (251 mg, 0.657 mmol). After 10 h, analysis by LCMS showed the reaction was complete. The crude reaction was diluted with saturated sodium bicarbonate (10 mL) and extracted with EtOAc (20 mL×3). The combined organic fractions were washed with brine, dried over a pad of magnesium sulfate, filtered, and concentrated in vacuo. The crude oil was purified by preparatory RP-HPLC with a Phenomenex Gemini NX-C18 10 μL 110 Å column (150×30 mm) using 5% to 90% MeCN in 0.1% aqueous $NH_4OH$ as the eluent. A total of 148 mg of the title compound was obtained as a pale yellow solid (0.197 mmol, 60%). LCMS RT=1.43 min (Method B); ESI-MS m/z 753.48 $[M+H]^+$; HRMS m/z 753.5224 $[C_{37}H_{68}N_8O_8+H]^+$.

Example 50

(2S,3S)-3-amino-N-((3R,4S,5S)-1-((S)-2-((1R,2R)-3-(((S)-1-amino-1-oxo-3-phenylpropan-2-yl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N-methylbutanamide

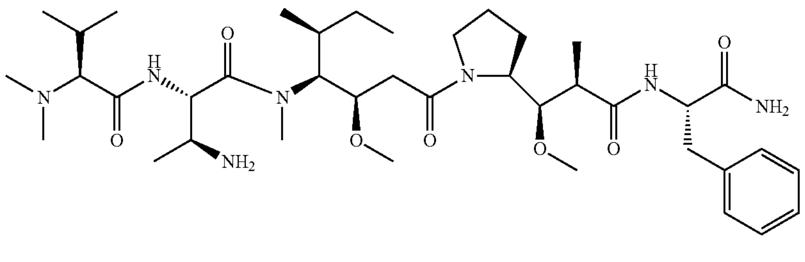 [SMILES: CC[C@H](C)[C@@H]([C@@H](CC(=O)N1CCC[C@H]1[C@H](OC)[C@@H](C)C(=O)N[C@@H](Cc1ccccc1)C(N)=O)OC)N(C)C(=O)[C@@H](NC(=O)[C@H](C(C)C)N(C)C)[C@H](C)N]

To a stirred room temperature solution of Dov-Abu(3-$N_3$)-Dil-Dap-Phe-$NH_2$ (13.4 mg, 0.017 mmol) in THF (0.1 mL) was added trimethylphosphine in THF (1 M, 0.035 mL, 0.035 mmol). After 3 h, additional trimethylphosphine was added (1 M, 0.020 mL, 0.020 mmol). After another 1 h, analysis by LCMS showed that the reaction was complete. The solution was diluted with water and DMF and allowed to stand for 30 min. The crude reaction mixture was purified by preparatory RP-HPLC with a Phenomenex Gemini-NX 10μ C18 110 Å column (150×30 mm) using 5% to 95% MeCN in 0.1% aqueous ammonium hydroxide as the eluent. A total of 5.8 mg of the title compound was obtained (0.008 mmol, 45%). LCMS RT=0.85 min (Method B); ESI-MS m/z 746.6 $[M+H]^+$; HRMS m/z 746.5173 $[C_{39}H_{67}N_7O_7+H]^+$.

Example 51

(2S,3S)-3-amino-N-((3R,4S,5S)-1-((S)-2-((1R,2R)-3-(((S)-1-(tert-butylamino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N-methylbutanamide

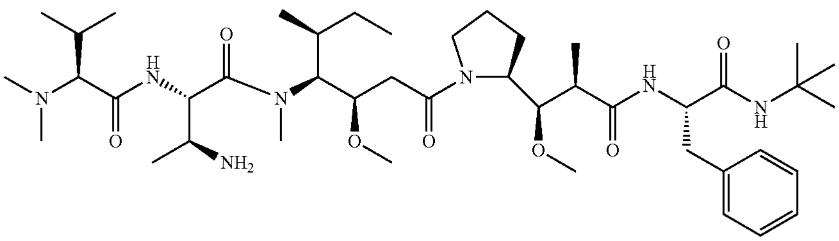 [SMILES: CC[C@H](C)[C@@H]([C@@H](CC(=O)N1CCC[C@H]1[C@H](OC)[C@@H](C)C(=O)N[C@@H](Cc1ccccc1)C(=O)NC(C)(C)C)OC)N(C)C(=O)[C@@H](NC(=O)[C@H](C(C)C)N(C)C)[C@H](C)N]

To a stirred room temperature solution of Dov-Abu(3-$N_3$)-Dil-Dap-Phe-NHt-Bu (15.4 mg, 0.019 mmol) in THF (0.1 mL) was added trimethylphosphine in THF (1 M, 0.037 mL, 0.037 mmol). After 3 h, additional trimethyl phosphine was added (1 M, 0.020 mL, 0.020 mmol) was added. After another 1 h, analysis by LCMS showed that the reaction was complete. The reaction solution was diluted with water and DMF and allowed to stand for 30 min. The crude reaction mixture was purified by preparatory RP-HPLC with a Phenomenex Gemini-NX 10μ C-18 110 Å column (150×30 mm) using 5% to 95% MeCN in 0.1% aqueous ammonium hydroxide as the eluent. A total of 2.7 mg of the title compound was obtained (0.003 mmol, 18%). LCMS RT=0.85 min (Method B); ESI-MS m/z 746.6 $[M+H]^+$; HRMS m/z 802.5799 $[C_{43}H_{75}N_7O_7+H]^+$.

Example 52 methyl ((2R,3R)-3-((S)-1-((3R,4S,5S)-4-((S)-3-azido-N-methyl-2-((S)-3-methyl-2-(methylamino)butanamido)propanamido)-3-methoxy-5-methylheptanoyl)pyrrolidin-2-yl)-3-methoxy-2-methylpropanoyl)-L-phenylalaninate

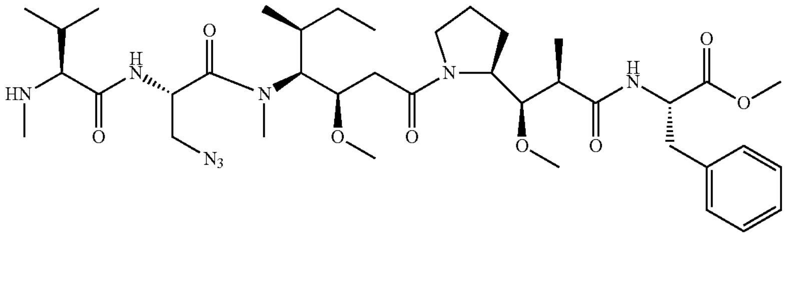 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@H](CN=[N+]=[N-])NC(=O)[C@@H](NC)C(C)C]

To a stirred 23° C. suspension of Fmoc-MeVal-OH (1.03 g, 2.90 mmol) in DMF (10 mL) was added DIEA (1.35 mL, 7.74 mmol), followed by the addition of HATU (1.11 g, 2.90 mmol). After 5 min H-4-Azido-Ala-Dil-OH (0.610 g, 2.90 mmol) was added to the reaction mixture. After 10 h, analysis by LCMS showed that the reaction was complete. The crude reaction was diluted with saturated sodium bicarbonate (15 mL) and extracted with EtOAc (40 mL×2). The combined organic fractions were washed with brine, dried over a pad of magnesium sulfate, filtered, and concentrated in vacuo. The crude oil was purified by preparatory RP-HPLC with a Phenomenex Gemini NX-C18 10μ 110 Å column (150×30 mm) using 5% to 95% MeCN in 0.1% aqueous $NH_4OH$ as the eluent. A total of 348 mg of Fmoc-MeVal-4-Azido-Ala-Dil-OH (0.535 mmol, 28%) was obtained as a yellow oil. LCMS RT=1.80 min (Method B); ESI-MS m/z 651.3 $[M+H]^+$.

To a stirred 23° C. suspension of Fmoc-MeVal-4-Azido-Ala-Dil-OH (348.00 mg, 0.535 mmol) and H-Dap-Phe-OMe (372.66 mg, 1.07 mmol) in DMF (10 mL) was added DIEA (276 mg, 0.400 mL, 2.14 mmol) followed by the addition of HATU (408 mg, 1.07 mmol). After 10 h, analysis by LCMS showed the reaction was complete with deprotection of the Fmoc group occurring concurrently. The crude reaction was diluted with saturated sodium bicarbonate (10 mL) and extracted with EtOAc (20 mL×3). The combined organic fractions were washed with brine, dried over a pad of magnesium sulfate, filtered, and concentrated in vacuo. The crude oil was purified by preparatory RP-HPLC with a Phenomenex Gemini NX-C18 10μ 110 Å column (150×30 mm) using 10% to 90% MeCN in 0.1% aqueous formic acid as the eluent. A total of 5.00 mg of the title compound was obtained (0.006 mmol, 1%). LCMS RT=1.08 min (Method B); ESI-MS m/z 759.5 $[M+H]^+$; HRMS m/z 759.4753 $[C_{38}H_{62}N_8O_8+H]^+$.

Example 53 methyl ((2R,3R)-3-((S)-1-((3R,4S,5S)-4-((2S,3S)-3-azido-N-methyl-2-((S)-3-methyl-2-(methylamino)butanamido)butanamido)-3-methoxy-5-methylheptanoyl)pyrrolidin-2-yl)-3-methoxy-2-methylpropanoyl)-L-phenylalaninate

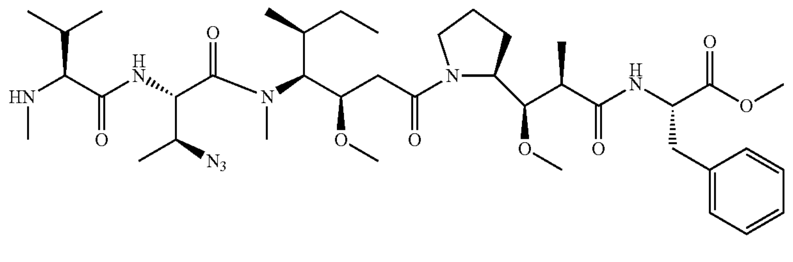 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@@H](NC)C(C)C)[C@H](C)N=[N+]=[N-]]

To a stirred 23° C. suspension of Fmoc-MeVal-OH (2.46 g, 6.96 mmol) and H-Abu(3-$N_3$)-Dil-OtBu (2.46 g, 6.38 mmol) in DMF (10 mL) was added DIEA (3.30 g, 4.5 mL, 25.5 mmol), followed by the addition of HATU (3.65 g, 9.57 mmol). After 6 h, analysis by LCMS showed the reaction was complete. The crude reaction mixture was purified by preparatory RP-HPLC with a Phenomenex Gemini NX-C18 10μ 110 Å column (150×30 mm) using 5% to 95% MeCN in 0.1% aqueous formic acid as the eluent. A total of 3.16 g of Fmoc-MeVal-Abu(3-$N_3$)-Dil-OtBu (4.12 mmol, 65%) was obtained as the formic acid salt. LCMS RT=2.08 min (Method A); ESI-MS m/z 722.7 $[M+H]^+$.

To a stirred 23° C. suspension of Fmoc-MeVal-Abu(3-$N_3$)-Dil-OtBu formic acid salt (3.16 g, 4.12 mmol) in $CH_2CO_2$ (5.0 mL) was added TFA (10.0 mL). After 14 h, analysis by LCMS showed the reaction was complete. The volatile organics were evaporated in vacuo to give an oil. The crude oil was purified by preparatory RP-HPLC with a Phenomenex Gemini NX-C18 10μ 110 Å column (150×30 mm) using 5% to 95% MeCN in 0.1% aqueous TFA as the eluent. A total of 2.26 g of Fmoc-MeVal-Abu(3-$N_3$)-Dil-OH (2.90 mmol, 66%) was obtained as the TFA salt. LCMS RT=1.80 min (Method B); ESI-MS m/z 665.3 $[M+H]^+$.

To a stirred 23° C. suspension of Fmoc-MeVal-Abu(3-$N_3$)-Dil-OH TFA salt (80.0 mg, 0.103 mmol) and H-Dap-Phe-OMe TFA salt (83.9 mg, 0.182 mmol) in DMF (2 mL) was added DIEA (0.083 mL, 0.481 mmol) followed by the addition of HATU (91.8 mg, 0.241 mmol). After 12 h, analysis by LCMS showed the reaction was complete. The crude reaction mixture was diluted with DMF and purified by preparatory RP-HPLC with a Phenomenex Gemini NX-C18 10μ 110 Å column (150×30 mm) using 10% to 90% MeCN in 0.1% aqueous formic acid as the eluent. A total of 97.0 mg of Fmoc-MeVal-Abu(3-$N_3$)-Dil-Dap-Phe-OMe (0.093 mmol, 77%) was obtained as the formic acid salt. LCMS RT=1.90 min (Method B); ESI-MS m/z 995.6 $[M+H]^+$.

To a stirred 23° C. solution of Fmoc-MeVal-Abu(3-$N_3$)-Dil-Dap-Phe-OMe (97.0 mg, 0.093 mmol) in acetonitrile (10 mL) was added piperidine (5 mL). After 5 h, analysis by LCMS showed the reaction was complete. To the crude reaction solution was added hexanes (25 mL×3) in order to extract non-polar by-products. The acetonitrile layer was concentrated in vacuo and the crude oil was purified by preparatory RP-HPLC with a Phenomenex Gemini NX-C18 110 Å column (150×30 mm) using 5% to 95% MeCN in 0.1% aqueous $NH_4OH$ as the eluent. A total of 74.0 mg of the title compound (0.096 mmol, 103%) was obtained as a white solid. LCMS RT=1.09 min (Method B); ESI-MS m/z 773.5 $[M+H]^+$; HRMS m/z 773.4911 $[C_{39}H_{64}N_8O_8+H]^+$.

Example 54

(2S,3S)—N-((3R,4S,5S)-1-((S)-2-((1R,2R)-3-(((S)-1-amino-1-oxo-3-phenylpropan-2-yl)amino)-1-methoxy-2-methyl-3-oxopropyl)pyrrolidin-1-yl)-3-methoxy-5-methyl-1-oxoheptan-4-yl)-3-azido-N-methyl-2-((S)-3-methyl-2-(methylamino)butanamido)butanamide

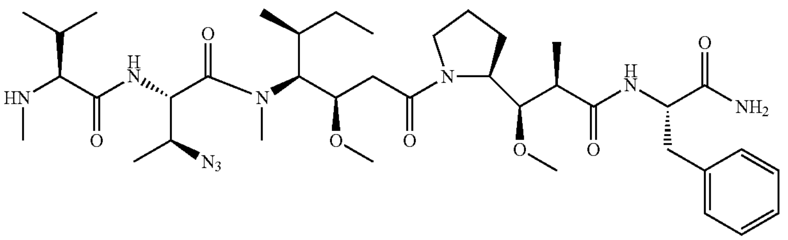 [SMILES: CC[C@H](C)[C@@H]([C@@H](CC(=O)N1CCC[C@H]1[C@H](OC)[C@@H](C)C(=O)N[C@@H](Cc1ccccc1)C(N)=O)OC)N(C)C(=O)[C@@H](NC(=O)[C@@H](NC)C(C)C)[C@H](C)N=[N+]=[N-]]

To a stirred 23° C. suspension of Bod-Dap-OH dicyclohexylamine (10.0 g, 21.3 mmol) and H-Phe-$NH_2$ HCl salt (6.42 g, 32.0 mmol) in $CH_2Cl_2$ (20.0 mL) was added DIEA (11.0 g, 14.9 mL, 85.3 mmol) followed by the addition of DEPC (5.19 g, 4.80 mL, 0.032 mol). After 10 h, analysis by LCMS showed the reaction was complete. The crude reaction was washed with $H_2O$ (25 mL×2), followed by brine (25 mL×2). The organic fraction was dried over a pad of magnesium sulfate, filtered and concentrated in vacuo. The crude orange oil was purified by flash chromatography (silica gel 40 μm, 60 Å, size) using 2% to 10% methanol in $CH_2Cl_2$ as the eluent. A total of 7.25 g of Boc-Dap-Phe-$NH_2$ (16.7 mmol, 78%) was obtained as a yellow oil. LCMS RT=1.28 min (Method B); ESI-MS m/z 434.19 $[M+H]^+$.

To a stirred 23° C. suspension of Boc-Dap-Phe-$NH_2$ (7.25 g, 16.7 mmol) in $CH_2Cl_2$ (10 mL) was added TFA (10 mL). After 5 h, analysis by LCMS showed the reaction was complete. The volatile organics were evaporated in vacuo to give crude product, which was used without further purification. A total of 6.00 g of H-Dap-Phe-$NH_2$ was obtained as an orange solid (13.4 mmol, 80%). LCMS RT=0.691 min (Method B); ESI-MS m/z 334.17 $[M+H]^+$.

To a stirred 23° C. suspension of Fmoc-MeVal-Abu(3-$N_3$)-Dil-OH TFA salt (456 mg, 0.586 mmol) and H-Dap-Phe-$NH_2$ TFA salt (457 mg, 1.02 mmol) in DMF (10 mL) was added DIEA (0.350 g, 0.500 mL, 2.74 mmol) followed by the addition of HATU (0.520 g, 1.37 mmol). After 10 h, analysis by LCMS showed the reaction was complete. The crude reaction was purified by preparatory RP-HPLC with a Phenomenex Gemini NX-C18 10μ 110 Å column (150×30 mm) using 10% to 90% MeCN in 0.1% aqueous formic acid as the eluent. A total of 526 mg of Fmoc-MeVal-Abu(3-$N_3$)-Dil-Dap-Phe-$NH_2$ was obtained as the formic acid salt (0.513 mmol, 75%). LCMS RT=1.81 min (Method B); ESI-MS m/z 980.39 $[M+H]^+$.

To a stirred 23° C. solution of Fmoc-MeVal-Abu(3-$N_3$)-Dil-Dap-Phe-$NH_2$ (525 mg, 0.513 mmol) in acetonitrile (10 mL) was added piperidine (5 mL). After 2 h, analysis by LCMS showed the reaction was complete. To the crude reaction solution was added hexanes (15 mL×3). The acetonitrile layer was concentrated in vacuo. The crude oil was purified by preparatory RP-HPLC with a Phenomenex Gemini NX-C18 10μ 110 Å column (150×30 mm) using 5% to 95% MeCN in 0.1% aqueous TFA as the eluent. A total of 354 mg of the title compound was obtained as the TFA salt (0.406 mmol, 79%). LCMS RT=1.15 min (Method B); ESI-MS m/z 758.24 $[M+H]^+$; HRMS m/z 758.4915 $[C_{38}H_{63}N_9O_7+H]^+$.

Example 55

((2S,3S)-3-azido-N-((3R,4S,5S)-1-((S)-2-((1R,2R)-3-(((S)-1-(tert-butylamino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)-N-methyl-2-((S)-3-methyl-2-(methylamino)butanamido)butanamide

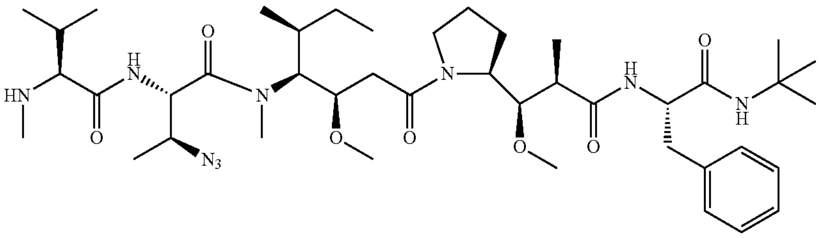 [SMILES: CC[C@H](C)[C@@H]([C@@H](CC(=O)N1CCC[C@H]1[C@H](OC)[C@@H](C)C(=O)N[C@@H](Cc1ccccc1)C(=O)NC(C)(C)C)OC)N(C)C(=O)[C@@H](NC(=O)[C@@H](NC)C(C)C)[C@H](C)N=[N+]=[N-]]

To a stirred room temperature solution of Fmoc-MeVal-Abu(3-$N_3$)-Dil-Dap-Phe-OH (111 mg, 0.113 mmol), tert-butyl amine hydrochloride (31.5 mg, 0.287 mmol), HATU (92.0 mg, 0.242 mmol) in DMF (1.0 mL) was added Hunig's base (0.079 mL, 0.454 mmol). After 1 h, analysis by LCMS showed the reaction was complete. The crude reaction mixture was diluted with ethyl acetate and the organic fraction were washed with 1 N HCl and brine. The organic fraction was dried over magnesium sulfate, filtered and concentrated under reduced pressure. The crude yellow oil was dissolved in piperidine (2.0 mL) and acetonitrile (5.0 mL). After 1 h, analysis by LCMS showed the reaction was complete. The acetonitrile layer was extracted with hexanes (2×) and the acetonitrile layer was concentrated under reduced pressure. The crude oil was purified by preparatory RP-HPLC with a Phenomenex Gemini-NX 10μ C-18 110 Å column (150×30 mm) using 5% to 95% MeCN in 0.1% aqueous ammonium hydroxide as the eluent. A total of 50.3 mg of the title compound was obtained (0.062 mmol, 55%). LCMS RT=1.29 min (Method B); ESI-MS m/z 814.1 $[M+H]^+$; HRMS m/z 814.5541 $[C_{42}H_{71}N_9O_7+H]^+$.

Example 56 tert-butyl ((2R,3R)-3-((S)-1-((3R,4S,5S)-4-((2S,3S)-3-azido-N-methyl-2-((S)-3-methyl-2-(methylamino)butanamido)butanamido)-3-methoxy-5-methylheptanoyl)pyrrolidin-2-yl)-3-methoxy-2-methylpropanoyl)-L-phenylalaninate

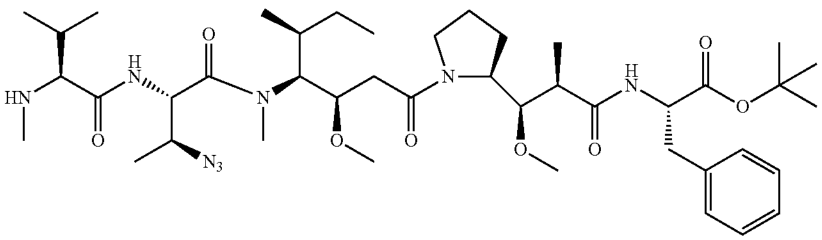 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC(C)(C)C)OC)N(C)C(=O)[C@@H](NC(=O)[C@@H](NC)C(C)C)[C@H](C)N=[N+]=[N-]]

To a stirred 25° C. solution of Boc-Dap-OH dicyclohexylamine salt (6.47 g, 13.8 mmol) and H-Phe-OtBu (3.91 g, 15.2 mmol) in DCM (20 mL) was added DIEA (8.76 mL, 55.2 mmol), followed by the addition of DEPC (3.12 mL, 20.7). After 8 h, analysis by LCMS showed the reaction was complete. The volatile organics were evaporated in vacuo to give crude product that was used without further purification. A total of 5.35 g of Boc-Dap-Phe-OtBu was obtained (10.9 mmol, 79%). LCMS RT=2.89 min (Method A); ESI-MS m/z 491.48 $[M+H]^+$.

To a stirred room temperature solution of Boc-Dap-Phe-OtBu (5.25 g, 10.7 mmol) in $CH_2Cl_2$ (10.0 mL) was added TFA (10.0 mL). After 12 h, analysis by LCMS showed the reaction was complete. The crude oil was purified by preparatory RP-HPLC with a Phenomenex Synergi 10μ Max-RP 80 Å column (150×30 mm) using 10% to 90% MeCN in 0.05% aqueous TFA as the eluent. A total of 2.85 g of H-Dap-Phe-OtBu was obtained as the TFA salt (5.65 mmol, 68%). LCMS RT=1.82 min (Method A); ESI-MS m/z 391.02 $[M+H]^+$.

To a stirred 23° C. suspension of Fmoc-MeVal-Abu(3-$N_3$)-Dil-OH TFA salt (410 mg, 0.527 mmol) and H-Dap-Phe-OtBu TFA salt (482 mg, 0.956 mmol) in DMF (10 mL) was added DIEA (319 mg, 430 μL, 2.47 mmol) followed by the addition of HATU (470 mg, 1.23 mmol). After 10 h, analysis by LCMS showed the reaction was complete along with 10% of the Fmoc group being removed. The crude reaction mixture was purified by preparatory RP-HPLC with a Phenomenex Gemini NX-C18 10μ 110 Å column (150×30 mm) using 10% to 90% MeCN in 0.1% aqueous formic acid as the eluent. A total of 26.0 mg of the title compound was obtained as a white formic acid salt (0.030 mmol, 5%). LCMS RT=1.41 min (Method B); ESI-MS m/z 815.33 $[M+H]^+$; HRMS m/z 815.5383 $[C_{42}H_{70}N_8O_8+H]^+$.

Example 57

((2R,3R)-3-((S)-1-((3R,4S,5S)-4-((2S,3S)-3-azido-N-methyl-2-((S)-3-methyl-2-(methylamino)butanamido)butanamido)-3-methoxy-5-methylheptanoyl)pyrrolidin-2-yl)-3-methoxy-2-methylpropanoyl)-L-phenylalanine

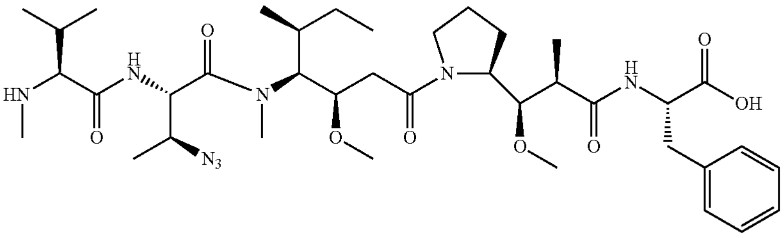 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@@H](NC)C(C)C)[C@H](C)N=[N+]=[N-]]

To a stirred 23° C. suspension of Fmoc-MeVal-Abu(3-$N_3$)-Dil-OH TFA salt (410 mg, 0.527 mmol) and H-Dap-Phe-OtBu TFA salt (482 mg, 0.956 mmol) in DMF (10 mL) was added DIEA (319 mg, 430 μL, 2.47 mmol) followed by the addition of HATU (470 mg, 1.23 mmol). After 10 h, analysis by LCMS showed the reaction was complete. The crude reaction mixture was purified by preparatory RP-HPLC with a Phenomenex Gemini NX-C18 10μ 110 Å column (150×30 mm) using 10% to 90% MeCN in 0.1% aqueous formic acid as the eluent. A total of 648 mg of Fmoc-MeVal-Abu(3-$N_3$)-Dil-Dap-Phe-OtBu was obtained as a white formic acid salt (0.598 mmol, 97%). LCMS RT=1.41 min (Method B); ESI-MS m/z 1037.41 $[M+H]^+$.

To a stirred 23° C. suspension of Fmoc-MeVal-Abu(3-$N_3$)-Dil-Dap-Phe-OtBu formic acid salt (648 mg, 0.598 mmol) in $CH_2Cl_2$ (5.00 mL) was added TFA (5.00 mL). After 2 h, analysis by LCMS showed the reaction was complete. The volatile organics were evaporated in vacuo to give a brown oil. The crude oil was purified by preparatory RP-HPLC with a Phenomenex Gemini NX-C18 10μ 110 Å column (150×30 mm) using 5% to 95% MeCN in 0.1% aqueous TFA as the eluent. A total of 502 mg of Fmoc-MeVal-Abu(3-$N_3$)-Dil-Dap-Phe-OH was obtained as the TFA salt (0.458 mmol, 77%). LCMS RT=1.81 min (Method B); ESI-MS m/z 981.22 $[M+H]^+$.

To a stirred 23° C. solution of Fmoc-MeVal-Abu(3-$N_3$)-Dil-Dap-Phe-OH TFA salt (392 mg, 0.382 mmol) in acetonitrile (10 mL) was added piperidine (5 mL). After 2 h, analysis by LCMS showed the reaction was complete. To the crude reaction solution was added hexanes (15 mL×3). The acetonitrile layer was concentrated in vacuo. The crude oil was purified by preparatory RP-HPLC with a Phenomenex Gemini NX-C18 10μ 110 Å column (150×30 mm) using 5% to 95% MeCN in 0.1% aqueous TFA as the eluent. A total of 360 mg of the enriched title compound was obtained as the TFA salt. LCMS RT=1.19 min (Method B); ESI-MS m/z 759.13 $[M+H]^+$; HRMS m/z 759.4755 $[C_{38}H_{62}N_8O_8+H]^+$.

Example 58 tert-butyl ((2R,3R)-3-((S)-1-((3R,4S,5S)-4-((2S,3S)-3-azido-2-((S)-2-(dimethylamino)-3-methylbutanamido)-N-methylbutanamido)-3-methoxy-5-methylheptanoyl)pyrrolidin-2-yl)-3-methoxy-2-methylpropanoyl)-L-phenylalaninate

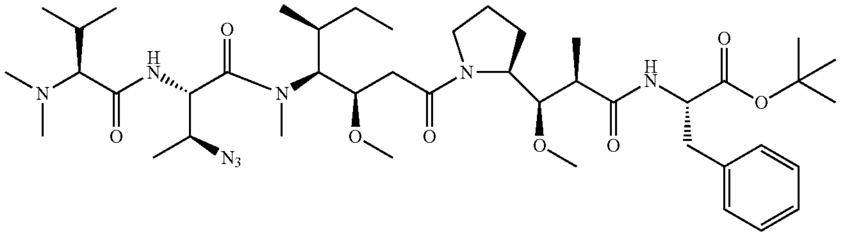 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC(C)(C)C)OC)N(C)C(=O)[C@@H](NC(=O)[C@H](C(C)C)N(C)C)[C@H](C)N=[N+]=[N-]]

To a stirred 23° C. suspension of Dov-Abu(3-$N_3$)-Dil-OH TFA salt (327 mg, 0.574 mmol) and H-Dap-Phe-OtBu TFA salt (0.340 g, 0.675 mmol) in DMF (10 mL) was added DIEA (0.370 g, 0.500 mL, 2.87 mmol) followed by the addition of HATU (0.550 g, 1.43 mmol). After 10 h, analysis by LCMS showed the reaction was complete. The crude reaction was purified by preparatory RP-HPLC with a Phenomenex Gemini NX-C18 10 μl 110 Å column (150×30 mm) using 10% to 90% MeCN in 0.1% aqueous formic acid as the eluent. A total of 453 mg (0.518 mmol, 72%) of the title compound was obtained as the formic acid salt. LCMS RT=1.42 min (Method B); ESI-MS m/z 828.94 $[M+H]^+$; HRMS m/z 829.5536 $[C_{43}H_{72}N_8O_8+H]^+$.

Example 59

(2S,3S)-3-azido-2-((S)-2-(dimethylamino)-3-methylbutanamido)-N-((3R,4S,5S)-3-methoxy-1-((S)-2-((1R,2R)-1-methoxy-2-methyl-3-oxo-3-(((S)-2-phenyl-1-(1H-tetrazol-5-yl)ethyl)amino)propyl)pyrrolidin-1-yl)-5-methyl-1-oxoheptan-4-yl)-N-methylbutanamide

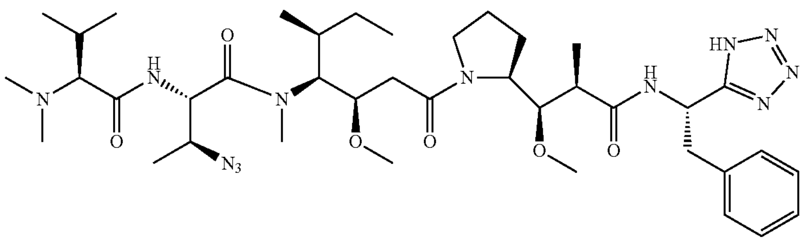 [SMILES: CC[C@H](C)[C@@H]([C@@H](CC(=O)N1CCC[C@H]1[C@H](OC)[C@@H](C)C(=O)N[C@@H](Cc1ccccc1)c1nnn[nH]1)OC)N(C)C(=O)[C@@H](NC(=O)[C@H](C(C)C)N(C)C)[C@H](C)N=[N+]=[N-]]

To a stirred 23° C. suspension of Boc-Dap-OH dicyclohexylamine salt (2.48 g, 5.29 mmol) and (S)-2-Phenyl-1-(1H-tetrazol-5-yl)ethanamine (1.00 g, 5.29 mmol) in $CH_2Cl_2$ (20.0 mL) was added DIEA (2.73 g, 3.7 mL, 21.1 mmol) followed by the addition of DEPC (1.29 g, 1.20 mL, 7.93 mmol). After 10 h, analysis by LCMS showed the reaction was complete. The volatile organics were evaporated in vacuo. The crude oil was purified by preparatory RP-HPLC with a Phenomenex Gemini NX-C18 10μ 110 Å column (150x30 mm) using 5% to 95% MeCN in 0.1% aqueous formic acid as the eluent. A total of 2.52 g of Boc-Dap-(S)-2-Phenyl-1-(1H-tetrazol-5-yl)ethanamine (4.99 mmol, 94%) was obtained as the formic acid salt. LCMS RT=1.35 min (Method B); ESI-MS m/z 459.2 $[M+H]^+$.

To a stirred 23° C. suspension of Boc-Dap-(S)-2-Phenyl-1-(1H-tetrazol-5-yl)ethanamine (2.52 g, 4.99 mmol) in $CH_2Cl_2$ (10.0 mL) was added TFA (5.00 mL). After 5 h, analysis by LCMS showed the reaction was complete. The volatile organics were evaporated in vacuo to give crude product that was used without further purification. A total of 2.43 g of H-Dap-(S)-2-Phenyl-1-(1H-tetrazol-5-yl)ethanamine (5.14 mmol, 84%) was obtained as the TFA salt. LCMS RT=0.575 min (Method B); ESI-MS m/z 359.2 $[M+H]^+$.

To a stirred 23° C. suspension of Dov-Abu(3-$N_3$)-Dil-OH TFA salt (305 mg, 0.668 mmol) and H-Dap-(S)-2-Phenyl-1-(1H-tetrazol-5-yl)ethanamine TFA salt (0.36 g, 1.002 mmol) in DMF (10 mL) was added DIEA (0.35 g, 0.5 mL, 2.67 mmol) followed by the addition of HATU (509 mg, 1.34 mmol). After 10 h, analysis by LCMS showed the reaction was complete. The crude reaction was diluted with saturated sodium bicarbonate (10 mL) and extracted with EtOAc (20 mLx3). The combined organic fractions were washed with brine, dried over a pad of magnesium sulfate, filtered, and concentrated in vacuo. The crude oil was purified by preparatory RP-HPLC with a Phenomenex Gemini NX-C18 10μ 110 Å column (150x30 mm) using 10% to 90% MeCN in 0.1% aqueous formic acid as the eluent. A total of 47.0 mg of the title compound was obtained as the formic acid salt (0.056 mmol, 8%). LCMS RT=1.24 min (Method B); ESI-MS m/z 797.3 $[M+H]^+$; HRMS m/z 797.5139 $[C_{39}H_{64}N_{12}O_6+H]^+$.

Example 60

(2S,3S)-3-azido-N-((3R,4S,5S)-3-methoxy-1-((S)-2-((1R,2R)-1-methoxy-2-methyl-3-oxo-3-(((S)-2-phenyl-1-(1H-tetrazol-5-yl)ethyl)amino)propyl)pyrrolidin-1-yl)-5-methyl-1-oxoheptan-4-yl)-N-methyl-2-((S)-3-methyl-2-(methylamino)butanamido) butanamide

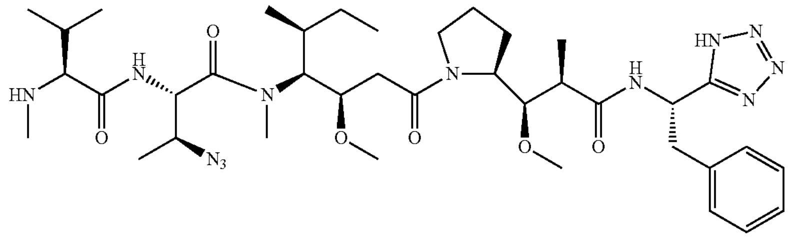 [SMILES: CC[C@H](C)[C@@H]([C@@H](CC(=O)N1CCC[C@H]1[C@H](OC)[C@@H](C)C(=O)N[C@@H](Cc1ccccc1)c1nnn[nH]1)OC)N(C)C(=O)[C@@H](NC(=O)[C@@H](NC)C(C)C)[C@H](C)N=[N+]=[N-]]

To a stirred 23° C. suspension of Fmoc-MeVal-Abu(3-$N_3$)-Dil-OH TFA salt (0.491 g, 0.631 mmol) and H-Dap-(S)-2-Phenyl-1-(1H-tetrazol-5-yl)ethanamine TFA salt (0.532 g, 1.13 mmol) in DMF (10 mL) was added DIEA (0.381 g, 0.500 mL, 2.97 mmol) followed by the addition of HATU (0.57 g, 1.486 mmol). After 10 h, analysis by LCMS showed the reaction was complete. The crude reaction was diluted with saturated sodium bicarbonate (10 mL) and extracted with EtOAc (20 mL×3). The combined organic fractions were washed with brine, dried over a pad of magnesium sulfate, filtered, and concentrated in vacuo. The crude oil was purified by preparatory RP-HPLC with a Phenomenex Gemini NX-C18 10μ 110 Å column (150×30 mm) using 10% to 90% MeCN in 0.1% aqueous formic acid as the eluent. A total of 125 mg of Fmoc-MeVal-Abu(3-$N_3$)-Dil-Dap-(S)-2-Phenyl-1-(1H-tetrazol-5-yl)ethanamine was obtained as the formic acid salt (0.119 mmol, 16%). LCMS RT=1.94 min (Method B); ESI-MS m/z 1005.35 $[M+H]^+$.

To a stirred 23° C. solution of Fmoc-MeVal-Abu(3-$N_3$)-Dil-Dap-(S)-2-Phenyl-1-(1H-tetrazol-5-yl)ethanamine (525 mg, 0.499 mmol) in acetonitrile (10 mL) was added piperidine (5 mL). After 2 h, analysis by LCMS showed the reaction was complete. To the crude reaction solution was added hexanes (×3). The acetonitrile layer was concentrated in vacuo. The crude oil was purified by preparatory RP-HPLC with a Phenomenex Gemini NX-C18 10μ 110 Å column (150×30 mm) using 5% to 95% MeCN in 0.1% aqueous TFA as the eluent. A total of 20.0 mg of the title compound was obtained as the TFA salt (0.022 mmol, 5%). LCMS RT=1.37 min (Method B); ESI-MS m/z 783.42 $[M+H]^+$; HRMS m/z 783.4979 $[C_{38}H_{62}N_{12}O_6+H]^+$.

Example 61

(2S,3S)-3-azido-2-((S)-2-(dimethylamino)-3-methylbutanamido)-N-((3R,4S,5S)-3-methoxy-1-((S)-2-((1R,2R)-1-methoxy-2-methyl-3-oxo-3-(((S)-2-phenyl-1-(thiazol-2-yl)ethyl)amino)propyl)pyrrolidin-1-yl)-5-methyl-1-oxoheptan-4-yl)-N-methylbutanamide

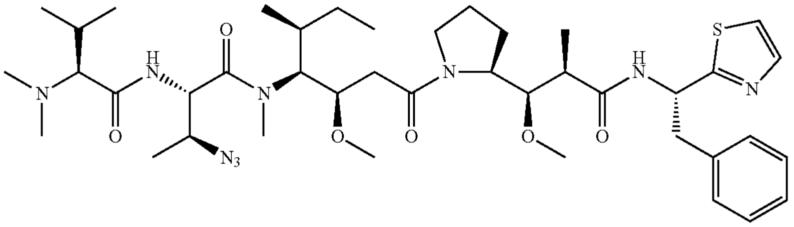 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)C)[C@H](C)N=[N+]=[N-]]

To a stirred 23° C. suspension of Boc-Dap-OH dicyclohexylamine salt (1.95 g, 4.154 mmol) and (S)-2-phenyl-1-(2-thiazol-2-yl)ethylamine (1.00 g, 4.154 mmol) in $CH_2Cl_2$ (20.0 mL) was added DIEA (2.15 g, 2.9 mL, 16.615 mmol) followed by the addition of DEPC (1.01 g, 0.9 mL, 0.006 mol). After 10 h, analysis by LCMS showed the reaction was complete. The crude reaction mixture was washed with $H_2O$ (25 mL×2), followed by brine (25 mL×2). The organic fraction was dried over a pad of $MgSO_4$, filtered and concentrated in vacuo. A total of 1.65 g of Boc-Dap-(S)-2-phenyl-1-(thiazol-2-yl)ethanamine (3.48 mmol, 84%) was obtained as a yellow oil. LCMS RT=1.59 min (Method B); ESI-MS m/z 475.2[M+H]$^+$.

To a stirred 23° C. suspension of Boc-Dap-(S)-2-phenyl-1-(thiazol-2-yl)ethanamine (1.65 g, 3.49 mmol) in $CH_2Cl_2$ (10.0 mL) was added TFA (10.0 mL). After 4 h, analysis by LCMS showed the reaction was complete. The volatile organics were evaporated in vacuo. The crude oil was dissolved in DMF (5 mL) and triethylamine (1 mL) to achieve a pH of 8. The crude oil was purified by preparatory RP-HPLC with a Phenomenex Gemini NX-C18 10μ 110 Å column (150×30 mm) using 5% to 95% MeCN in 0.1% aqueous TFA as the eluent. A total of 935 mg of H-Dap-(S)-2-phenyl-1-(thiazol-2-yl)ethanamine (1.92 mmol, 55%) was obtained as the TFA salt. LCMS RT=1.04 min (Method B); ESI-MS m/z 375.0 [M+H]$^+$.

To a stirred 23° C. suspension of Dov-Abu(3-$N_3$)-Dil-OH TFA salt (302 mg, 0.661 mmol) and H-Dap-(S)-2-phenyl-1-(thiazol-2-yl)ethanamine TFA salt (247 mg, 0.661 mmol) in DMF (10 mL) was added DIEA (0.34 g, 0.5 mL, 2.65 mmol) followed by HATU (504 mg, 1.32 mmol). After 10 h, analysis by LCMS showed the reaction was complete. The crude reaction mixture was diluted with saturated sodium bicarbonate (10 mL) and extracted with EtOAc (20 mL×3). The combined organic fractions were washed with brine, dried over a pad of magnesium sulfate, filtered, and concentrated in vacuo. The crude oil was purified by preparatory RP-HPLC with a Phenomenex Gemini NX-C18 10μ 110 Å column (150×30 mm) using 10% to 90% MeCN in 0.1% aqueous TFA as the eluent. A total of 111 mg of the title compound was obtained as the TFA salt (0.120 mmol, 18%). LCMS RT=1.33 min (Method B); ESI-MS m/z 812.2 [M+H]$^+$; HRMS m/z 812.4835 [$C_{41}H_{65}N_9O_6S$+H]$^+$.

Example 62 tert-butyl ((2R,3R)-3-((S)-1-((3R,4S,5S)-4-((2S,3S)-3-amino-2-((S)-2-(dimethylamino)-3-methylbutanamido)-N-methylbutanamido)-3-methoxy-5-methylheptanoyl)pyrrolidin-2-yl)-3-methoxy-2-methylpropanoyl)-L-phenylalaninate

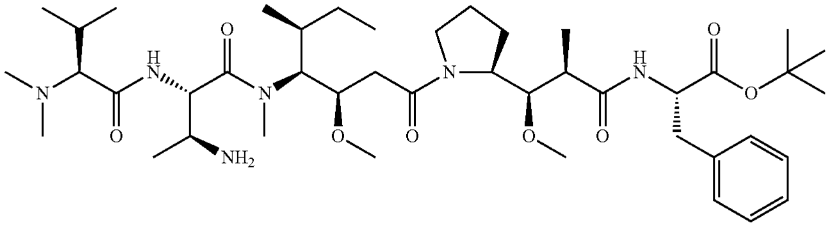 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC(C)(C)C)OC)N(C)C(=O)[C@@H](NC(=O)[C@H](C(C)C)N(C)C)[C@H](C)N]

To a stirred room temperature solution of Dov-Abu(3-$N_3$)-Dil-Dap-Phe-Ot-Bu formic acid salt (102.5 mg, 0.117 mmol) in DMF (1.0 mL) was added trimethylphosphine in THF (1 M, 0.350 mL, 0.350 mmol). After 2 h, analysis by LCMS showed that the reaction was complete. The crude reaction mixture was purified by preparatory RP-HPLC with a Phenomenex Gemini-NX 10μ C-18 110 Å column (150×30 mm) using 5% to 95% MeCN in 0.1% aqueous formic acid as the eluent. A total of 70.1 mg of the title compound was obtained as a formic acid salt (0.083 mmol, 70%). LCMS RT=1.22 min (Method B); ESI-MS m/z 803.3 $[M+H]^+$; HRMS m/z 803.5642 $[C_{43}H_{74}N_6O_8+H]^+$.

Example 63

(2S,3S)-3-amino-2-((S)-2-(dimethylamino)-3-methylbutanamido)-N-((3R,4S,5S)-3-methoxy-1-((S)-2-((1R,2R)-1-methoxy-2-methyl-3-oxo-3-(((S)-2-phenyl-1-(1H-tetrazol-5-yl)ethyl)amino)propyl)pyrrolidin-1-yl)-5-methyl-1-oxoheptan-4-yl)-N-methylbutanamide

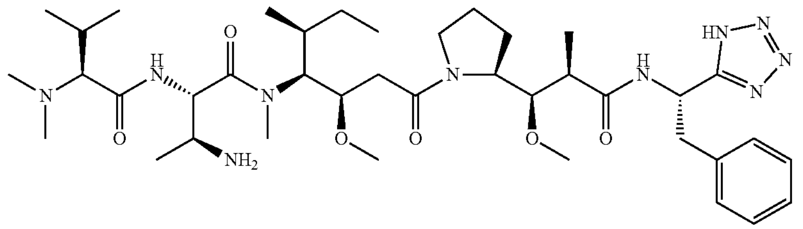 [SMILES: CC[C@H](C)[C@@H]([C@@H](CC(=O)N1CCC[C@H]1[C@H](OC)[C@@H](C)C(=O)N[C@@H](Cc1ccccc1)c1nnn[nH]1)OC)N(C)C(=O)[C@@H](NC(=O)[C@H](C(C)C)N(C)C)[C@H](C)N]

To a stirred room temperature solution of Dov-Abu(3-$N_3$)-Dil-Dap-Phe-Tetrazole formic acid salt (19.4 mg, 0.023 mmol) in DMF (0.2 mL) was added trimethylphosphine in THF (1 M, 0.068 mL, 0.068 mmol). After 2 h, analysis by LCMS showed that the reaction was complete. The crude reaction mixture was purified by preparatory RP-HPLC with a Phenomenex Gemini-NX 10μ C-18 110 Å column (150×30 mm) using 5% to 95% MeCN in 0.1% aqueous formic acid as the eluent. A total of 9.9 mg of the title compound was obtained as a formic acid salt (0.012 mmol, 53%). LCMS RT=1.07 min (Method B); ESI-MS m/z 771.2 $[M+H]^+$; HRMS m/z 771.5233 $[C_{39}H_{66}N_{10}O_8+H]^+$.

Example 64

(2S,3S)-3-amino-2-((S)-2-(dimethylamino)-3-methylbutanamido)-N-((3R,4S,5S)-3-methoxy-1-((S)-2-((1R,2R)-1-methoxy-2-methyl-3-oxo-3-(((S)-2-phenyl-1-(thiazol-2-yl)ethyl)amino)propyl)pyrrolidin-1-yl)-5-methyl-1-oxoheptan-4-yl)-N-methylbutanamide

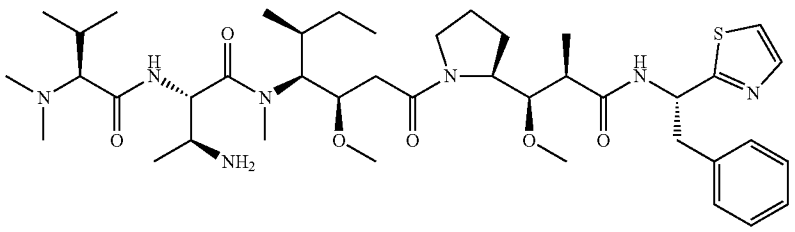 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)C)[C@H](C)N]

To a stirred room temperature solution of Dov-Abu(3-$N_3$)-Dil-Dap-Phe-Thiazole formic acid salt (37.2 mg, 0.043 mmol) in THF (0.2 mL) was added trimethylphosphine in THF (1 M, 0.090 mL, 0.090 mmol). After 1 h, analysis by LCMS showed that the reaction was complete. The crude reaction mixture was purified by preparatory RP-HPLC with a Phenomenex Gemini-NX 10μ C-18 110 Å column (150×30 mm) using 5% to 95% MeCN in 0.1% aqueous formic acid as the eluent. A total of 16.8 mg of the title compound was obtained as a formic acid salt (0.020 mmol, 47%). LCMS RT=1.15 min (Method B); ESI-MS m/z 786.2 $[M+H]^+$; HRMS m/z 786.4940 $[C_{41}H_{67}N_7O_6S+H]^+$.

Example B1

In Vitro Cytotoxicity Experiments

Figure 9:
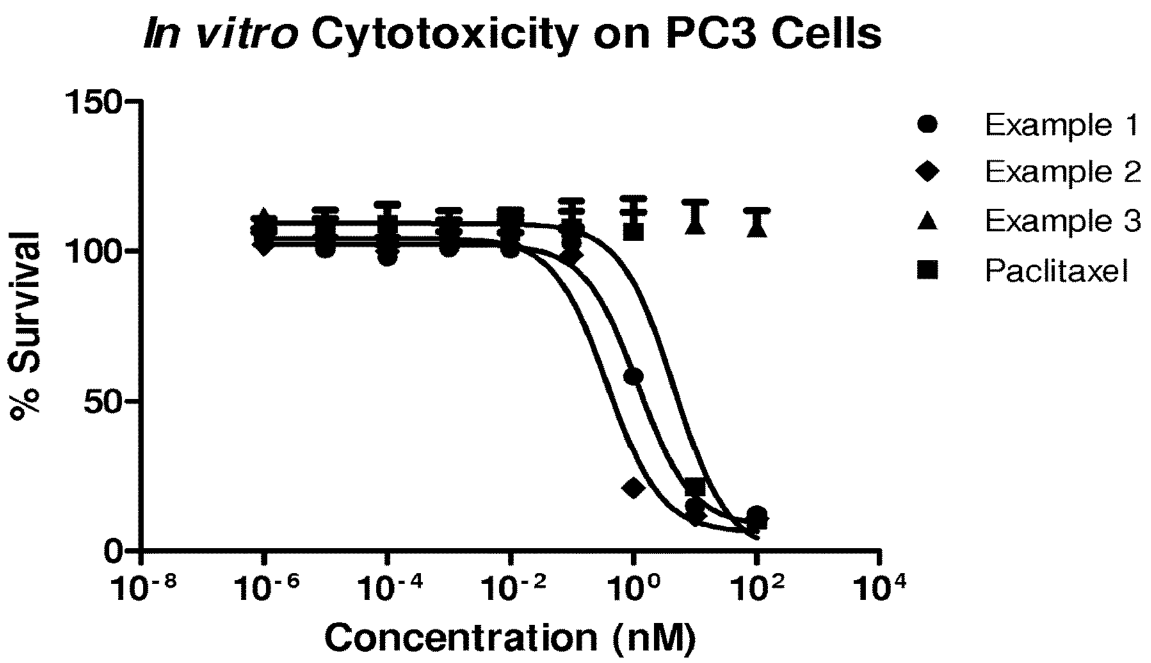
FIG. 9 shows the results for Examples 1, 2, 3 and Paclitaxel in an in vitro cytotoxicity experiment using PC3 cells, as described in Example B1. Data is graphed as percent survival versus concentration of test compound, compared to untreated control wells.
Figure 10:
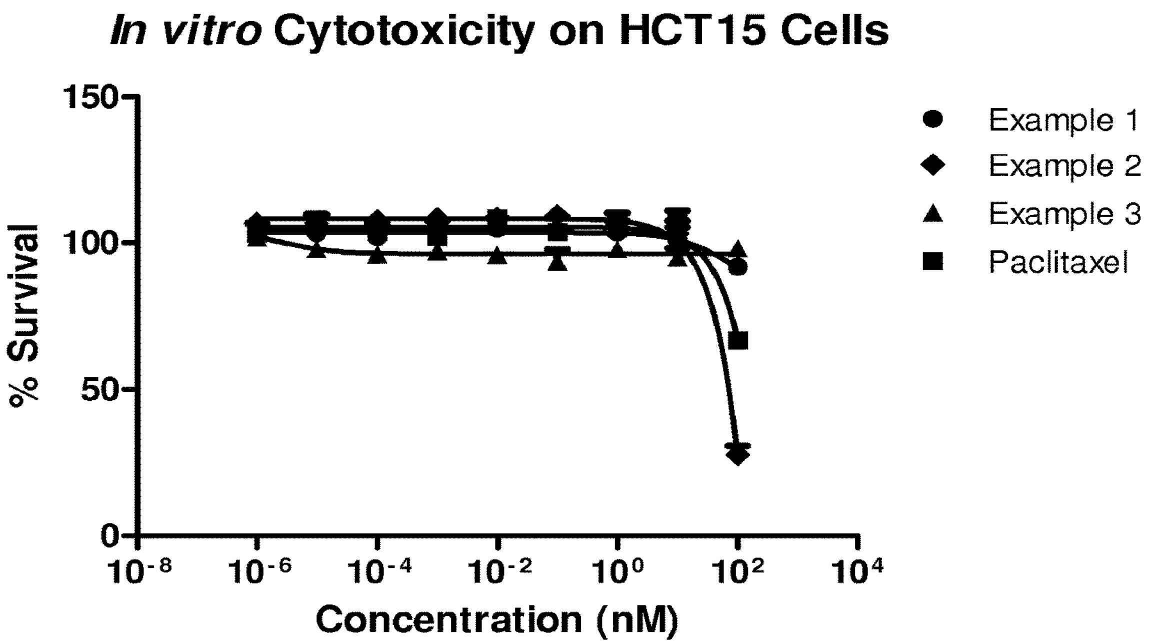
FIG. 10 shows the results for Examples 1, 2, 3 and Paclitaxel in an in vitro cytotoxicity experiment using HCT15 cells, as described in Example B1. Data is graphed as percent survival versus concentration of test compound, compared to untreated control wells.
Figure 11:
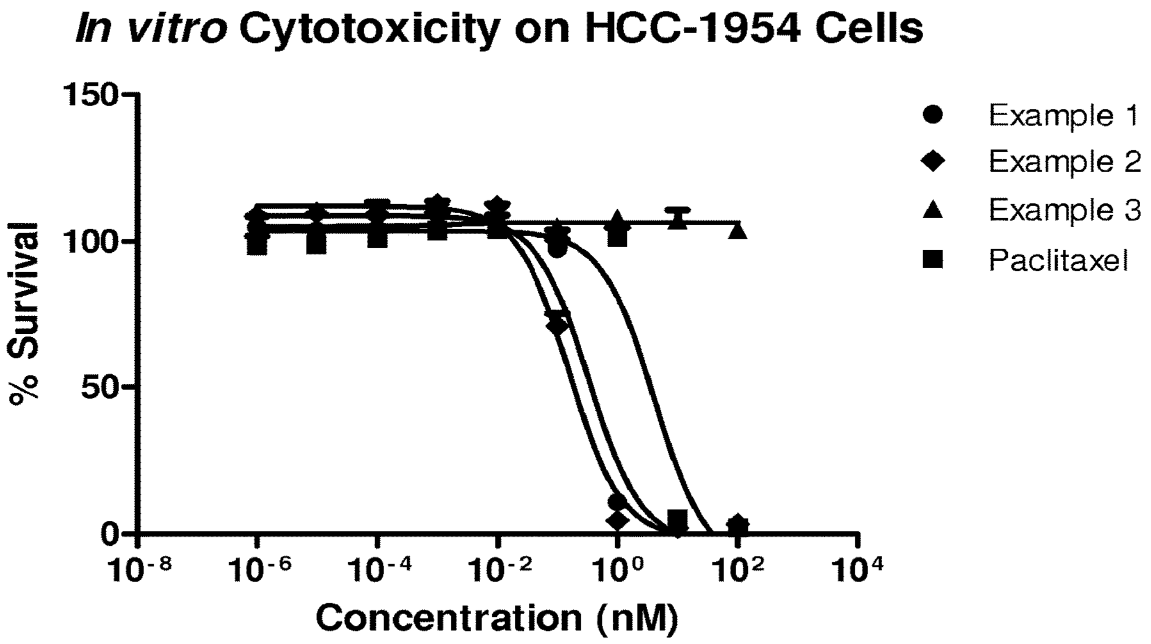
FIG. 11 shows the results for Examples 1, 2, 3 and Paclitaxel in an in vitro cytotoxicity experiment using HCC-1954 cells, as described in Example B1. Data is graphed as percent survival versus concentration of test compound, compared to untreated control wells.
Figure 12:
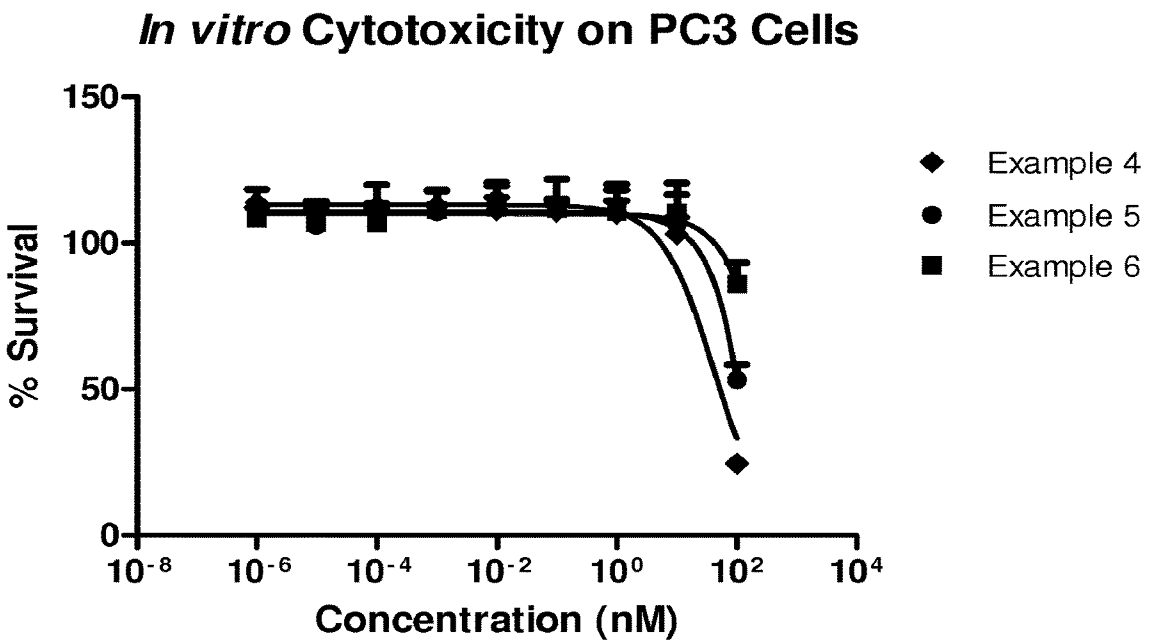
FIG. 12 shows the results for Examples 4, 5, and 6 in an in vitro cytotoxicity experiment using PC3 cells, as described in Example B1. Data is graphed as percent survival versus concentration of test compound, compared to untreated control wells.
Figure 13:
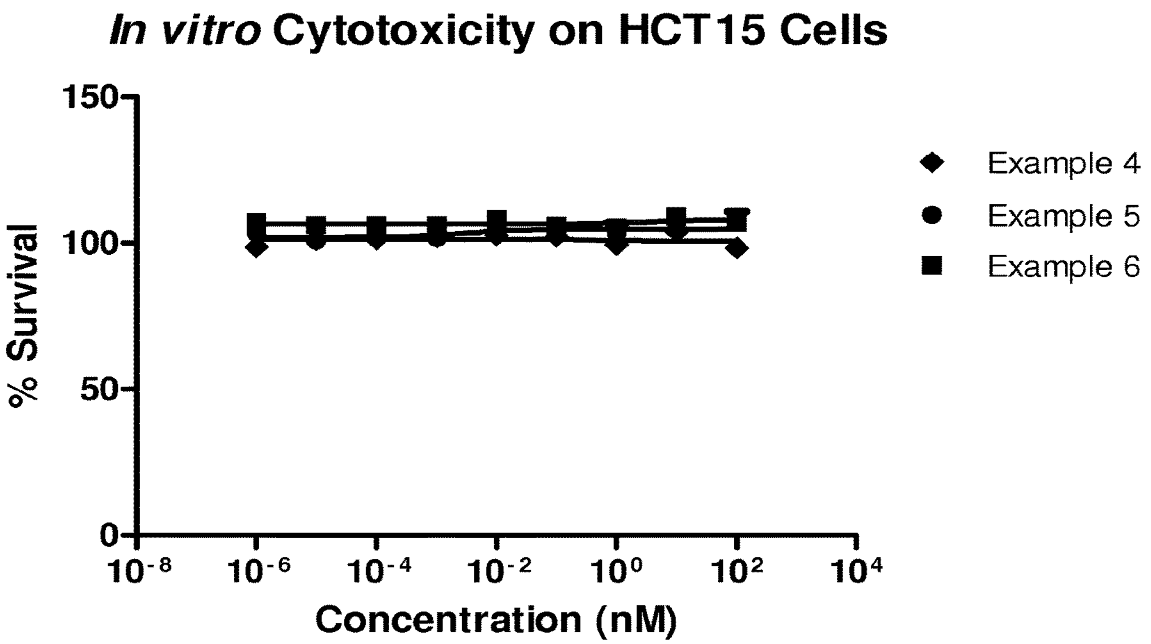
FIG. 13 shows the results for Examples 4, 5, and 6 in an in vitro cytotoxicity experiment using HCT15 cells, as described in Example B1. Data is graphed as percent survival versus concentration of test compound, compared to untreated control wells.
Figure 14:
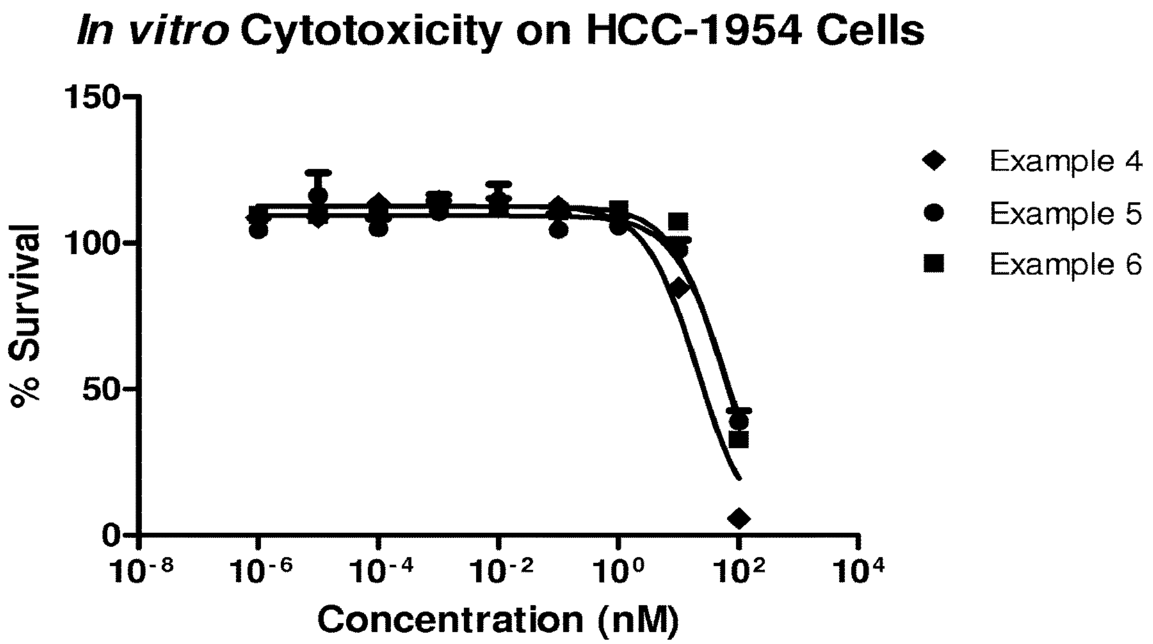
FIG. 14 shows the results for Examples 4, 5, and 6 in an in vitro cytotoxicity experiment using HCC-1954 cells, as described in Example B1. Data is graphed as percent survival versus concentration of test compound, compared to untreated control wells.
Figure 15:
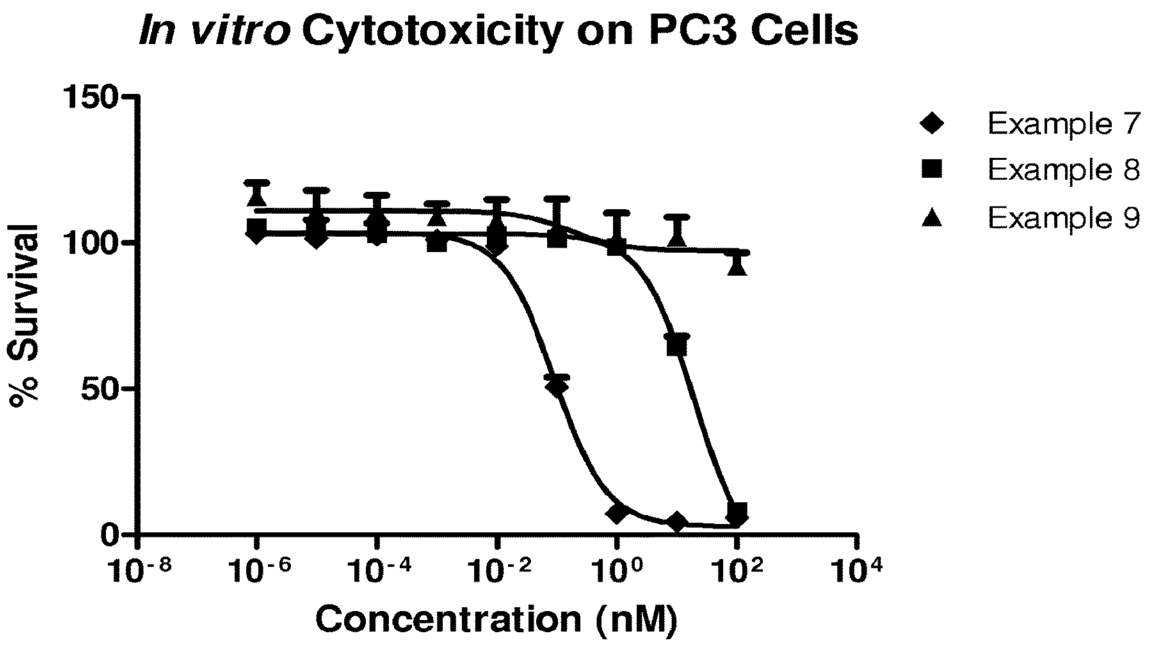
FIG. 15 shows the results for Examples 7, 8, and 9 in an in vitro cytotoxicity experiment using PC3 cells, as described in Example B1. Data is graphed as percent survival versus concentration of test compound, compared to untreated control wells.
Figure 16:
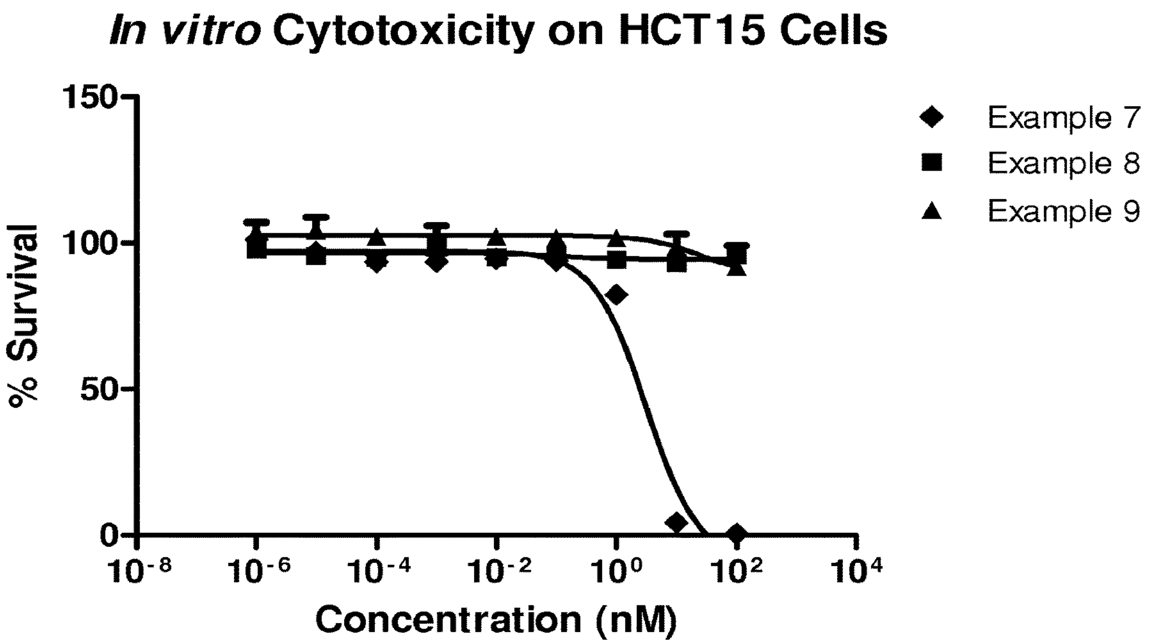
FIG. 16 shows the results for Examples 7, 8, and 9 in an in vitro cytotoxicity experiment using HCT15 cells, as described in Example B1. Data is graphed as percent survival versus concentration of test compound, compared to untreated control wells.
Figure 17:
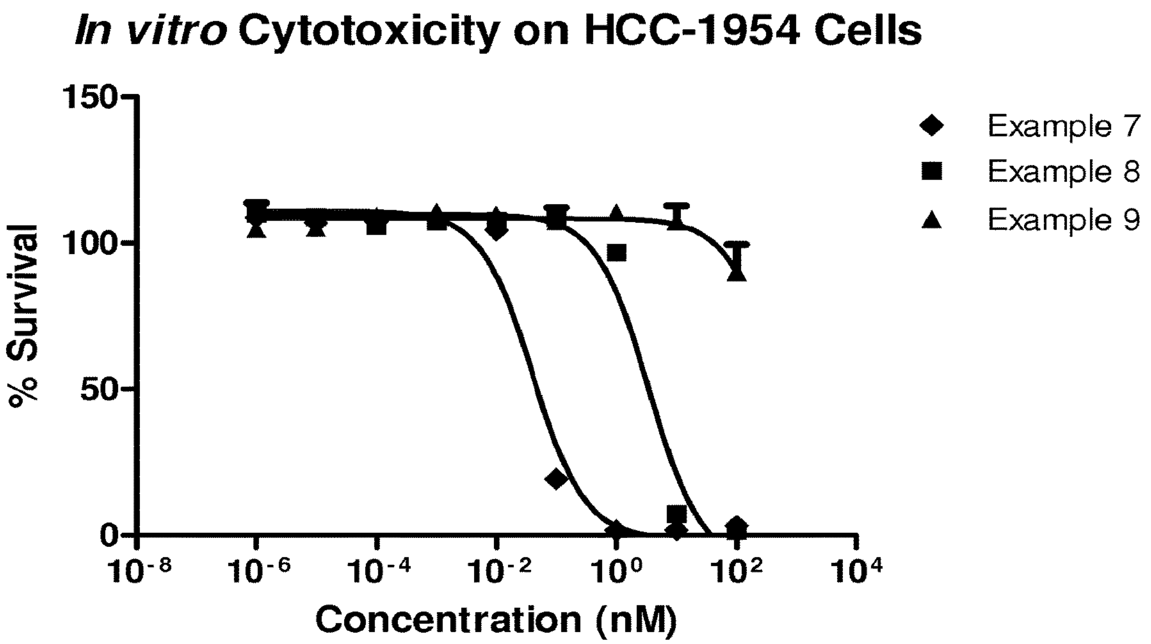
FIG. 17 shows the results for Examples 7, 8, and 9 in an in vitro cytotoxicity experiment using HCC-1954 cells, as described in Example B1. Data is graphed as percent survival versus concentration of test compound, compared to untreated control wells.
Figure 18:
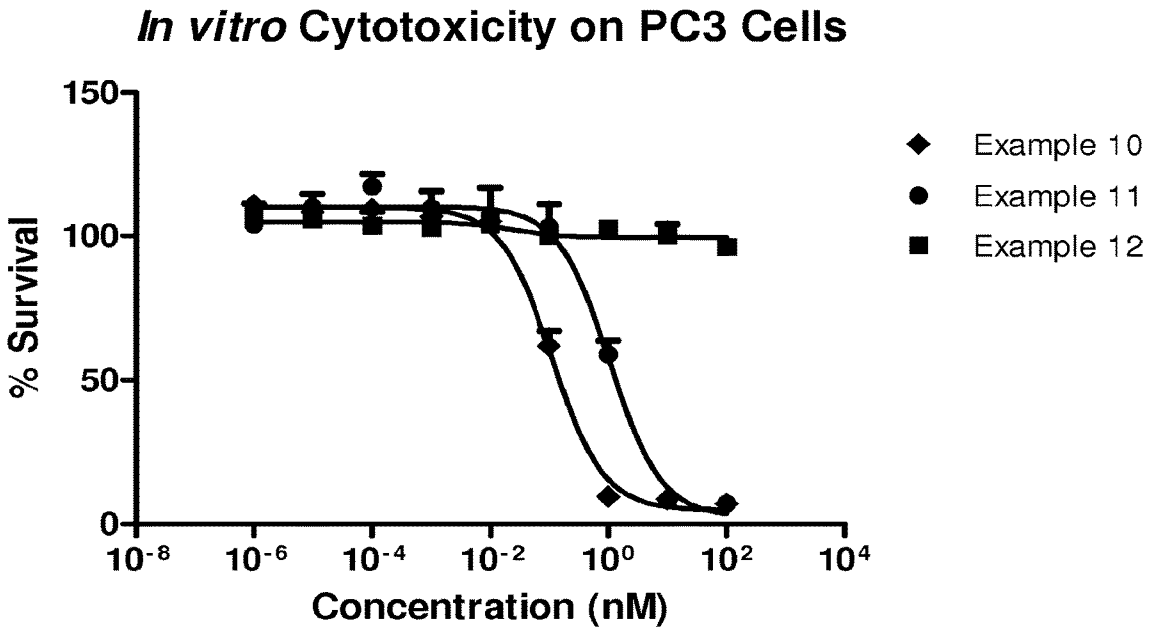
FIG. 18 shows the results for Examples 10, 11, and 12 in an in vitro cytotoxicity experiment using PC3 cells, as described in Example B1. Data is graphed as percent survival versus concentration of test compound, compared to untreated control wells.
Figure 19:
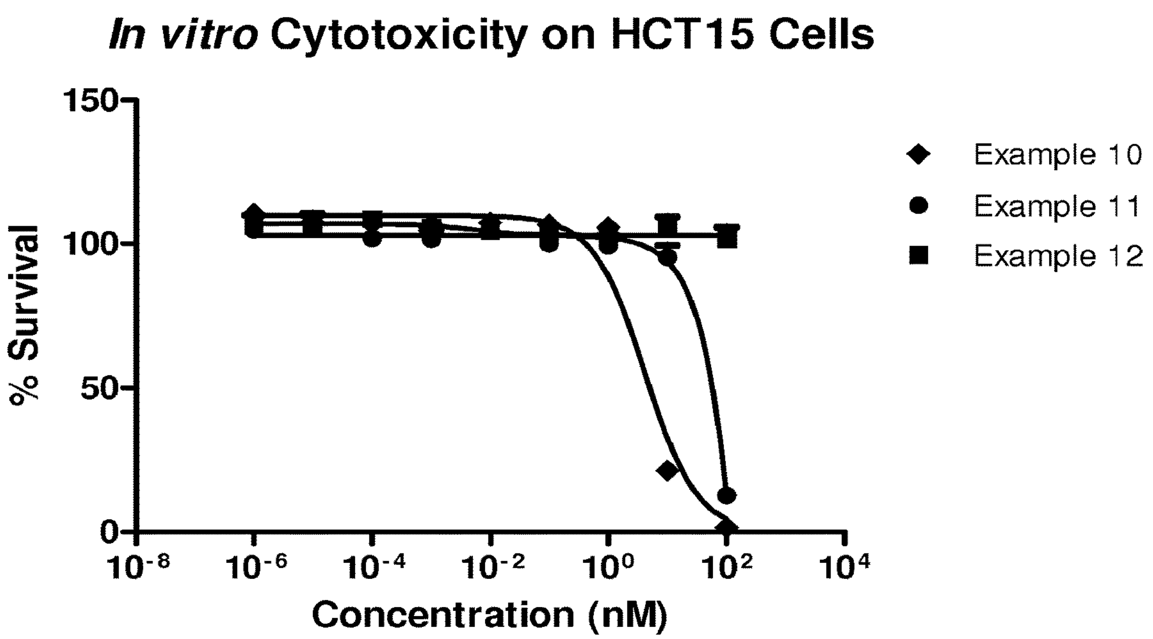
FIG. 19 shows the results for Examples 10, 11, and 12 in an in vitro cytotoxicity experiment using HCT15 cells, as described in Example B1. Data is graphed as percent survival versus concentration of test compound, compared to untreated control wells.
Figure 20:
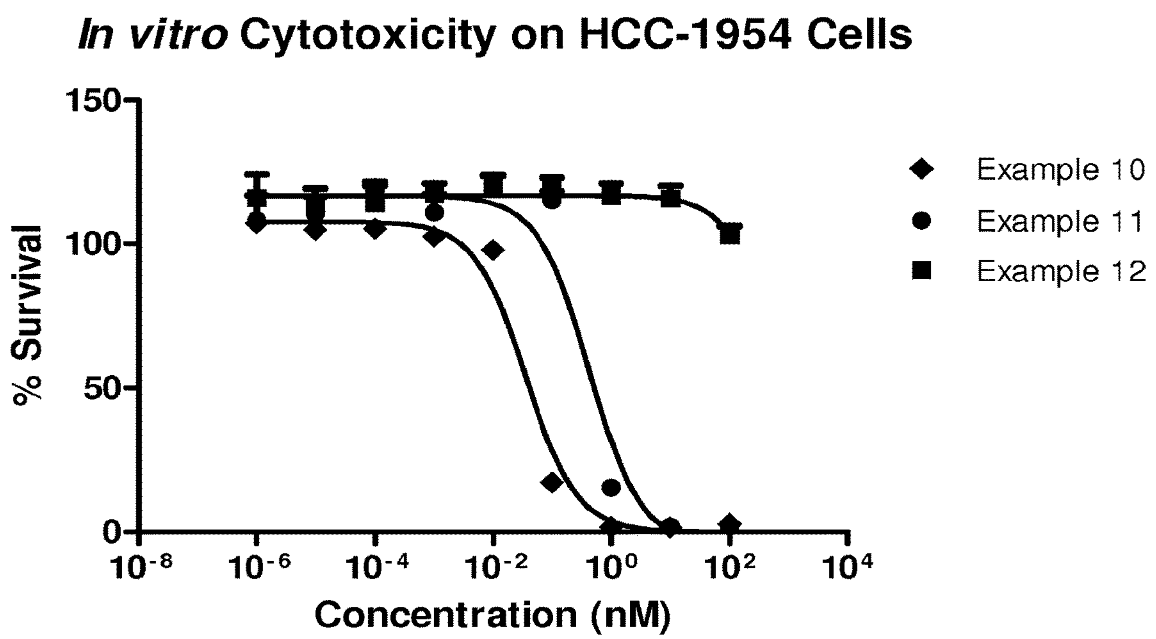
FIG. 20 shows the results for Examples 10, 11, and 12 in an in vitro cytotoxicity experiment using HCC-1954 cells, as described in Example B1. Data is graphed as percent survival versus concentration of test compound, compared to untreated control wells.
Figure 21:
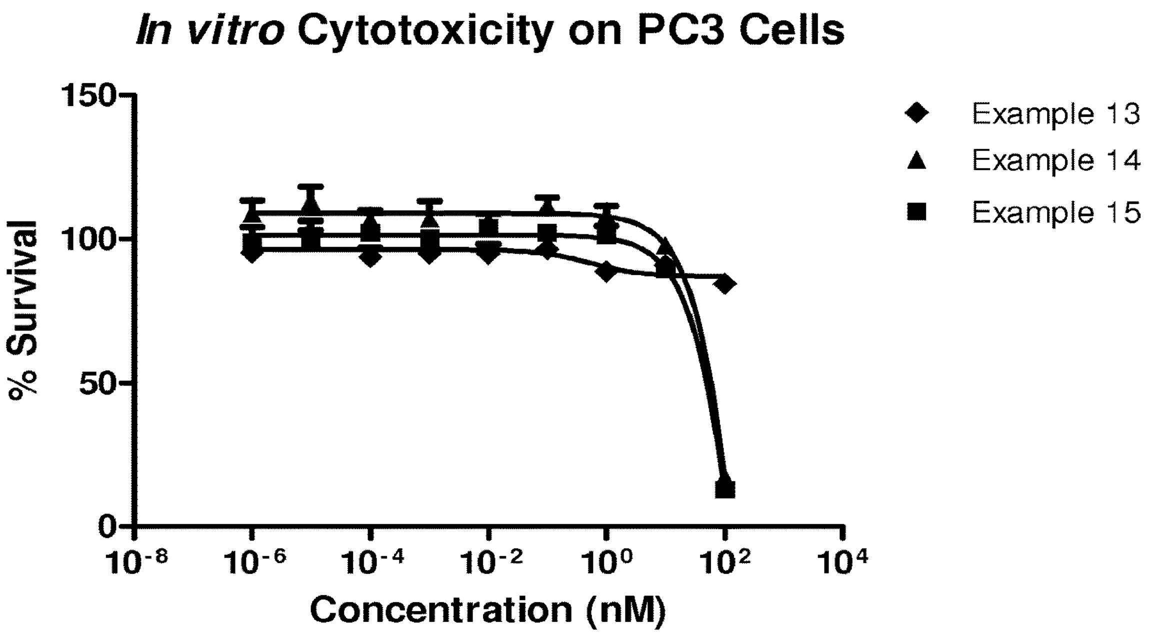
FIG. 21 shows the results for Examples 13, 14, and 15 in an in vitro cytotoxicity experiment using PC3 cells, as described in Example B1. Data is graphed as percent survival versus concentration of test compound, compared to untreated control wells.
Figure 22:
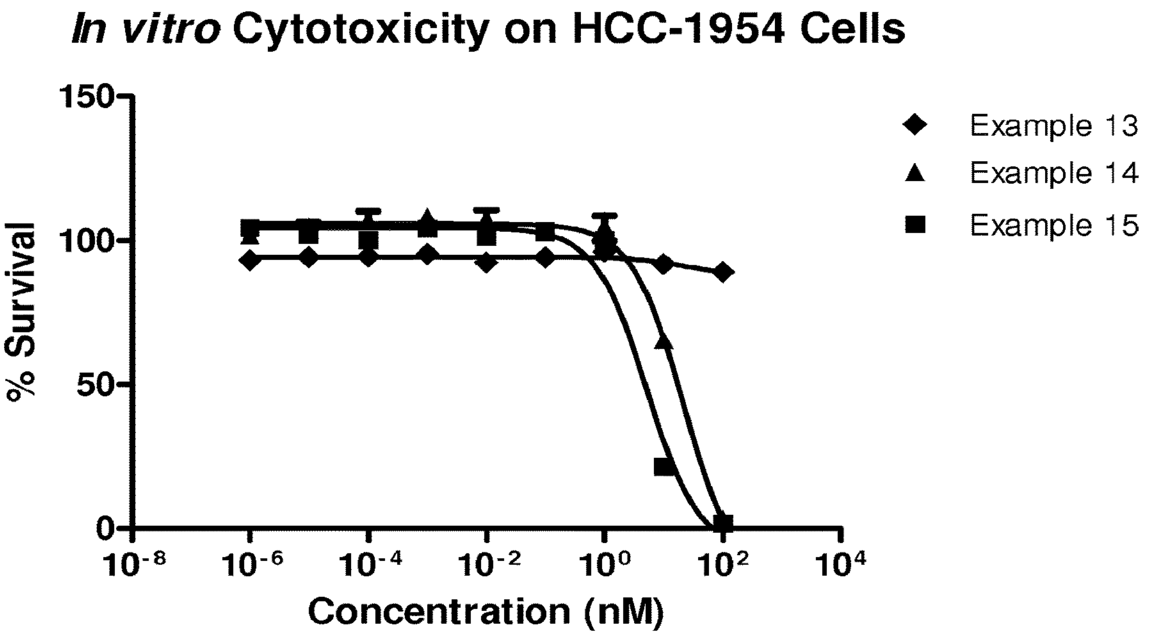
FIG. 22 shows the results for Examples 13, 14, and 15 in an in vitro cytotoxicity experiment using HCC-1954 cells, as described in Example B1. Data is graphed as percent survival versus concentration of test compound, compared to untreated control wells.
Figure 23:
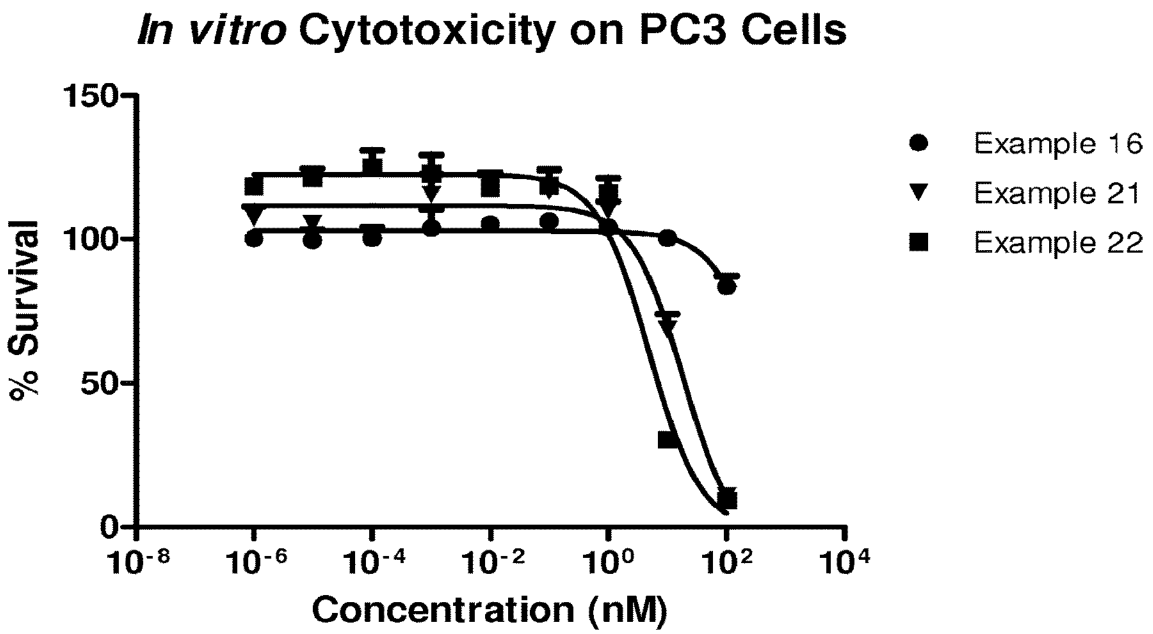
FIG. 23 shows the results for Examples 16, 21, and 22 in an in vitro cytotoxicity experiment using PC3 cells, as described in Example B1. Data is graphed as percent survival versus concentration of test compound, compared to untreated control wells.
Figure 24:
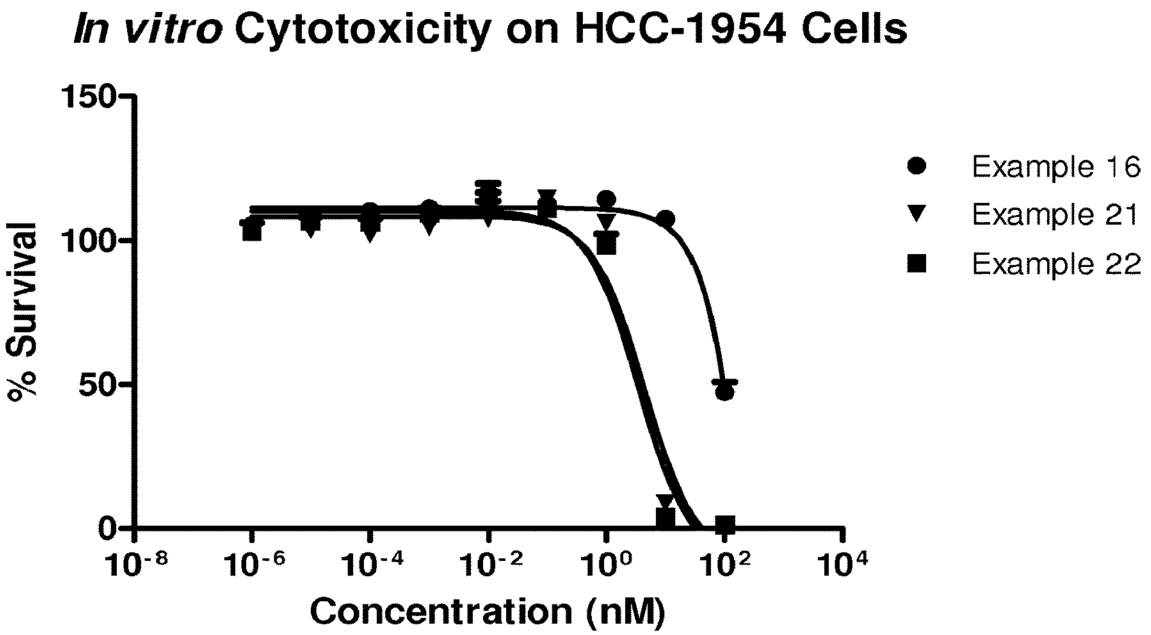
FIG. 24 shows the results for Examples 16, 21, and 22 in an in vitro cytotoxicity experiment using HCC-1954 cells, as described in Example B1. Data is graphed as percent survival versus concentration of test compound, compared to untreated control wells.
Figure 25:
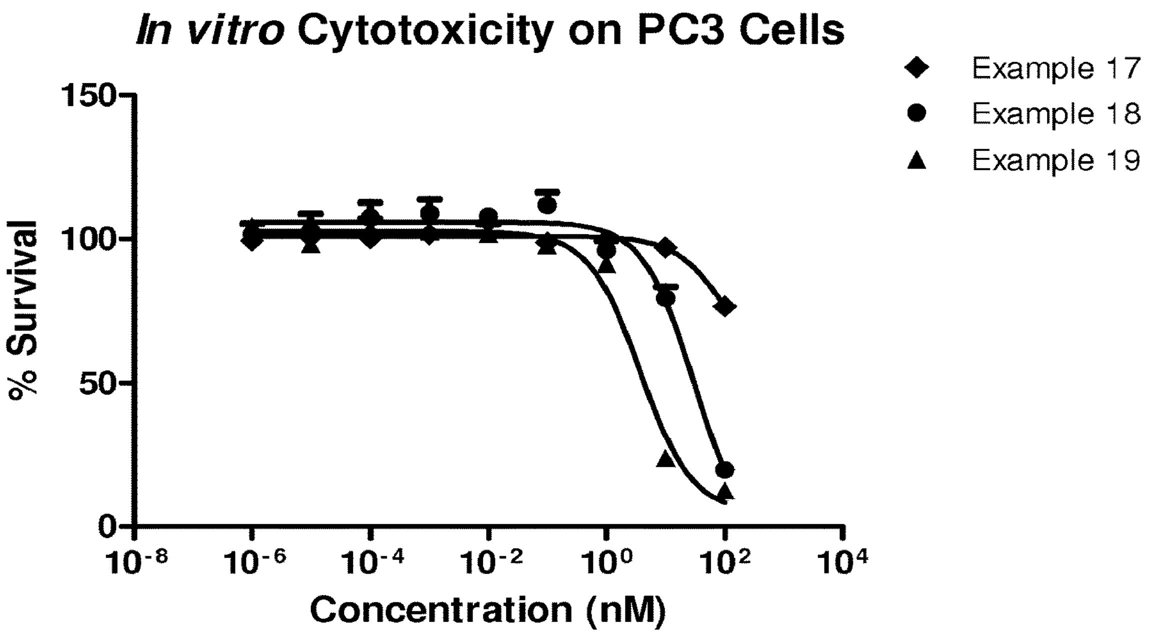
FIG. 25 shows the results for Examples 17, 18, and 19 in an in vitro cytotoxicity experiment using PC3 cells, as described in Example B1. Data is graphed as percent survival versus concentration of test compound, compared to untreated control wells.
Figure 26:
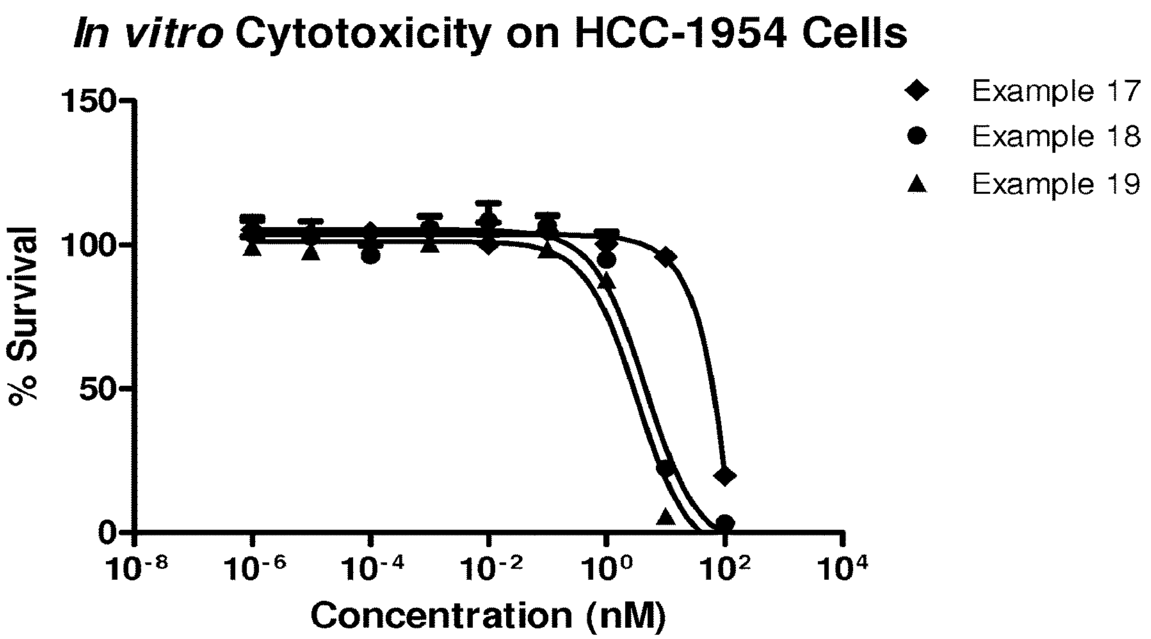
FIG. 26 shows the results for Examples 17, 18, and 19 in an in vitro cytotoxicity experiment using HCC-1954 cells, as described in Example B1. Data is graphed as percent survival versus concentration of test compound, compared to untreated control wells.
Figure 27:
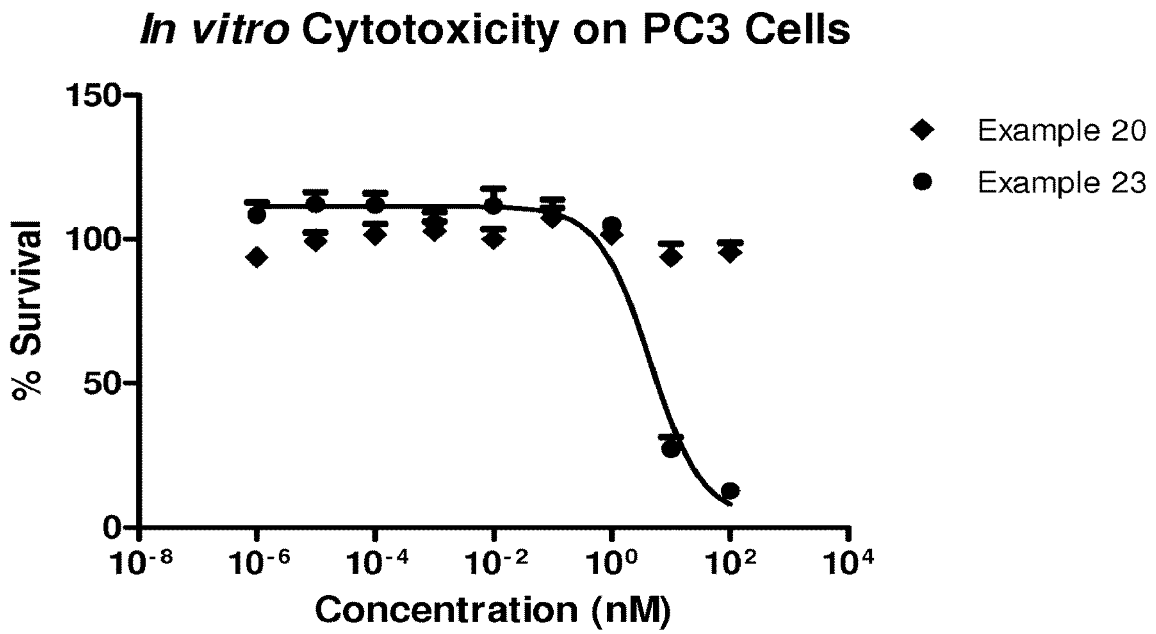
FIG. 27 shows the results for Examples 20 and 23 in an in vitro cytotoxicity experiment using PC3 cells, as described in Example B1. Data is graphed as percent survival versus concentration of test compound, compared to untreated control wells.
Figure 28:
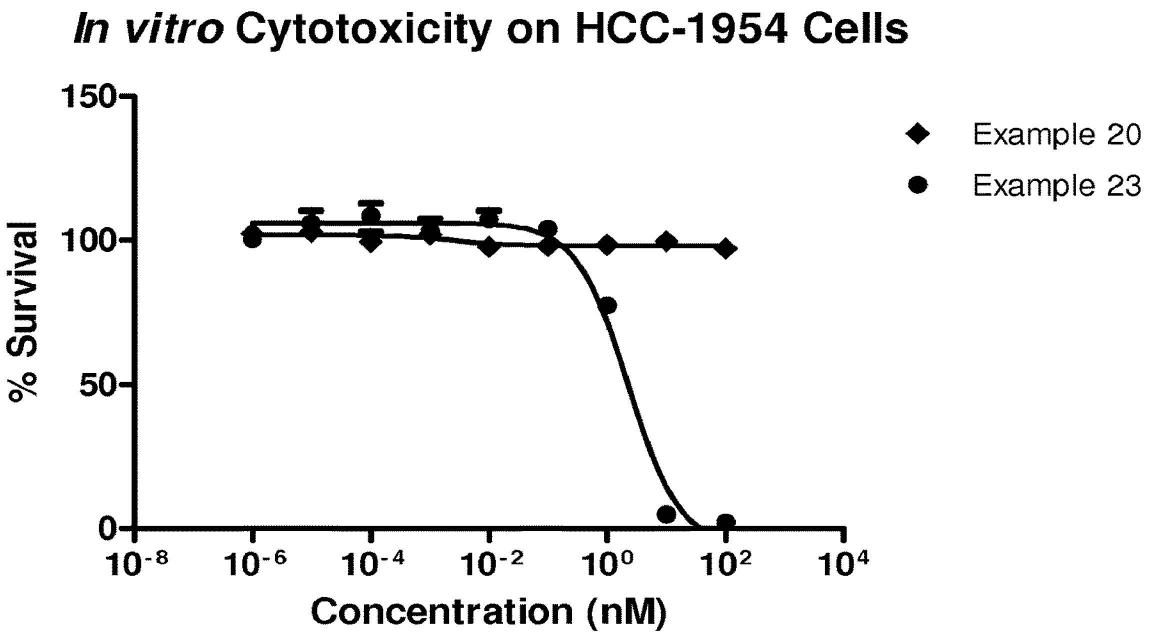
FIG. 28 shows the results for Examples 20 and 23 in an in vitro cytotoxicity experiment using HCC-1954 cells, as described in Example B1. Data is graphed as percent survival versus concentration of test compound, compared to untreated control wells.
Figure 29:
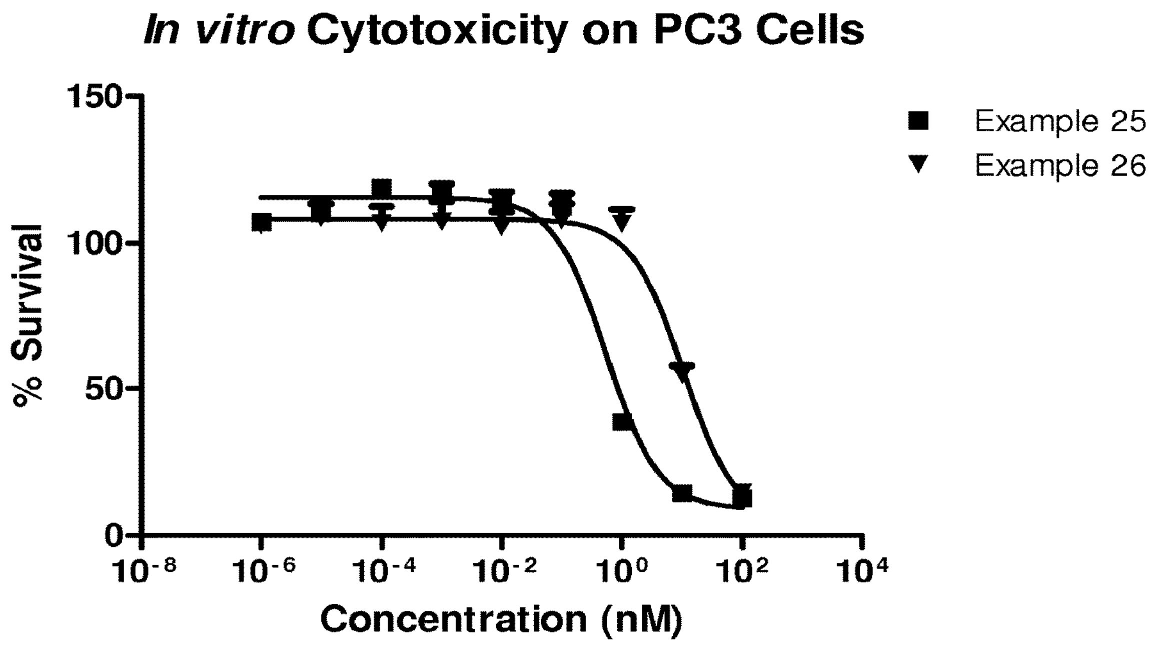
FIG. 29 shows the results for Examples 25 and 26 in an in vitro cytotoxicity experiment using PC3 cells, as described in Example B1. Data is graphed as percent survival versus concentration of test compound, compared to untreated control wells.
Figure 30:
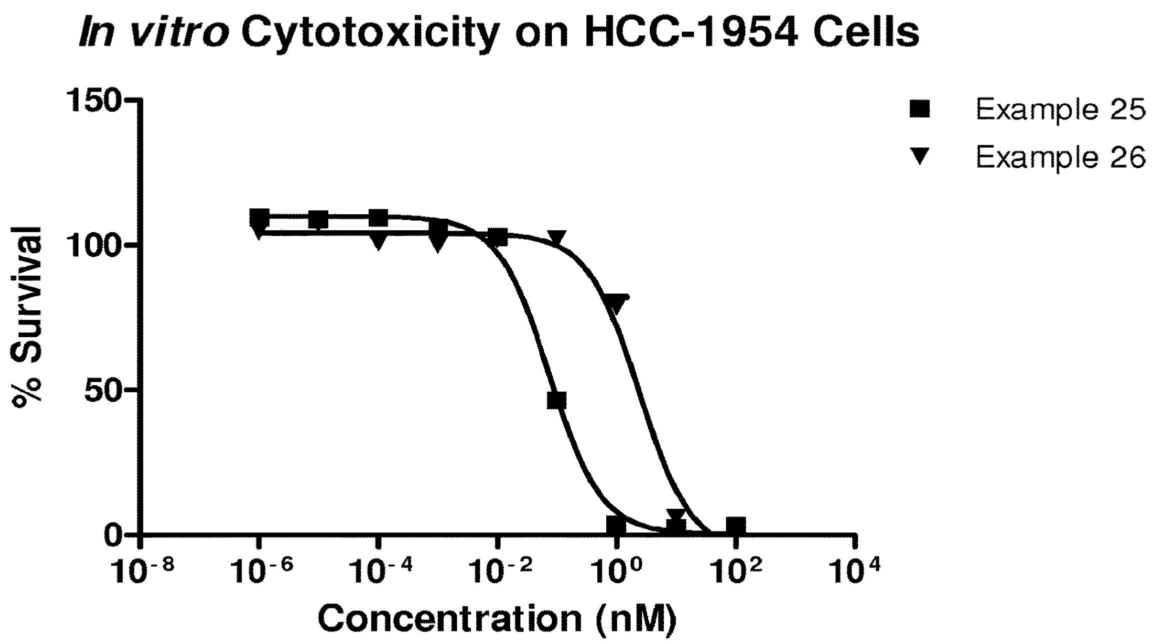
FIG. 30 shows the results for Examples 25 and 26 in an in vitro cytotoxicity experiment using HCC-1954 cells, as described in Example B1. Data is graphed as percent survival versus concentration of test compound, compared to untreated control wells.

The in vitro efficacy of the compounds was measured by evaluating their cytotoxic activity on various cancer cell lines. This assay was conducted in clear tissue-culture treated 96-well plates. The cell lines used were PC3 (human prostate carcinoma), HCC-1954 (human mammary ductal carcinoma), and HCT15 (human colorectal adenocarcinoma, Pgp-expressing). Cells were seeded at approximately 1,000-1,500 cells per well in 50 μL of growth media (RPMI-1640+10% heat-inactivated fetal bovine serum) and incubated overnight at 37° C. with 5% $CO_2$ to allow them to attach. The next day, 50 μL of a 2× stock of vehicle control (DMSO) or compounds at varying concentrations was added to each well in triplicate. In addition, control wells with no cells or untreated cells alone were used. The plates were incubated in the humidified tissue culture incubator with 5% $CO_2$ at 37° C. for 4 to 6 days after addition of compounds to measure cytotoxicity. After 4 to 6 days, 20 μL of Presto-Blue™ Cell Viability Reagent (Life Technologies #A13261) was added per well. Plates were incubated at 37° C. for 1 to 2 h. Fluorescence was recorded at 540 ex/590 em using the Biotek Synergy™ H4 plate reader. Representative data is graphed as percent survival compared to untreated control wells. Data for compounds tested in this assay are graphed as percent survival compared to untreated control wells, as shown in FIGS. 9-30.

Example B2

Determination of Tubulin Polymerization

The inhibition of tubulin polymerization by the compounds described herein was evaluated on bovine brain tubulin. To evaluate the activity of compounds, tubulin was seeded at approximately 400 μg per well in 100 μL of general tubulin buffer, and then treated with 10 μM final concentration of compound in duplicate at the initiation of the assay. Tubulin polymerization assays were usually carried out at 37° C. for 60 min after the addition of test compounds. Tubulin polymerization was determined by absorbance spectroscopy using the optical density value at 340 nm. To assess the amount of polymerized tubulin, the optical density value at 340 nm was obtained each minute after the addition of test compounds. For analysis, the extent of tubulin polymerization by the compound-treated tubulin was compared to that of the control, which was buffer-treated tubulin. In particular, tubulin inhibition studies were performed using HTS-Tubulin Polymerization Assay Kit (Cytoskeleton Inc.; Catalog #BK004P), using the following sample protocol:

1. Pre-warm the spectrophotometer and 96-well plates to 37° C. for 30 min prior to starting the assay. A warm plate is essential for high polymerization activity and reproducible results.
2. Enter all plate reader parameters (Absorbance at 340 nm, 37° C., one read each minute) so that the spectrophotometer is ready for use. Once the tubulin is aliquoted into the 37° C. wells, the reading must begin immediately.
3. Warm 500 μL of general tubulin buffer to room temperature. Warm buffer is needed for tubulin ligand dilutions.
4. Paclitaxel is included as a control. Use 10 μL of Paclitaxel per well, which brings the final concentration to 10 μM final.
5. Make cold assay buffer: general tubulin buffer, 1 mM GTP, 10% glycerol.
6. Resuspend 4 mgs of tubulin with 1 mL of cold assay buffer to bring the final protein concentration of 4 mg/mL. Place the tubes on ice and allow 3 min for the complete resuspension of the protein.
7. Prepare selected compound at 10× concentration in assay buffer.
8. Pipette 10 μL of the 10× concentrated compound into the required number of wells of the pre-warmed plate. Incubate the plate for 2 min at 37° C.
9. Pipette 10 μL of assay buffer only into two control wells (buffer-treated tubulin).
10. Pipette 100 μL of tubulin into the required number of wells (two wells should be the zero compound controls, which are buffer-treated).
11. Immediately place the plate into the spectrophotometer at 37° C. and start recording the optical density at 340 nm each minute. Increasing optical density values at 340 nm equate to increasing tubulin polymerization.

Figure 2:
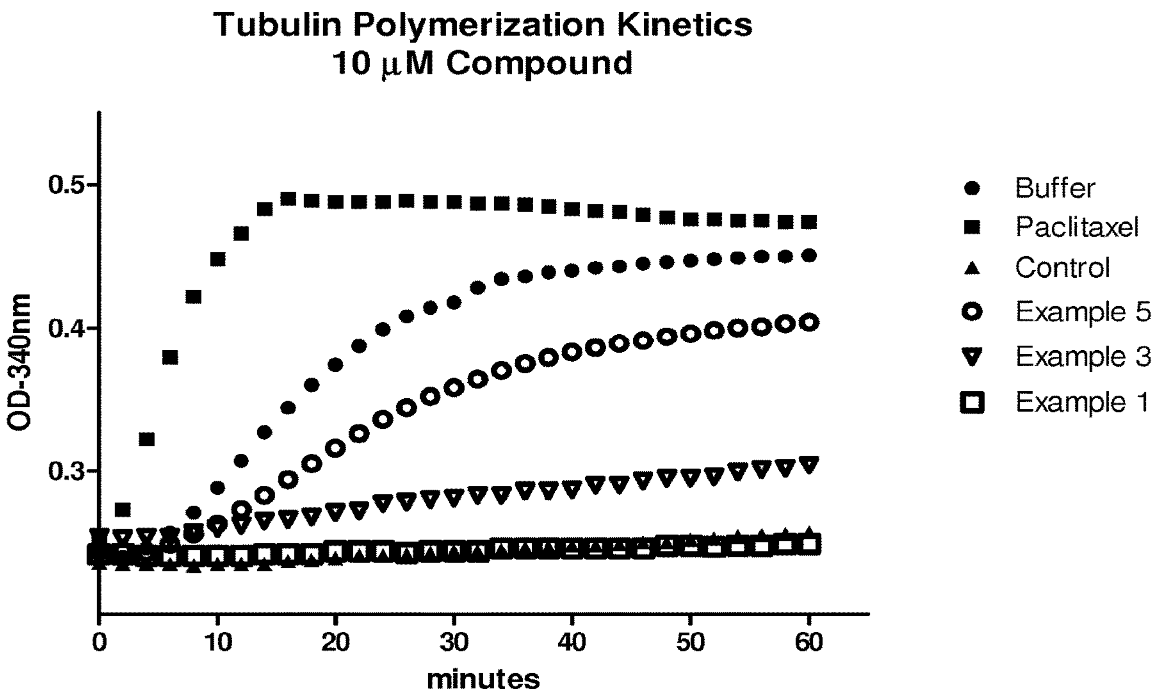
FIG. 2 shows in vitro tubulin polymerization data for tubulin treated with Example 1, Example 3, and Example 5. Untreated (buffer) tubulin shows the basal level of tubulin polymerization. A tubulin stabilizer (Paclitaxel) and a tubulin de-stabilizer (Control) were used as controls. All compounds were used at a final concentration of 10 μM.
Figure 3:
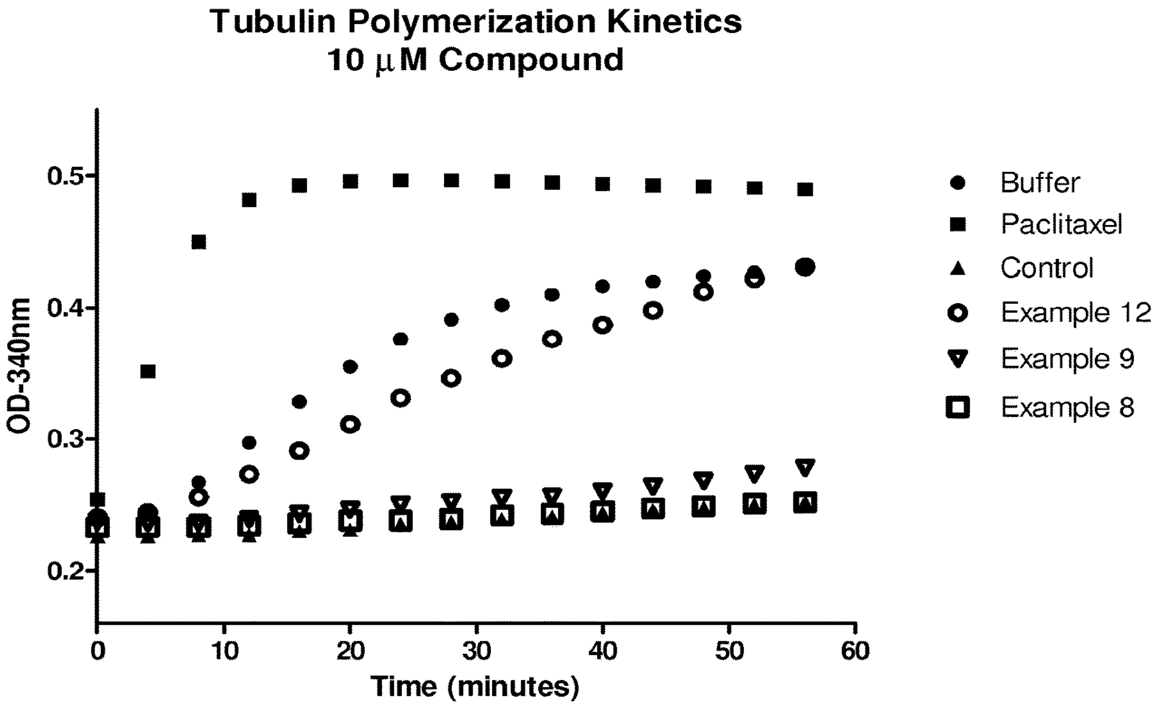
FIG. 3 shows in vitro tubulin polymerization data for tubulin treated with Example 8, Example 9, and Example 12. Untreated (buffer) tubulin shows the basal level of tubulin polymerization. A tubulin stabilizer (Paclitaxel) and a tubulin de-stabilizer (Control) were used as controls. All compounds were used at a final concentration of 10 μM.
Figure 4:
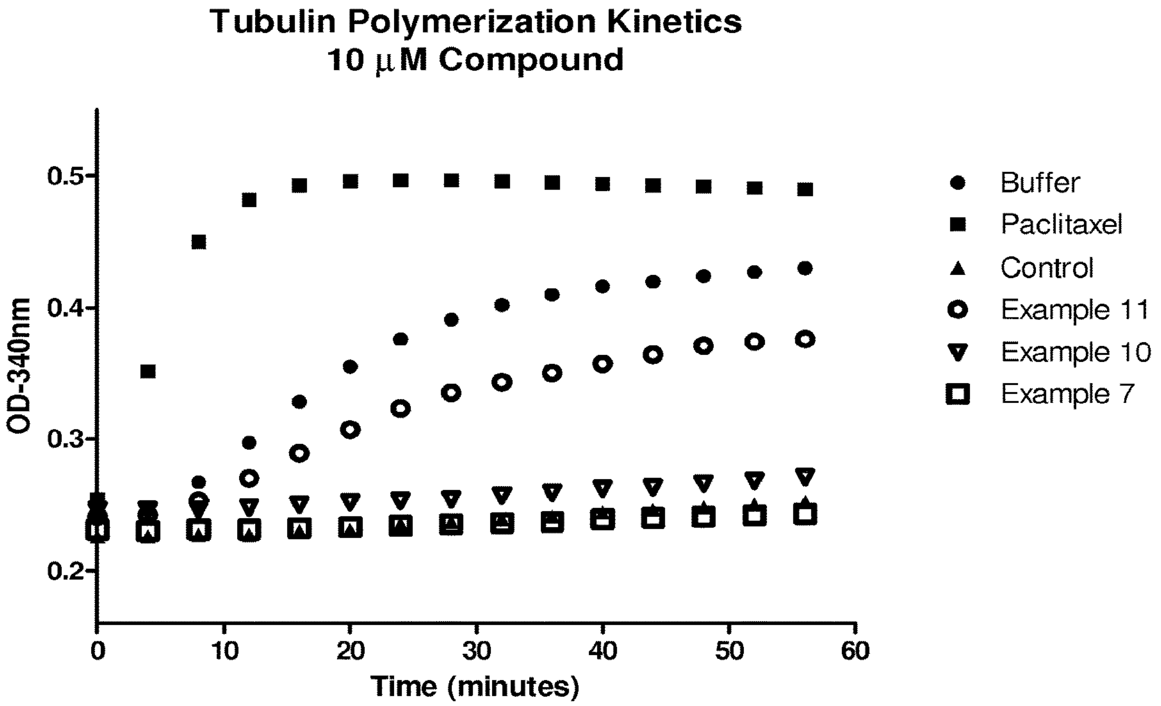
FIG. 4 shows in vitro tubulin polymerization data for tubulin treated with Example 7, Example 10, and Example 11. Untreated (Buffer) tubulin shows the basal level of tubulin polymerization. A tubulin stabilizer (Paclitaxel) and a tubulin de-stabilizer (Control) were used as controls. All compounds were used at a final concentration of 10 μM.
Figure 5:
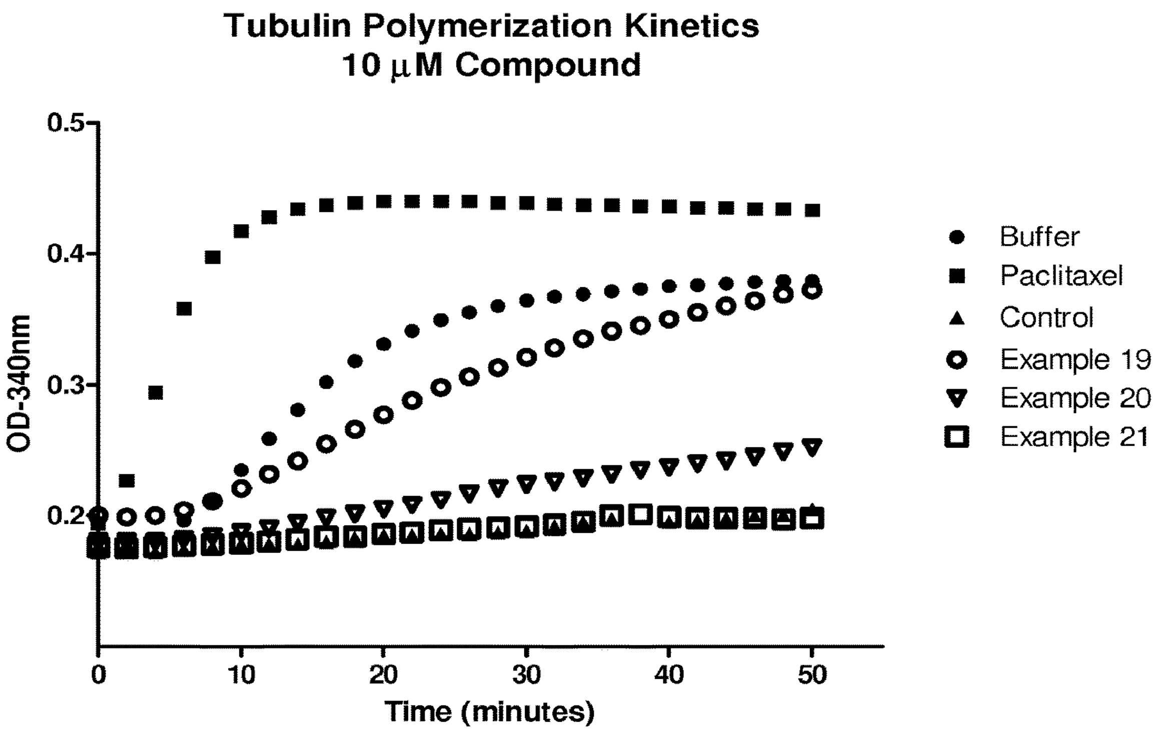
FIG. 5 shows in vitro tubulin polymerization data for tubulin treated with Example 19, Example 20, and Example 21. Untreated (Buffer) tubulin shows the basal level of tubulin polymerization. A tubulin stabilizer (Paclitaxel) and a tubulin de-stabilizer (Control) were used as controls. All compounds were used at a final concentration of 10 μM.
Figure 6:
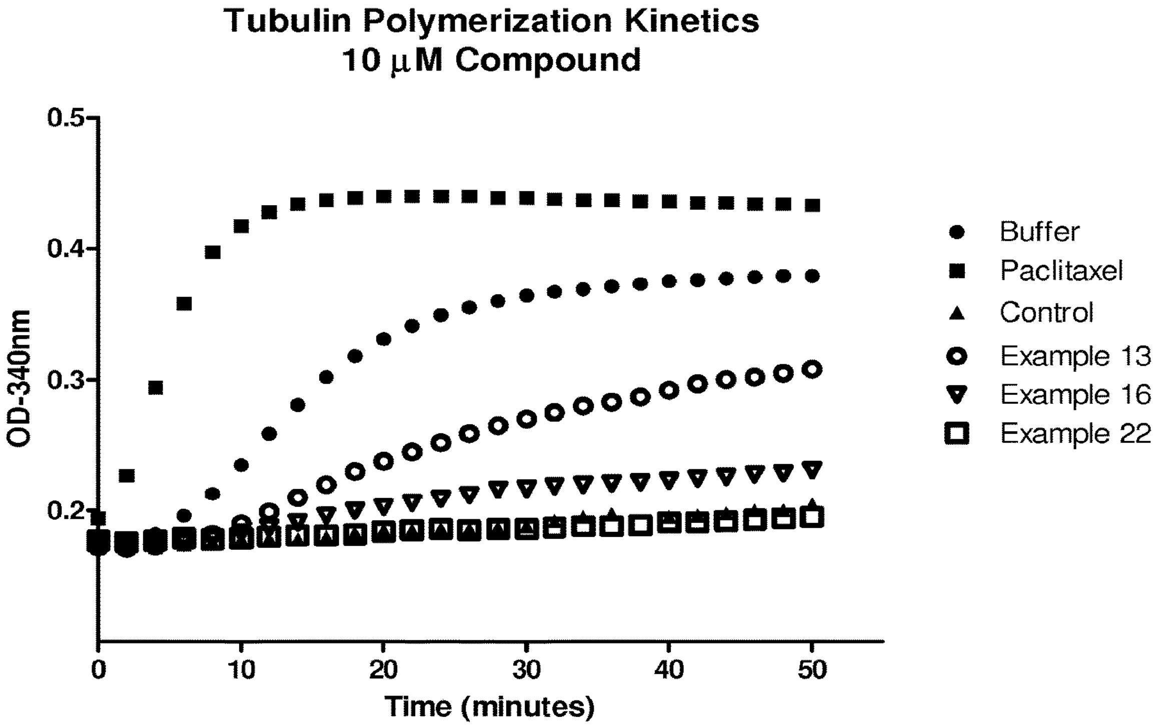
FIG. 6 shows in vitro tubulin polymerization data for tubulin treated with Example 13, Example 16, and Example 22. Untreated (Buffer) tubulin shows the basal level of tubulin polymerization. A tubulin stabilizer (Paclitaxel) and a tubulin de-stabilizer (Control) were used as controls. All compounds were used at a final concentration of 10 μM.
Figure 7:
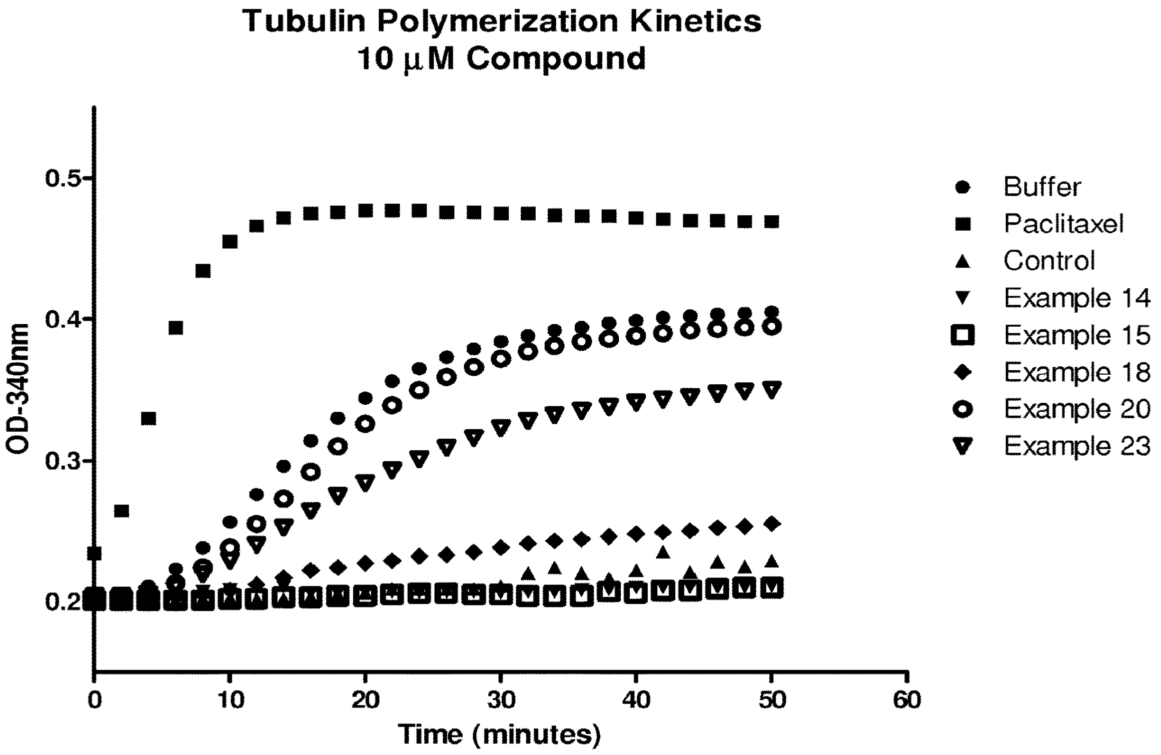
FIG. 7 shows in vitro tubulin polymerization data for tubulin treated with Example 14, Example 15, Example 18, Example 20, and Example 23. Untreated (Buffer) tubulin shows the basal level of tubulin polymerization. A tubulin stabilizer (Paclitaxel) and a tubulin de-stabilizer (Control) were used as controls. All compounds were used at a final concentration of 10 μM.
Figure 8:
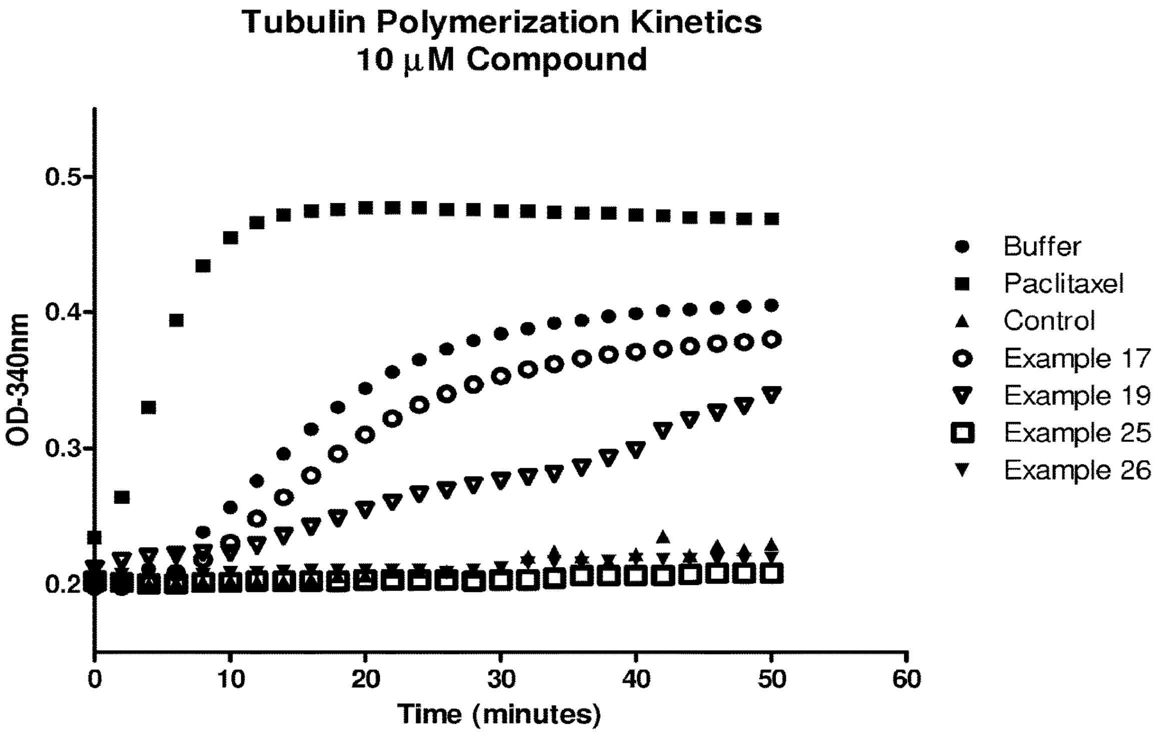
FIG. 8 shows in vitro tubulin polymerization data for tubulin treated with Example 17, Example 19, Example 25, and Example 26. Untreated (Buffer) tubulin shows the basal level of tubulin polymerization. A tubulin stabilizer (Paclitaxel) and a tubulin de-stabilizer (Control) were used as controls. All compounds were used at a final concentration of 10 μM.

Data for compounds tested in this assay are presented in FIGS. 1-8.

Example B3

Determination of In Vivo Efficacy of Test Compounds: Efficacy Evaluation in Subcutaneously Established Human Bladder Cancer Cell Line SW780 Implanted in ICR SCID Mice For animal in vivo studies, the test compounds are diluted with 20 mM Histidine, 5% Sucrose, pH 6 with 15% DMSO. Male ICR SCID mice (Taconic Farm, Hudson, N.Y.) are housed in standard rodent micro isolator cages. Environment controls for the animal rooms are set to maintain a temperature between 20-24° C., a relative humidity between 30% to 70%, and an approximate 12 h light/12 h dark cycle. Food and water are provided ad libitum. After 72 h of acclimatization, the mice are implanted with SW780 human bladder cancer cells ($2\times10^6$ cells/mouse), suspended in 50% complete cultrex (Trevigen, Inc.) mixed with PBS (Gibco), and the tumor growth rate is monitored. When the average tumor volume reaches ~200 $mm^3$, tumors are size-matched and mice are randomized to treatment groups (n=8 or 10). The tumor-bearing mice are treated i.v. with Vehicle or test compound at 2 or 4 mg/kg (mpk) on a QW dosing schedule for 3 weeks. Tumor volume is assessed twice weekly using caliper measurement.

While the foregoing written description of the compounds, uses, and methods described herein enables one of ordinary skill to make and use the compounds, uses, and methods described herein, those of ordinary skill will understand and appreciate the existence of variations, combinations, and equivalents of the specific embodiment, method, and examples herein. The compounds, uses, and methods provided herein should therefore not be limited by the above-described embodiments, methods, or examples, but rather encompasses all embodiments and methods within the scope and spirit of the compounds, uses, and methods provided herein.

The invention claimed is:

1. A method of treating cancer in a subject in need thereof, comprising administering to the subject a composition comprising an effective amount of a compound of Formula (I) or a pharmaceutically acceptable salt thereof:

(I)

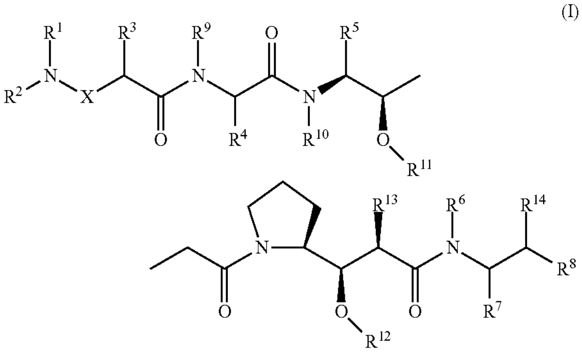

wherein:

$R^1$ and $R^2$ are each independently —H or —$C_{1-6}$ alkyl;

X is absent;

$R^3$ is

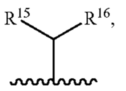

wherein $R^{15}$ and $R^{16}$ are each independently —H, —OH, or —$C_{1-6}$ alkyl;

$R^4$ is

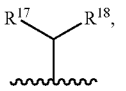

wherein:

$R^{17}$ is —H, —OH, —$NH_2$, —SH, —$N_3$, —$CO_2H$, —$C_{1-6}$ alkenyl, —$C_{1-6}$ alkynyl, —$C_{1-6}$ alkyl-OH, —$C_{1-6}$ alkyl-$NH_2$, —$C_{1-6}$ alkyl-SH, —$C_{1-6}$ alkyl-$N_3$ or —$C_{1-6}$ alkyl-$CO_2H$; and $R^{18}$ is —H, —OH, —$NH_2$, —SH, —$N_3$, —$CO_2H$, —$C_{1-6}$ alkyl, —$C_{1-6}$ alkenyl, —$C_{1-6}$ alkynyl, —$C_{1-6}$ alkyl-OH, —$C_{1-6}$ alkyl-$NH_2$, —$C_{1-6}$ alkyl-SH, —$C_{1-6}$ alkyl-$N_3$ or —$C_{1-6}$ alkyl-$CO_2H$;

$R^5$ is sec-butyl or isobutyl;

$R^6$ is —H or alkyl;

$R^7$ is —H, alkyl, —$CO_2R^a$, —$CONR^bR^c$, or substituted or unsubstituted heterocyclic ring, wherein $R^a$ is —H or —$C_{1-6}$ alkyl; and $R^b$ and $R^c$ are each independently —H or —$C_{1-6}$ alkyl;

$R^8$ is —H, —$C_{1-6}$ alkyl, substituted or unsubstituted phenyl, or substituted or unsubstituted heterocyclic ring;

$R^9$ is —H or —$C_{1-6}$ alkyl or $R^9$ is taken together with $R^4$ and the atoms to which they are attached to form a substituted or unsubstituted heterocycloalkyl ring;

$R^{10}$ is —H or —$C_{1-6}$ alkyl;

$R^{11}$ is —H or —$C_{1-6}$ alkyl;

$R^{12}$ is —H or —$C_{1-6}$ alkyl;

$R^{13}$ is —H or —$C_{1-6}$ alkyl; and $R^{14}$ is —H, —OH, or —$C_{1-6}$ alkyl.

2. The method of claim 1, wherein:

$R^4$ is

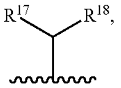

wherein:

$R^{17}$ is —OH, —$NH_2$, —SH, —$N_3$, —$CO_2H$, —$C_{1-6}$-alkyl-$NH_2$, —$C_{1-6}$-alkynyl, —$C_{1-6}$-alkenyl, or —$C_{1-6}$-alkyl-$N_3$; and $R^{18}$ is —H or —$C_{1-6}$-alkyl;

$R^5$ is sec-butyl;

$R^6$ is —H;

$R^7$ is —H, —$C_{1-6}$-alkyl, —$CO_2R^a$, —$CONR^bR^c$, tetrazolyl or thiazolyl;

$R^9$ is —H; and $R^{10}$, $R^{11}$, $R^{12}$, and $R^{13}$ are each independently —$C_{1-6}$-alkyl.

3. The method of claim 1, wherein:

$R^1$ and $R^2$ are each independently —H or methyl;

$R^3$ is

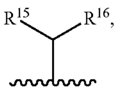

wherein $R^{15}$ and $R^{16}$ are each independently —H, —OH, or methyl;

$R^4$ is

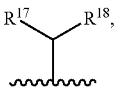

wherein:

$R^{17}$ is —OH, —$NH_2$, —SH, —$N_3$, —$CO_2H$, aminomethyl, —$C_{1-6}$ alkynyl, —$C_{1-6}$ alkenyl, or azidomethyl; and $R^{18}$ is —H or methyl;

$R^5$ is sec-butyl;

$R^6$ is —H;

$R^7$ is —H, methyl, —$CO_2R^a$, or —$CONR^bR^c$, wherein:

$R^a$ is —H or methyl; and $R^b$ and $R^c$ are each independently —H or methyl;

$R^8$ is —H, methyl, ethyl, pyridinyl, piperidinyl, unsubstituted phenyl, or phenyl substituted with halo;

$R^9$ is —H;

$R^{10}$, $R^{11}$, $R^{12}$, and $R^{13}$ are each methyl; and $R^{14}$ is —H, methyl, or —OH.

4. The method of claim 1, wherein:

$R^4$ is

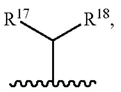

wherein:

$R^{17}$ is —$N_3$; and $R^{18}$ is —H or methyl;

$R^5$ is sec-butyl;

$R^6$ is —H;

$R^7$ is —H, —$C_{1-6}$-alkyl, —$CO_2R^a$, —$CONR^bR^c$, tetrazolyl, or thiazolyl;

$R^9$ is —H; and $R^{10}$, $R^{11}$, $R^{12}$, and $R^{13}$ are each independently —$C_{1-6}$-alkyl.

5. The method of claim 1, wherein $R^1$ and $R^2$ are each methyl;

$R^3$ is

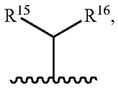

wherein $R^{15}$ and $R^{16}$ are each methyl;

$R^4$ is

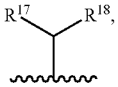

wherein:

$R^{17}$ is —$N_3$, —$NH_2$, —OH, —SH; and $R^{18}$ is —H or methyl;

$R^5$ is sec-butyl;

$R^6$ is —H;

$R^7$ is —$CO_2R^a$ or —$CONR^bR^c$;

$R^8$ is phenyl;

$R^9$ is —H;

$R^{10}$, $R^{11}$, $R^{12}$, and $R^{13}$ are each methyl; and $R^{14}$ is —H.

6. The method of claim 1, wherein:

$R^4$ is

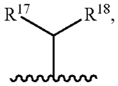

wherein:

$R^{17}$ is —$N_3$; and $R^{18}$ is —H or —$C_{1-6}$ alkyl;

$R^5$ is sec-butyl;

$R^6$ is —H;

$R^7$ is —$C_{1-6}$-alkyl, —$CONR^bR^c$, tetrazolyl, or thiazolyl;

$R^9$ is —H; and $R^{10}$, $R^{11}$, $R^{12}$, and $R^{13}$ are each independently —$C_{1-6}$-alkyl.

7. The method of claim 1, wherein:

$R^4$ is

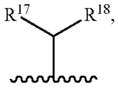

wherein:

$R^{17}$ is —$N_3$; and $R^{18}$ is —H or —$C_{1-6}$-alkyl;

$R^5$ is sec-butyl;

$R^6$ is —H;

$R^7$ is —$CONR^bR^c$, wherein $R^b$ and $R^c$ are each —H;

$R^9$ is —H; and $R^{10}$, $R^{11}$, $R^{12}$, and $R^{13}$ are each independently —$C_{1-6}$-alkyl.

8. The method of claim 1, wherein the cancer is prostate cancer, pancreatic cancer, breast cancer, or colorectal cancer.

9. The method of claim 1, comprising administering the composition in combination with one or more additional chemotherapeutic active agents.

10. A method of treating cancer in a subject in need thereof, comprising administering to the subject a composition comprising an effective amount of a compound that is selected from the group consisting of:

(S)-methyl 2-((2R,3R)-3-((S)-1-((3R,4S,5S)-4-((S)-2-((S)-2-(dimethylamino)-3-methylbutanamido)-3-hydroxy-N-methylpropanamido)-3-methoxy-5-methylheptanoyl)pyrrolidin-2-yl)-3-methoxy-2-methylpropanamido)-3-phenylpropanoate;

(S)-methyl 2-((2R,3R)-3-((S)-1-((3R,4S,5S)-4-((2S,3R)-2-((S)-2-(dimethylamino)-3-methylbutanamido)-3-hydroxy-N-methylbutanamido)-3-methoxy-5-methylheptanoyl)pyrrolidin-2-yl)-3-methoxy-2-methylpropanamido)-3-phenylpropanoate;

(S)-2-(dimethylamino)-N—((S)-3-hydroxy-1-(((3R,4S,5i)-3-methoxy-1-((S)-2-((1R,2R)-1-methoxy-2-methyl-3-oxo-3-((2-(pyridin-2-yl)ethyl)amino)propyl)pyrrolidin-1-yl)-5-methyl-1-oxoheptan-4-yl)(methyl)amino)-1-oxopropan-2-yl)-3-methylbutanamide;

(2S,3R)-2-((S)-2-(dimethylamino)-3-methylbutanamido)-3-hydroxy-N-((3R,4S,5S)-3-methoxy-1-((S)-2-((1R,2R)-1-methoxy-2-methyl-3-oxo-3-((2-(pyridin-2-yl)ethyl)amino)propyl)pyrrolidin-1-yl)-5-methyl-1-oxoheptan-4-yl)-N-methylbutanamide;

(2S)-2-(dimethylamino)-N-((2S)-3-hydroxy-1-(((3R,4S,5S)-3-methoxy-1-((2S)-2-((1R,2R)-1-methoxy-2-methyl-3-oxo-3-((2-(piperidin-2-yl)ethyl)amino)propyl)pyrrolidin-1-yl)-5-methyl-1-oxoheptan-4-yl)(methyl)amino)-1-oxopropan-2-yl)-3-methylbutanamide;

(2S,3R)-2-((S)-2-(dimethylamino)-3-methylbutanamido)-3-hydroxy-N-((3R,4S,5S)-3-methoxy-1-((2S)-2-((1R,2R)-1-methoxy-2-methyl-3-oxo-3-((2-(piperidin-2-yl)ethyl)amino)propyl)pyrrolidin-1-yl)-5-methyl-1-oxoheptan-4-yl)-N-methylbutanamide;

(S)-methyl 2-((2R,3R)-3-((S)-1-((3R,4S,5S)-4-((2S,3S)-3-azido-2-((S)-2-(dimethylamino)-3-methylbutanamido)-N-methylbutanamido)-3-methoxy-5-methylheptanoyl)pyrrolidin-2-yl)-3-methoxy-2-methylpropanamido)-3-phenylpropanoate;

(S)-methyl 2-((2R,3R)-3-((S)-1-((3R,4S,5S)-4-((S)-3-amino-2-((S)-2-(dimethylamino)-3-methylbutanamido)-N-methylpropanamido)-3-methoxy-5-methylheptanoyl)pyrrolidin-2-yl)-3-methoxy-2-methylpropanamido)-3-phenylpropanoate;

(S)—N—((S)-3-amino-1-(((3R,4S,5S)-3-methoxy-1-((S)-2-((1R,2R)-1-methoxy-2-methyl-3-oxo-3-((2-(pyridin-2-yl)ethyl)amino)propyl)pyrrolidin-1-yl)-5-methyl-1-oxoheptan-4-yl)(methyl)amino)-1-oxopropan-2-yl)-2-(dimethylamino)-3-methylbutanamide;

(S)-methyl 2-((2R,3R)-3-((S)-1-((3R,4S,5S)-4-((S)-3-azido-2-((S)-2-(dimethylamino)-3-methylbutanamido)-N-methylpropanamido)-3-methoxy-5-methylheptanoyl)pyrrolidin-2-yl)-3-methoxy-2-methylpropanamido)-3-phenylpropanoate;

(S)-methyl 2-((2R,3R)-3-((S)-1-((3R,4S,5S)-4-((S)-4-azido-2-((S)-2-(dimethylamino)-3-methylbutanamido)-N-methylbutanamido)-3-methoxy-5-methylheptanoyl)pyrrolidin-2-yl)-3-methoxy-2-methylpropanamido)-3-phenylpropanoate;

(S)-methyl 2-((2R,3R)-3-((S)-1-((3R,4S,5S)-4-((S)-4-amino-2-((S)-2-(dimethylamino)-3-methylbutanamido)-N-methylbutanamido)-3-methoxy-5-methylheptanoyl)pyrrolidin-2-yl)-3-methoxy-2-methylpropanamido)-3-phenylpropanoate;

(S)-2-((2R,3R)-3-((S)-1-((3R,4S,5S)-4-((2S,3S)-3-azido-2-((S)-2-(dimethylamino)-3-methylbutanamido)-N-methylbutanamido)-3-methoxy-5-methylheptanoyl)pyrrolidin-2-yl)-3-methoxy-2-methylpropanamido)-3-phenylpropanoic acid;

(S)-methyl 2-((2R,3R)-3-((S)-1-((3R,4S,5S)-4-((R)-2-((S)-2-(dimethylamino)-3-methylbutanamido)-3-mercapto-N-methylpropanamido)-3-methoxy-5-methylheptanoyl)pyrrolidin-2-yl)-3-methoxy-2-methylpropanamido)-3-phenylpropanoate;

(S)-2-((2R,3R)-3-((S)-1-((3R,4S,5S)-4-((R)-2-((S)-2-(dimethylamino)-3-methylbutanamido)-3-mercapto-N-methylpropanamido)-3-methoxy-5-methylheptanoyl)pyrrolidin-2-yl)-3-methoxy-2-methylpropanamido)-3-phenylpropanoic acid;

(S)-2-((2R,3R)-3-((S)-1-((3R,4S,5S)-4-((S)-2-((S)-2-(dimethylamino)-3-methylbutanamido)-3-hydroxy-N-methylpropanamido)-3-methoxy-5-methylheptanoyl)pyrrolidin-2-yl)-3-methoxy-2-methylpropanamido)-3-phenylpropanoic acid;

(S)-2-((2R,3R)-3-((S)-1-((3R,4S,5S)-4-((2S,3R)-2-((S)-2-(dimethylamino)-3-methylbutanamido)-3-hydroxy-N-methylbutanamido)-3-methoxy-5-methylheptanoyl)pyrrolidin-2-yl)-3-methoxy-2-methylpropanamido)-3-phenylpropanoic acid;

(S)-methyl 2-((2R,3R)-3-((S)-1-((3R,4S,5S)-4-((2S,3S)-3-amino-2-((S)-2-(dimethylamino)-3-methylbutanamido)-N-methylbutanamido)-3-methoxy-5-methylheptanoyl)pyrrolidin-2-yl)-3-methoxy-2-methylpropanamido)-3-phenylpropanoate;

(S)-2-((2R,3R)-3-((S)-1-((3R,4S,5S)-4-((2S,3S)-3-amino-2-((S)-2-(dimethylamino)-3-methylbutanamido)-N-methylbutanamido)-3-methoxy-5-methylheptanoyl)pyrrolidin-2-yl)-3-methoxy-2-methylpropanamido)-3-phenylpropanoic acid;

(2S,3S)-3-azido-2-((S)-2-(dimethylamino)-3-methylbutanamido)-N-((3R,4S,5S)-3-methoxy-1-((S)-2-((1R,2R)-1-methoxy-2-methyl-3-oxo-3-(phenethylamino)propyl)pyrrolidin-1-yl)-5-methyl-1-oxoheptan-4-yl)-N-methylbutanamide;

(2S,3S)-3-azido-2-((S)-2-(dimethylamino)-3-methylbutanamido)-N-((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N-methylbutanamide;

(2S,3S)-3-azido-N-((3R,4S,5S)-1-((S)-2-((1R,2R)-3-((4-chlorophenethyl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N-methylbutanamide;

(2S,3S)-3-azido-N-((3R,4S,5S)-1-((S)-2-((1R,2R)-3-((2-chlorophenethyl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N-methylbutanamide;

(2S,3S)-3-amino-2-((S)-2-(dimethylamino)-3-methylbutanamido)-N-((3R,4S,5S)-3-methoxy-1-((S)-2-((1R,2R)-1-methoxy-2-methyl-3-oxo-3-(phenethylamino)propyl)pyrrolidin-1-yl)-5-methyl-1-oxoheptan-4-yl)-N-methylbutanamide;

(2S,3S)-3-amino-2-((S)-2-(dimethylamino)-3-methylbutanamido)-N-((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N-methylbutanamide;

(2S,3S)-3-amino-N-((3R,4S,5S)-1-((S)-2-((1R,2R)-3-((4-chlorophenethyl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N-methylbutanamide;

(2S,3S)-3-amino-N-((3R,4S,5S)-1-((S)-2-((1R,2R)-3-((2-chlorophenethyl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N-methylbutanamide;

(S)-4-amino-2-((S)-2-(dimethylamino)-3-methylbutanamido)-N-((3R,4S,5S)-3-methoxy-1-((S)-2-((1R,2R)-1-methoxy-2-methyl-3-oxo-3-(phenethylamino)propyl)pyrrolidin-1-yl)-5-methyl-1-oxoheptan-4-yl)-N-methylbutanamide;

(S)-4-amino-2-((S)-2-(dimethylamino)-3-methylbutanamido)-N-((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N-methylbutanamide;

(S)-4-amino-N-((3R,4S,5S)-1-((S)-2-((1R,2R)-3-((4-chlorophenethyl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N-methylbutanamide;

(S)-4-amino-N-((3R,4S,5S)-1-((S)-2-((1R,2R)-3-((2-chlorophenethyl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N-methylbutanamide;

methyl ((2R,3R)-3-((S)-1-((3R,4S,5S)-4-((S)-2-((S)-2-(dimethylamino)-3-methylbutanamido)-N-methylpent-4-ynamido)-3-methoxy-5-methylheptanoyl)pyrrolidin-2-yl)-3-methoxy-2-methylpropanoyl)-L-phenylalaninate;

(2S,3S)—N-((3R,4S,5S)-1-((S)-2-((1R,2R)-3-(((S)-1-amino-1-oxo-3-phenylpropan-2-yl)amino)-1-methoxy-2-methyl-3-oxopropyl)pyrrolidin-1-yl)-3-methoxy-5-methyl-1-oxoheptan-4-yl)-3-azido-2-((S)-2-(dimethylamino)-3-methylbutanamido)-N-methylbutanamide;

(2S,3S)-3-azido-2-((S)-2-(dimethylamino)-3-methylbutanamido)-N-((3R,4S,5S)-3-methoxy-1-((S)-2-((1R,2R)-1-methoxy-2-methyl-3-oxo-3-((2-(pyridin-2-yl)ethyl)amino)propyl)pyrrolidin-1-yl)-5-methyl-1-oxoheptan-4-yl)-N-methylbutanamide;

(2S,3S)-3-azido-N-((3R,4S,5S)-1-((S)-2-((1R,2R)-3-(((S)-1-(tert-butylamino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N-methylbutanamide;

methyl ((2R,3R)-3-((S)-1-((3R,4S,5S)-4-((2S,3S)-3-azido-2-((S)-2-(dimethylamino)-3-methylbutanamido)-N-methylbutanamido)-3-methoxy-5-methylheptanoyl)pyrrolidin-2-yl)-3-methoxy-2-methylpropanoyl)-L-valinate;

methyl ((2R,3R)-3-((S)-1-((3R,4S,5S)-4-((S)-6-amino-2-((S)-2-(dimethylamino)-3-methylbutanamido)-N-methylhexanamido)-3-methoxy-5-methylheptanoyl) pyrrolidin-2-yl)-3-methoxy-2-methylpropanoyl)-L-phenylalaninate;

(S)-3-((S)-2-(dimethylamino)-3-methylbutanamido)-4-(((3R,4S,5S)-3-methoxy-1-((S)-2-((1R,2R)-1-methoxy-3-(((S)-1-methoxy-1-oxo-3-phenylpropan-2-yl)amino)-2-methyl-3-oxopropyl)pyrrolidin-1-yl)-5-methyl-1-oxoheptan-4-yl)(methyl)amino)-4-oxobutanoic acid;

(2S,3R)-2-((S)-2-(dimethylamino)-3-methylbutanamido)-3-hydroxy-N-((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N-methylbutanamide;

methyl ((2R,3R)-3-((S)-1-((3R,4S,5S)-4-((2S,3S)-3-azido-2-((S)-2-(dimethylamino)-3-methylbutanamido)-N-methylbutanamido)-3-methoxy-5-methylheptanoyl)pyrrolidin-2-yl)-3-methoxy-2-methylpropanoyl)-L-isoleucinate;

(2S,3S)-3-amino-N-((3R,4S,5S)-1-((S)-2-((1R,2R)-3-(((S)-1-amino-1-oxo-3-phenylpropan-2-yl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N-methylbutanamide;

(2S,3S)-3-amino-N-((3R,4S,5S)-1-((S)-2-((1R,2R)-3-(((S)-1-(tert-butylamino)-1-oxo-3-phenylpropan-2-yl) amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N-methylbutanamide;

methyl ((2R,3R)-3-((S)-1-((3R,4S,5S)-4-((S)-3-azido-N-methyl-2-((S)-3-methyl-2-(methylamino)butanamido) propanamido)-3-methoxy-5-methylheptanoyl)pyrrolidin-2-yl)-3-methoxy-2-methylpropanoyl)-L-phenylalaninate;

methyl ((2R,3R)-3-((S)-1-((3R,4S,5S)-4-((2S,3S)-3-azido-N-methyl-2-((S)-3-methyl-2-(methylamino)butanamido)butanamido)-3-methoxy-5-methylheptanoyl) pyrrolidin-2-yl)-3-methoxy-2-methylpropanoyl)-L-phenylalaninate;

(2S,3S)—N-((3R,4S,5S)-1-((S)-2-((1R,2R)-3-(((S)-1-amino-1-oxo-3-phenylpropan-2-yl)amino)-1-methoxy-2-methyl-3-oxopropyl)pyrrolidin-1-yl)-3-methoxy-5-methyl-1-oxoheptan-4-yl)-3-azido-N-methyl-2-((S)-3-methyl-2-(methylamino)butanamido)butanamide;

(2S,3S)—N-((3R,4S,5S)-1-((S)-2-((1R,2R)-3-(((S)-1-amino-1-oxo-3-phenylpropan-2-yl)amino)-1-methoxy-2-methyl-3-oxopropyl)pyrrolidin-1-yl)-3-methoxy-5-methyl-1-oxoheptan-4-yl)-3-azido-2-((S)-2-dimethylamino)-3-methylbutanamido-N-methylbutanamide;

((2S,3S)-3-azido-N-((3R,4S,5S)-1-((S)-2-((1R,2R)-3-(((S)-1-(tert-butylamino)-1-oxo-3-phenylpropan-2-yl) amino)-1-methoxy-2-methyl-3-oxopropyl)pyrrolidin-1-yl)-3-methoxy-5-methyl-1-oxoheptan-4-yl)-N-methyl-2-((S)-3-methyl-2-(methylamino)butanamido) butanamide;

tert-butyl ((2R,3R)-3-((S)-1-((3R,4S,5S)-4-((2S,3S)-3-azido-N-methyl-2-((S)-3-methyl-2-(methylamino)butanamido)butanamido)-3-methoxy-5-methylheptanoyl) pyrrolidin-2-yl)-3-methoxy-2-methylpropanoyl)-L-phenylalaninate;

((2R,3R)-3-((S)-1-((3R,4S,5S)-4-((2S,3S)-3-azido-N-methyl-2-((S)-3-methyl-2-(methylamino)butanamido) butanamido)-3-methoxy-5-methylheptanoyl)pyrrolidin-2-yl)-3-methoxy-2-methylpropanoyl)-L-phenylalanine;

tert-butyl ((2R,3R)-3-((S)-1-((3R,4S,5S)-4-((2S,3S)-3-azido-2-((S)-2-(dimethylamino)-3-methylbutanamido)-N-methylbutanamido)-3-methoxy-5-methylheptanoyl)pyrrolidin-2-yl)-3-methoxy-2-methylpropanoyl)-L-phenylalaninate;

(2S,3S)-3-azido-2-((S)-2-(dimethylamino)-3-methylbutanamido)-N-((3R,4S,5S)-3-methoxy-1-((S)-2-((1R,2R)-1-methoxy-2-methyl-3-oxo-3-(((S)-2-phenyl-1-(1H-tetrazol-5-yl)ethyl)amino)propyl)pyrrolidin-1-yl)-5-methyl-1-oxoheptan-4-yl)-N-methylbutanamide;

(2S,3S)-3-azido-N-((3R,4S,5S)-3-methoxy-1-((S)-2-((1R,2R)-1-methoxy-2-methyl-3-oxo-3-(((S)-2-phenyl-1-(1H-tetrazol-5-yl)ethyl)amino)propyl)pyrrolidin-1-yl)-5-methyl-1-oxoheptan-4-yl)-N-methyl-2-((S)-3-methyl-2-(methylamino)butanamido) butanamide;

(2S,3S)-3-azido-2-((S)-2-(dimethylamino)-3-methylbutanamido)-N-((3R,4S,5S)-3-methoxy-1-((S)-2-((1R,2R)-1-methoxy-2-methyl-3-oxo-3-(((S)-2-phenyl-1-(thiazol-2-yl)ethyl)amino)propyl)pyrrolidin-1-yl)-5-methyl-1-oxoheptan-4-yl)-N-methylbutanamide;

tert-butyl ((2R,3R)-3-((S)-1-((3R,4S,5S)-4-((2S,3S)-3-amino-2-((S)-2-(dimethylamino)-3-methylbutanamido)-N-methylbutanamido)-3-methoxy-5-methylheptanoyl)pyrrolidin-2-yl)-3-methoxy-2-methylpropanoyl)-L-phenylalaninate;

(2S,3S)-3-amino-2-((S)-2-(dimethylamino)-3-methylbutanamido)-N-((3R,4S,5S)-3-methoxy-1-((S)-2-((1R,2R)-1-methoxy-2-methyl-3-oxo-3-(((S)-2-phenyl-1-(1H-tetrazol-5-yl)ethyl)amino)propyl)pyrrolidin-1-yl)-5-methyl-1-oxoheptan-4-yl)-N-methylbutanamide; and (2S,3S)-3-amino-2-((S)-2-(dimethylamino)-3-methylbutanamido)-N-((3R,4S,5S)-3-methoxy-1-((S)-2-((1R,2R)-1-methoxy-2-methyl-3-oxo-3-(((S)-2-phenyl-1-(thiazol-2-yl)ethyl)amino)propyl)pyrrolidin-1-yl)-5-methyl-1-oxoheptan-4-yl)-N-methylbutanamide;

or a pharmaceutically acceptable salt thereof.

11. The method of claim 10, wherein the cancer is prostate cancer, pancreatic cancer, breast cancer, or colorectal cancer.

12. The method of claim 10, comprising administering to the subject the compound in combination with one or more additional chemotherapeutic active agents.

13. The method of claim 10, wherein the compound is (2S,3S)—N-((3R,4S,5S)-1-((S)-2-((1R,2R)-3-(((S)-1-amino-1-oxo-3-phenylpropan-2-yl)amino)-1-methoxy-2-methyl-3-oxopropyl)pyrrolidin-1-yl)-3-methoxy-5-methyl-1-oxoheptan-4-yl)-3-azido-N-methyl-2-((S)-3-methyl-2-(methylamino)butanamido)butanamide or a pharmaceutically acceptable salt thereof.

14. The method of claim 13, wherein the cancer is prostate cancer, pancreatic cancer, breast cancer, or colorectal cancer.

15. A method of treating cancer in a subject in need thereof, comprising administering to the subject a composition comprising (2S,3S)—N-((3R,4S,5S)-1-((S)-2-((1R,2R)-3-(((S)-1-amino-1-oxo-3-phenylpropan-2-yl)amino)-1-methoxy-2-methyl-3-oxopropyl)pyrrolidin-1-yl)-3-methoxy-5-methyl-1-oxoheptan-4-yl)-3-azido-2-((S)-2-dimethylamino)-3-methylbutanamido-N-methylbutanamide or a pharmaceutically acceptable salt thereof.

16. The method of claim 15, wherein the cancer is prostate cancer, pancreatic cancer, breast cancer, or colorectal cancer.

* * * * *